(12) United States Patent
Kubota et al.

(10) Patent No.: US 7,592,140 B2
(45) Date of Patent: Sep. 22, 2009

(54) 2', 5'-OLIGOADENYLATE PHOSPHODIESTERASE

(75) Inventors: Kazuishi Kubota, Tokyo (JP); Kaori Nakahara, Tokyo (JP); Ayako Hara, Tokyo (JP); Yohei Ozeki, Tokyo (JP); Yasuteru Iijima, Funabashi (JP)

(73) Assignee: Sankyo Company, Limited, Tokyo (JP)

( * ) Notice: Subject to any disclaimer, the term of this patent is extended or adjusted under 35 U.S.C. 154(b) by 442 days.

(21) Appl. No.: 11/078,951

(22) Filed: Mar. 11, 2005

(65) Prior Publication Data
US 2005/0272119 A1 Dec. 8, 2005

Related U.S. Application Data

(63) Continuation of application No. PCT/JP03/11660, filed on Sep. 11, 2003.

(30) Foreign Application Priority Data
Sep. 13, 2002 (JP) ............................ 2002-267797

(51) Int. Cl.
*C12N 15/55* (2006.01)
*C12Q 1/68* (2006.01)
*C12N 9/16* (2006.01)

(52) U.S. Cl. ..................... 435/6; 435/320.1; 435/252.3; 435/325; 435/358; 435/365; 435/252.33; 435/196; 435/19; 536/23.2

(58) Field of Classification Search ........................ None
See application file for complete search history.

(56) References Cited

FOREIGN PATENT DOCUMENTS

| WO | 01/75067 | * | 10/2001 |
| WO | 02/068579 | * | 9/2002 |
| WO | 02/077257 | * | 10/2002 |

OTHER PUBLICATIONS

Derwent N-GeneSeq Accession No. AAS89954 (Feb. 13, 2002).*
Kappel et al. "Regulating Gene Expression in Transgenic Animals", Current Opinion in Biotechnology 3:548-553, 1992.*
Mullins et al. "Trangenesis in Nonmurine Species", Hypertension 22(4):630-633, 1993.*
Mullins et al. "Trangenesis in the Rat and Larger Mammals", J. Clin. Invest. 97(7):1557-1560, 1996.*
Wigley et al. "site-pecific Trangene Insertion: an Approach", Reprod. Fert. Dev. 6:585-588, 1994.*
Cameron, "Recent Advances in Transgenic Technology", Molecular Biotechnology 7:253-265, 1997.*
M.R. Player and P.F. Torrence, "The 2-5A System: Modulation of Viral and Cellular Processes Through Acceleration of RNA Degradation," *Pharmacol. Ther.*, vol. 78, No. 2, (1998), pp. 55-113.
Kohei Miyazono and Kazuo Sugamura, editors, "Bio Science Yogo Library, Cytokines and Growth Factors," published by Youdosha Co., Ltd., Japan, (1998), pp. 178-185.
H. Takayanagi, et al., "RANKL maintains bone homeostasis through c-Fos-dependent induction of interferon-β," *Nature*, vol. 416, (2002), pp. 744-749.
J. Carpten et al., "Germline mutations in the ribonuclease L gene in families showing linkage with HPC1," *Nature Genetics*, vol. 30, (2002), pp. 181-184.
M. Saarma et al., "Nerve Growth Factor Induces Changes in (2'-5')Oligo(A) Synthetase and 2'-Phosphodiesterase Activities during Differentiation of PC12 Pheochromocytoma Cells," *Experimental Cell Research*, Vo. 166, (1986), pp. 229-236.
A. Schmidt et al., "An interferon-induced phosphodiesterase degrading (2'—5')oligoisoadenylate and the C-C-A terminus of tRNA," *Proc. Natl. Acad. Sci. USA*, vol. 76, No. 10, (Oct. 1979), pp. 4788-4792.
K. Kubota et al., "Identification of 2'-Phosphodiesterase, Which Plays a Role in the 2-5A System Regulated by Interferon," *Jour. of Biol. Chem.*, vol. 279, No. 36, (2004), pp. 37832-37841.
M.I. Johnston and W.G. Hearl, "Purification and Characterizaton of a 2'-Phosphodiesterase from Bovine Spleen," *Jour. of Biol. Chem.*, vol. 262, No. 17, pp. 8377-8382, (1987).
H. Sawai et al., "2', 5'-Oligoadenylate and 2', 5'-Oligoadenylate Phosphodiesterase in Human Plasma," *Biochem. and Biophys. Research Commun.*, vol. 125, No. 3, (Dec. 28, 1984), pp. 1061-1066.
English-language International Preliminary Examination Report dated Nov. 7, 2003 of International Application PCT/JP03/11660 filed Sep. 11, 2003; Applicant: Sankyo Company, Limited.

* cited by examiner

*Primary Examiner*—Rebecca Prouty
(74) *Attorney, Agent, or Firm*—Frishauf, Holtz, Goodman & Chick, P.C.

(57) ABSTRACT

Polypeptides having 2',5'-oligoadenylate phosphodiesterase activity, antibodies against the polypeptides, polynucleotides coding for the polypeptides, recombinant plasmid DNAs into which the polynucleotides have been inserted, host cells transformed by the recombinant plasmid DNAs, processes for screening for 2',5'-oligoadenylate phosphodiesterase activity inhibitor substances, and processes for screening for 2',5'-oligoadenylate phosphodiesterase expression regulation inhibitor substances. The polypeptides, polynucleotides and host cells are useful for searching for therapeutic agents for viral infections and tumors.

21 Claims, 15 Drawing Sheets

Figure 1
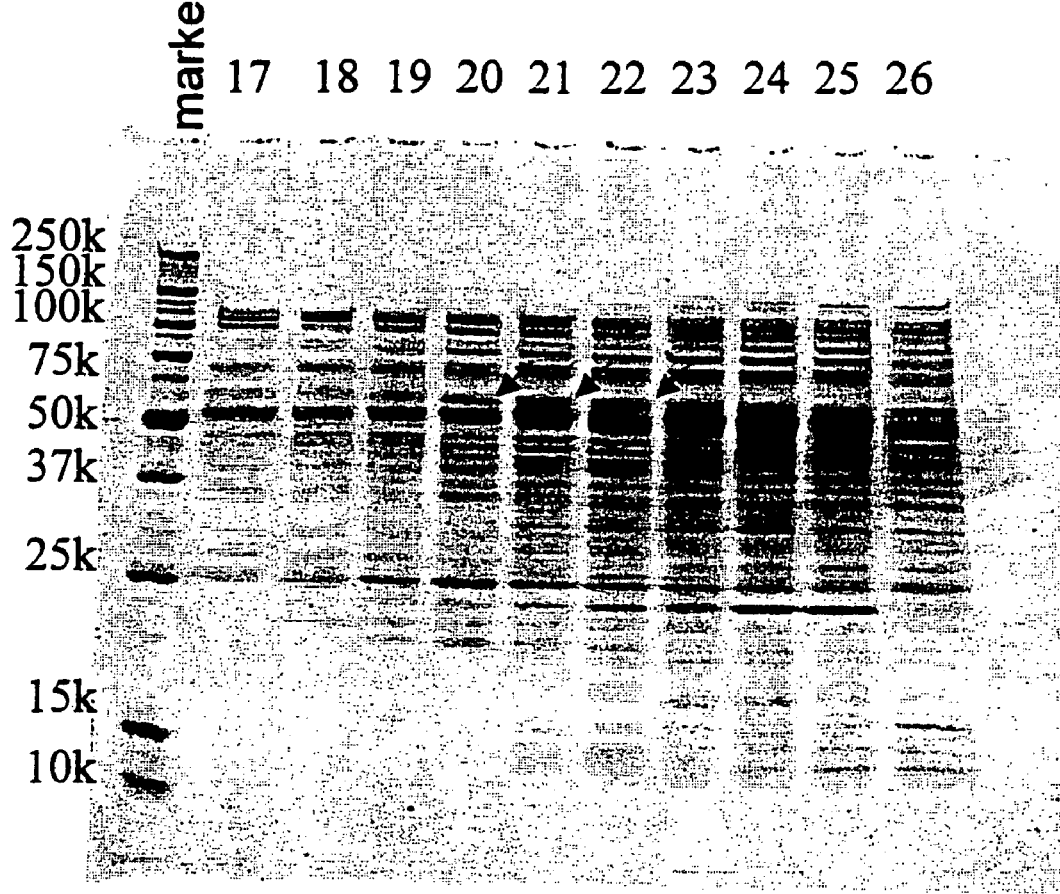
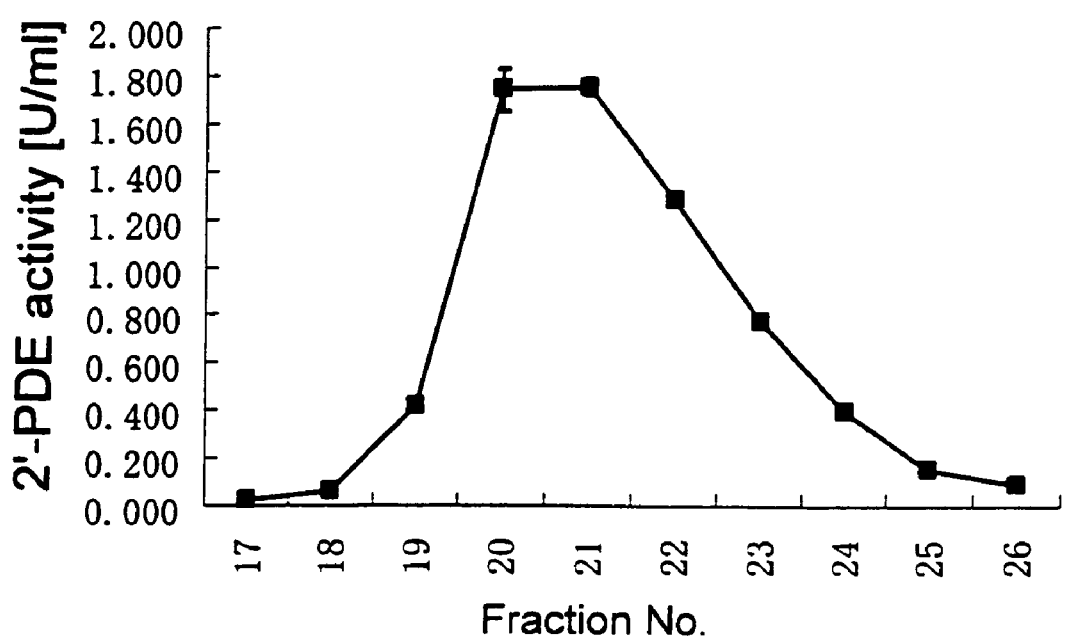

Precursor ion :
[M+2H] 641.82 (monoisotopic mass)

Precursor ion :
[M+2H] 653.34 (monoisotopic mass)

Precursor ion :
[M+2H] 691.88 (monoisotopic mass)

Figure 5
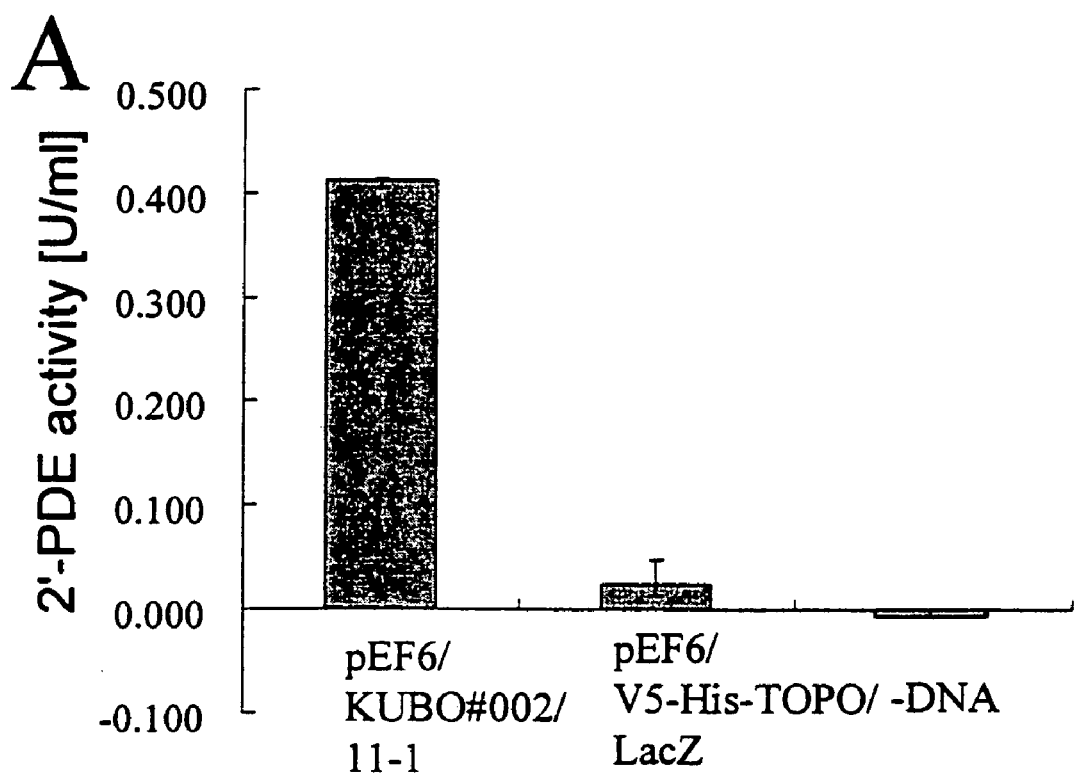
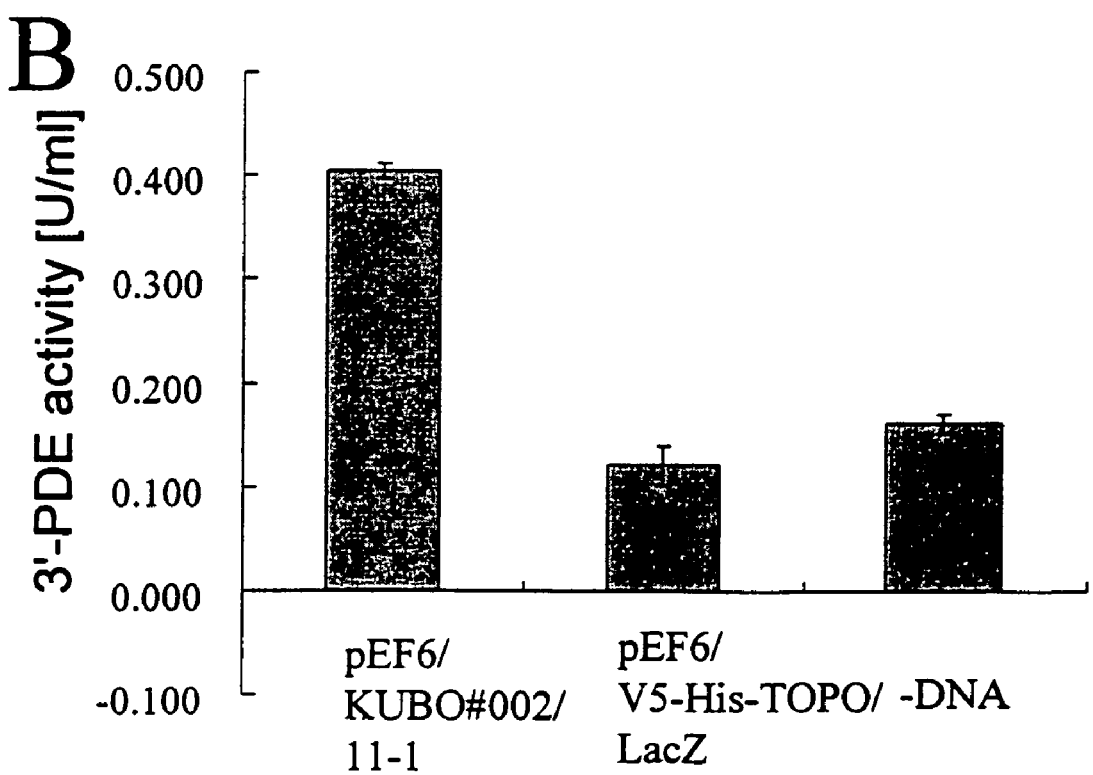

| Substrate | Relative cutting efficiency[1] | | |
|---|---|---|---|
| | Experimental value | Reference value[2] | Reference value[3] |
| A2'pA | 1.0 | 1.0 | 1.0 |
| A3'pA | 0.51 | 0.29 | |
| A2'pA2'pA | 1.5 | | 1.7 |
| A3'pA3'pA | 1.2 | | 163 |
| pA2'pA2'pA | 1.4 | | 1.5 |
| pA3'pA3'pA | 1.4 | | |

Figure 8
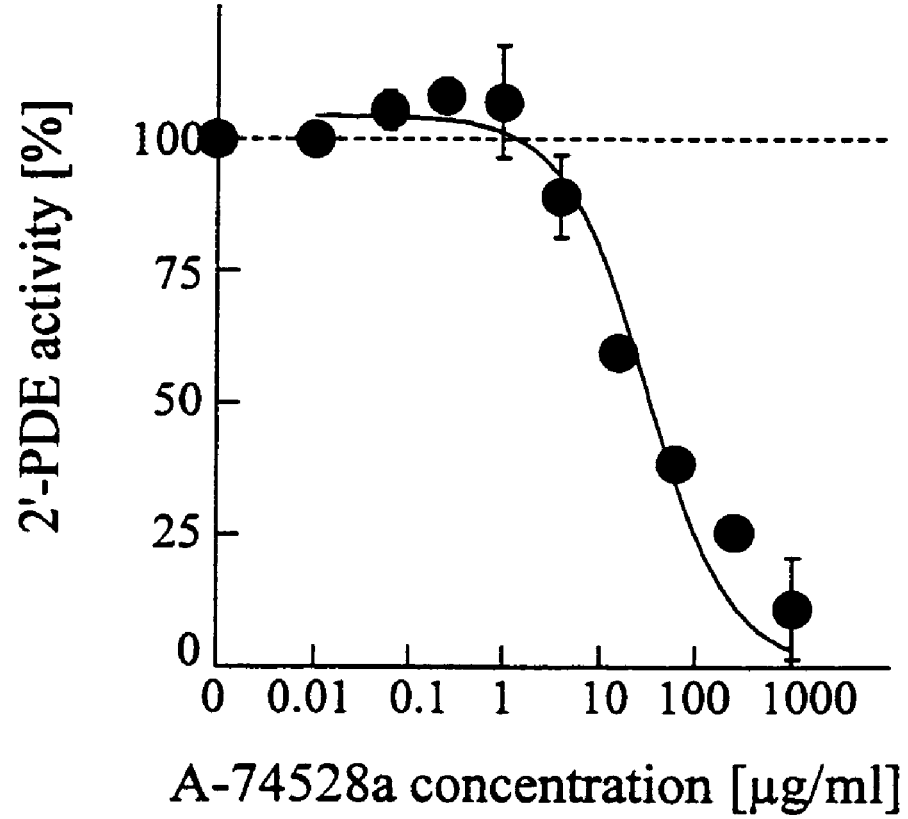
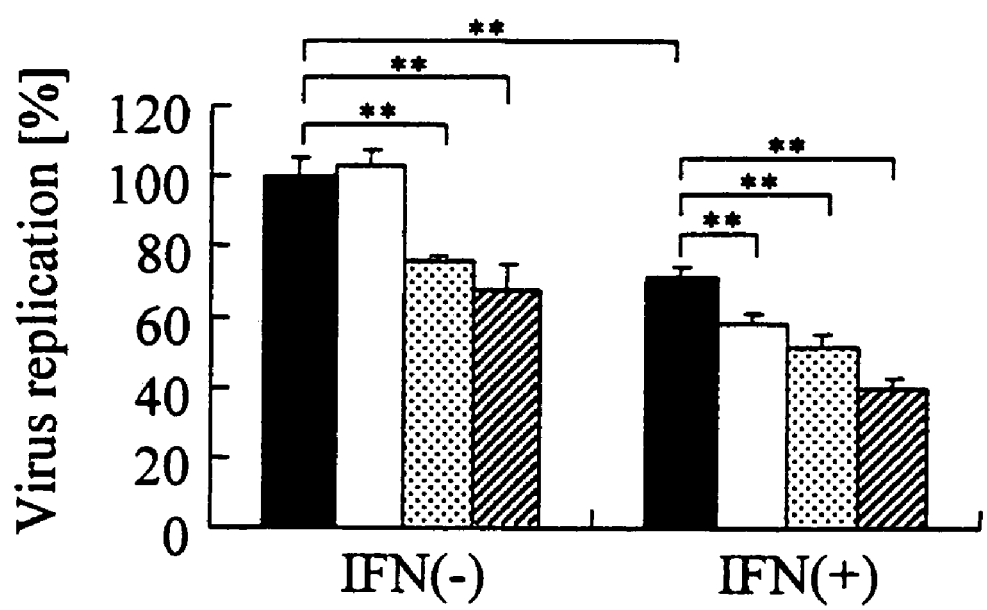

```
  1 MWRLPGARAA LRVIRTAVEK LSWAEAGSQT AAGAMERAVV RCVPSEPKLS
 51 LSFALADGSH KNMQRDQSEP LGRVLSRIAT NALKGHAKAA AAKKSRKSRP
101 NASGGAACSG PGPEPAVFCE PVVKLYYREE AVAEDVLNVD AWQDGAVLQI
151 GDVKYKVERN PPAFTELQLP RYIMAGFPVC PKLSLEFGDP ASSLFRWYKE
201 AKPGAAEPEV GVPSSLSPSS PSSSWTETDV EERVYTPSNA DIGLRLKLHC
251 TPGDGQRFGH SRELESVCVV EAGPGTCTFD HRHLYTKKVT EDALIRTVSY
301 NILADTYAQT EFSRTVLYPY CAPYALELDY RQNLIQKELT GYNADVICLQ
351 EVDRAVFSDS LVPALEAFGL EGVFRIKQHE GLATFYRKSK FSLLSQHDIS
401 FYEALESDPL HKELLEKLVL YPSAQEKVLQ RSSVLQVSVL QSTKDSSKRI
451 CVANTHLYWH PKGGYIRLIQ MAVALAHIRH VSCDLYPGIP VIFCGDFNST
501 PSTGMYHFVI NGSIPEDHED WASNGEEERC NMSLTHFFKL KSACGEPAYT
551 NYVGGFHGCL DYIFIDLNAL EVEQVIPLPS HEEVTTHQAL PSVSHPSDHI
601 ALVCDLKWK
```

B Precursor ion : [M+2H] 451.75 (monoisotopic mass)

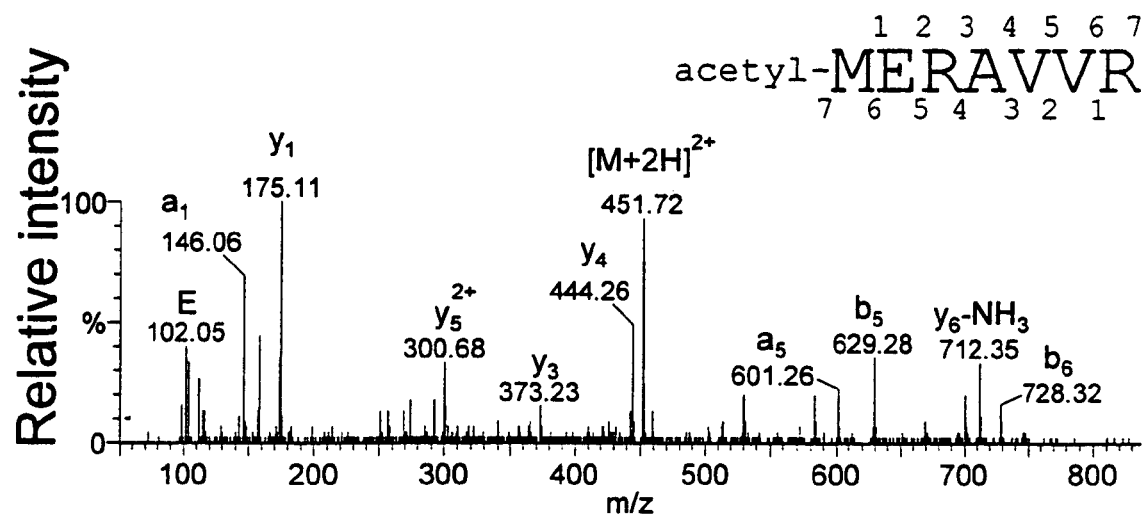

SEQUENCE LISTING

<160> NUMBER OF SEQ ID NOS: 14

<210> SEQ ID NO 1
<211> LENGTH: 1830
<212> TYPE: DNA
<213> ORGANISM: Homo sapiens
<220> FEATURE:
<221> NAME/KEY: CDS
<222> LOCATION: (1)..(1827)
<223> OTHER INFORMATION:
<220> FEATURE:
<221> NAME/KEY: misc_feature

<400> SEQUENCE: 1

```
atg tgg agg ctc cca ggc gcc cgc gcc gcg ctt cgg gtg atc cgg acg      48
Met Trp Arg Leu Pro Gly Ala Arg Ala Ala Leu Arg Val Ile Arg Thr
1               5                   10                  15 gcg gtg gag aag ctg agc tgg gct gaa gcg ggg agc cag aca gcg gcg      96
Ala Val Glu Lys Leu Ser Trp Ala Glu Ala Gly Ser Gln Thr Ala Ala
            20                  25                  30 gga gcg atg gag cgc gct gta gtg cgc tgc gta cct tcg gaa ccc aag     144
Gly Ala Met Glu Arg Ala Val Val Arg Cys Val Pro Ser Glu Pro Lys
        35                  40                  45 ctg agc ctg tca ttc gct ttg gct gat ggt agc cac aag aac atg cag     192
Leu Ser Leu Ser Phe Ala Leu Ala Asp Gly Ser His Lys Asn Met Gln
    50                  55                  60 cgc gac cag agc gag ccg ctg ggt cga gtc ctc agc cgc atc gct acc     240
Arg Asp Gln Ser Glu Pro Leu Gly Arg Val Leu Ser Arg Ile Ala Thr
65                  70                  75                  80 aat gcc cta aag ggt cac gct aag gcg gcc gcc gcc aag aag agc agg     288
Asn Ala Leu Lys Gly His Ala Lys Ala Ala Ala Ala Lys Lys Ser Arg
                85                  90                  95 aag agc cgg ccg aat gct agc ggc ggt gcg gcc tgt tca ggg ccg ggg     336
Lys Ser Arg Pro Asn Ala Ser Gly Gly Ala Ala Cys Ser Gly Pro Gly
            100                 105                 110 cct gag ccg gct gtg ttc tgc gag ccc gtg gtg aag ctg tac tac cgg     384
Pro Glu Pro Ala Val Phe Cys Glu Pro Val Val Lys Leu Tyr Tyr Arg
        115                 120                 125 gaa gag gca gtg gct gag gac gtg ctc aac gtg gat gcc tgg caa gac     432
Glu Glu Ala Val Ala Glu Asp Val Leu Asn Val Asp Ala Trp Gln Asp
    130                 135                 140 ggc gcg gtg ctg cag atc ggc gat gtt aag tac aag gtg gag cgc aac     480
Gly Ala Val Leu Gln Ile Gly Asp Val Lys Tyr Lys Val Glu Arg Asn
145                 150                 155                 160
```

```
ccg ccc gcc ttc acc gaa ctg cag ttg ccg cgc tac atc atg gcc ggg      528
Pro Pro Ala Phe Thr Glu Leu Gln Leu Pro Arg Tyr Ile Met Ala Gly
            165                 170                 175 ttc cct gtg tgc ccc aaa ctc agc ctc gaa ttt ggg gat ccc gcc agc      576
Phe Pro Val Cys Pro Lys Leu Ser Leu Glu Phe Gly Asp Pro Ala Ser
        180                 185                 190 tcc ctt ttc cgc tgg tat aag gaa gcc aag ccc gga gcg gcg gag ccc      624
Ser Leu Phe Arg Trp Tyr Lys Glu Ala Lys Pro Gly Ala Ala Glu Pro
    195                 200                 205 gag gtc ggt gtc ccc tcg tca ttg tct ccc tcc tca cct tct tct tct      672
Glu Val Gly Val Pro Ser Ser Leu Ser Pro Ser Ser Pro Ser Ser Ser
210                 215                 220 tgg act gag act gat gtg gag gag cgt gtc tac acc ccg tcc aat gcc      720
Trp Thr Glu Thr Asp Val Glu Glu Arg Val Tyr Thr Pro Ser Asn Ala
225                 230                 235                 240 gac atc ggg cta agg ctc aag ctt cac tgc acc cca ggc gat ggg cag      768
Asp Ile Gly Leu Arg Leu Lys Leu His Cys Thr Pro Gly Asp Gly Gln
                245                 250                 255 cgc ttt ggg cac agc cgg gag ttg gaa agt gtg tgt gtg gta gag gct      816
Arg Phe Gly His Ser Arg Glu Leu Glu Ser Val Cys Val Val Glu Ala
            260                 265                 270 ggg cct ggc acc tgc act ttt gac cac cgg cat ctc tac acg aag aag      864
Gly Pro Gly Thr Cys Thr Phe Asp His Arg His Leu Tyr Thr Lys Lys
        275                 280                 285 gtg act gag gac gct ctc atc cgc act gtc tct tac aac atc ctg gca      912
Val Thr Glu Asp Ala Leu Ile Arg Thr Val Ser Tyr Asn Ile Leu Ala
    290                 295                 300 gac acg tac gcg cag act gag ttc tcg cga acg gtt ctg tac cca tac      960
Asp Thr Tyr Ala Gln Thr Glu Phe Ser Arg Thr Val Leu Tyr Pro Tyr
305                 310                 315                 320 tgt gcc ccc tac gcc ctg gag ctc gac tac cgc cag aac ctt atc cag     1008
Cys Ala Pro Tyr Ala Leu Glu Leu Asp Tyr Arg Gln Asn Leu Ile Gln
                325                 330                 335 aag gaa ctc acc ggc tac aac gcc gat gtc atc tgt ttg cag gag gtt     1056
Lys Glu Leu Thr Gly Tyr Asn Ala Asp Val Ile Cys Leu Gln Glu Val
            340                 345                 350 gac cgc gca gtg ttt tct gac agc ttg gta ccc gcc cta gag gcc ttc     1104
Asp Arg Ala Val Phe Ser Asp Ser Leu Val Pro Ala Leu Glu Ala Phe
        355                 360                 365 ggg ctc gag ggg gtg ttt cga atc aag cag cac gaa ggc ctg gcc act     1152
Gly Leu Glu Gly Val Phe Arg Ile Lys Gln His Glu Gly Leu Ala Thr
    370                 375                 380 ttc tac cga aag tct aag ttc agc ctt ctt agc cag cat gac att tca     1200
Phe Tyr Arg Lys Ser Lys Phe Ser Leu Leu Ser Gln His Asp Ile Ser
385                 390                 395                 400 ttc tac gaa gcc ctc gag tcc gac cca ctt cac aaa gaa ctg ctg gag     1248
Phe Tyr Glu Ala Leu Glu Ser Asp Pro Leu His Lys Glu Leu Leu Glu
                405                 410                 415 aaa cta gtt ttg tac cca tca gcg cag gag aag gtg ctc cag aga tct     1296
Lys Leu Val Leu Tyr Pro Ser Ala Gln Glu Lys Val Leu Gln Arg Ser
            420                 425                 430 tct gtt ctt cag gtt tca gtt ctt cag tct aca aag gac tct tct aaa     1344
Ser Val Leu Gln Val Ser Val Leu Gln Ser Thr Lys Asp Ser Ser Lys
        435                 440                 445 agg ata tgt gtt gct aat acc cat ctt tac tgg cat cct aaa ggt ggg     1392
Arg Ile Cys Val Ala Asn Thr His Leu Tyr Trp His Pro Lys Gly Gly
    450                 455                 460 tat att cgc ctc att caa atg gca gta gcc ttg gct cac ata aga cat     1440
Tyr Ile Arg Leu Ile Gln Met Ala Val Ala Leu Ala His Ile Arg His
465                 470                 475                 480
```

```
gtt tca tgt gat ctg tat cct ggc ata cca gtt ata ttt tgt ggg gac      1488
Val Ser Cys Asp Leu Tyr Pro Gly Ile Pro Val Ile Phe Cys Gly Asp
            485                 490                 495 ttt aat agt aca cca tca aca gga atg tat cat ttt gtc atc aat ggc      1536
Phe Asn Ser Thr Pro Ser Thr Gly Met Tyr His Phe Val Ile Asn Gly
            500                 505                 510 agc att cca gag gat cat gaa gac tgg gct tcc aat ggg gag gag gaa      1584
Ser Ile Pro Glu Asp His Glu Asp Trp Ala Ser Asn Gly Glu Glu Glu
            515                 520                 525 aga tgc aat atg tct ctt aca cat ttc ttc aag ctg aaa agt gct tgt      1632
Arg Cys Asn Met Ser Leu Thr His Phe Phe Lys Leu Lys Ser Ala Cys
            530                 535                 540 ggt gaa cct gct tac aca aat tat gtt ggt ggc ttt cat gga tgt cta      1680
Gly Glu Pro Ala Tyr Thr Asn Tyr Val Gly Gly Phe His Gly Cys Leu
545                 550                 555                 560 gat tac att ttc att gac tta aat gct tta gag gtt gaa cag gtg att      1728
Asp Tyr Ile Phe Ile Asp Leu Asn Ala Leu Glu Val Glu Gln Val Ile
                565                 570                 575 cca tta cct agt cat gaa gaa gtt acc acc cac cag gcc tta cct agt      1776
Pro Leu Pro Ser His Glu Glu Val Thr Thr His Gln Ala Leu Pro Ser
            580                 585                 590 gtt tcc cat ccc tct gat cac ata gca ctt gta tgt gat tta aaa tgg      1824
Val Ser His Pro Ser Asp His Ile Ala Leu Val Cys Asp Leu Lys Trp
            595                 600                 605 aaa tag                                                              1830
Lys

<210> SEQ ID NO 2
<211> LENGTH: 609
<212> TYPE: PRT
<213> ORGANISM: Homo sapiens

<400> SEQUENCE: 2

Met Trp Arg Leu Pro Gly Ala Arg Ala Ala Leu Arg Val Ile Arg Thr
1               5                   10                  15

Ala Val Glu Lys Leu Ser Trp Ala Glu Ala Gly Ser Gln Thr Ala Ala
                20                  25                  30

Gly Ala Met Glu Arg Ala Val Val Arg Cys Val Pro Ser Glu Pro Lys
            35                  40                  45

Leu Ser Leu Ser Phe Ala Leu Ala Asp Gly Ser His Lys Asn Met Gln
        50                  55                  60

Arg Asp Gln Ser Glu Pro Leu Gly Arg Val Leu Ser Arg Ile Ala Thr
65                  70                  75                  80

Asn Ala Leu Lys Gly His Ala Lys Ala Ala Ala Lys Lys Ser Arg
                85                  90                  95

Lys Ser Arg Pro Asn Ala Ser Gly Gly Ala Cys Ser Gly Pro Gly
            100                 105                 110

Pro Glu Pro Ala Val Phe Cys Glu Pro Val Lys Leu Tyr Tyr Arg
        115                 120                 125

Glu Glu Ala Val Ala Glu Asp Val Leu Asn Val Asp Ala Trp Gln Asp
130                 135                 140

Gly Ala Val Leu Gln Ile Gly Asp Val Lys Tyr Lys Val Glu Arg Asn
145                 150                 155                 160

Pro Pro Ala Phe Thr Glu Leu Gln Leu Pro Arg Tyr Ile Met Ala Gly
                165                 170                 175

Phe Pro Val Cys Pro Lys Leu Ser Leu Glu Phe Gly Asp Pro Ala Ser
            180                 185                 190
```

-continued

```
Ser Leu Phe Arg Trp Tyr Lys Glu Ala Lys Pro Gly Ala Ala Glu Pro
        195                 200                 205
Glu Val Gly Val Pro Ser Ser Leu Ser Pro Ser Ser Pro Ser Ser Ser
    210                 215                 220
Trp Thr Glu Thr Asp Val Glu Glu Arg Val Tyr Thr Pro Ser Asn Ala
225                 230                 235                 240
Asp Ile Gly Leu Arg Leu Lys Leu His Cys Thr Pro Gly Asp Gly Gln
                245                 250                 255
Arg Phe Gly His Ser Arg Glu Leu Glu Ser Val Cys Val Val Glu Ala
            260                 265                 270
Gly Pro Gly Thr Cys Thr Phe Asp His Arg His Leu Tyr Thr Lys Lys
        275                 280                 285
Val Thr Glu Asp Ala Leu Ile Arg Thr Val Ser Tyr Asn Ile Leu Ala
    290                 295                 300
Asp Thr Tyr Ala Gln Thr Glu Phe Ser Arg Thr Val Leu Tyr Pro Tyr
305                 310                 315                 320
Cys Ala Pro Tyr Ala Leu Glu Leu Asp Tyr Arg Gln Asn Leu Ile Gln
                325                 330                 335
Lys Glu Leu Thr Gly Tyr Asn Ala Asp Val Ile Cys Leu Gln Glu Val
            340                 345                 350
Asp Arg Ala Val Phe Ser Asp Ser Leu Val Pro Ala Leu Glu Ala Phe
        355                 360                 365
Gly Leu Glu Gly Val Phe Arg Ile Lys Gln His Glu Gly Leu Ala Thr
    370                 375                 380
Phe Tyr Arg Lys Ser Lys Phe Ser Leu Leu Ser Gln His Asp Ile Ser
385                 390                 395                 400
Phe Tyr Glu Ala Leu Glu Ser Asp Pro Leu His Lys Glu Leu Leu Glu
                405                 410                 415
Lys Leu Val Leu Tyr Pro Ser Ala Gln Glu Lys Val Leu Gln Arg Ser
            420                 425                 430
Ser Val Leu Gln Val Ser Val Leu Gln Ser Thr Lys Asp Ser Ser Lys
        435                 440                 445
Arg Ile Cys Val Ala Asn Thr His Leu Tyr Trp His Pro Lys Gly Gly
    450                 455                 460
Tyr Ile Arg Leu Ile Gln Met Ala Val Ala Leu Ala His Ile Arg His
465                 470                 475                 480
Val Ser Cys Asp Leu Tyr Pro Gly Ile Pro Val Ile Phe Cys Gly Asp
                485                 490                 495
Phe Asn Ser Thr Pro Ser Thr Gly Met Tyr His Phe Val Ile Asn Gly
            500                 505                 510
Ser Ile Pro Glu Asp His Glu Asp Trp Ala Ser Asn Gly Glu Glu Glu
        515                 520                 525
Arg Cys Asn Met Ser Leu Thr His Phe Phe Lys Leu Lys Ser Ala Cys
    530                 535                 540
Gly Glu Pro Ala Tyr Thr Asn Tyr Val Gly Gly Phe His Gly Cys Leu
545                 550                 555                 560
Asp Tyr Ile Phe Ile Asp Leu Asn Ala Leu Glu Val Glu Gln Val Ile
                565                 570                 575
Pro Leu Pro Ser His Glu Glu Val Thr Thr His Gln Ala Leu Pro Ser
            580                 585                 590
Val Ser His Pro Ser Asp His Ile Ala Leu Val Cys Asp Leu Lys Trp
        595                 600                 605
```

Lys

<210> SEQ ID NO 3
<211> LENGTH: 11
<212> TYPE: PRT
<213> ORGANISM: Homo sapiens

<400> SEQUENCE: 3

Tyr Ile Met Ala Gly Phe Pro Val Cys Pro Lys
1               5                   10

<210> SEQ ID NO 4
<211> LENGTH: 12
<212> TYPE: PRT
<213> ORGANISM: Homo sapiens

<400> SEQUENCE: 4

Val Tyr Thr Pro Ser Asn Ala Asp Ile Gly Leu Arg
1               5                   10

<210> SEQ ID NO 5
<211> LENGTH: 12
<212> TYPE: PRT
<213> ORGANISM: Homo sapiens

<400> SEQUENCE: 5

Asn Pro Pro Ala Phe Thr Glu Leu Gln Leu Pro Arg
1               5                   10

<210> SEQ ID NO 6
<211> LENGTH: 25
<212> TYPE: DNA
<213> ORGANISM: Artificial
<220> FEATURE:
<223> OTHER INFORMATION: Oligonucleotide primer 1 for amplifying a
      polynucleotide which encodes human 2',5'-oligoadenylate
      phosphodiesterase

<400> SEQUENCE: 6
ctcctcagct ccacctgaca gtagg                                          25

<210> SEQ ID NO 7
<211> LENGTH: 25
<212> TYPE: DNA
<213> ORGANISM: Artificial
<220> FEATURE:
<223> OTHER INFORMATION: Oligonucleotide primer 2 for amplifying a
      polynucleotide which encodes human 2',5'-oligoadenylate
      phosphodiesterase

<400> SEQUENCE: 7
tacttccttt tcagacttca attcc                                          25

<210> SEQ ID NO 8
<211> LENGTH: 22
<212> TYPE: DNA
<213> ORGANISM: Artificial
<220> FEATURE:
<223> OTHER INFORMATION: Oligonucleotide primer 3 for constructing a
      recombinant plasmid DNA which is available for functional
      expression of human 2',5'-oligoadenylate phosphodiesterase

<400> SEQUENCE: 8
tattatgtgg aggctcccag gc                                             22

<210> SEQ ID NO 9

```
<211> LENGTH: 26
<212> TYPE: DNA
<213> ORGANISM: Artificial
<220> FEATURE:
<223> OTHER INFORMATION: Oligonucelotide primer 4 for constructing a
      recombinant plasmid DNA which is available for functional
      expression of human 2',5'-oligoadenylate phosphodiesterase

<400> SEQUENCE: 9 tttccattt  aaatcacata caagtg                                        26

<210> SEQ ID NO 10
<211> LENGTH: 1939
<212> TYPE: DNA
<213> ORGANISM: Homo sapiens

<400> SEQUENCE: 10
ctcctcagct ccacctgaca gtaggccgct gatcggccgc gggtcttgtc gaccgctagg     60
ccaccaggtt catgtggagg ctcccaggcg cccgcgccgc gcttcgggtg atccggacgg    120
cggtggagaa gctgagctgg gctgaagcgg ggagccagac agcggcggga gcgatggagc    180
gcgctgtagt gcgctgcgta ccttcggaac ccaagctgag cctgtcattc gctttggctg    240
atggtagcca caagaacatg cagcgcgacc agagcgagcc gctgggtcga gtcctcagcc    300
gcatcgctac caatgcccta aagggtcacg ctaaggcggc cgccgccaag aagagcagga    360
agagccggcc gaatgctagc ggcggtgcgg cctgttcagg gccggggcct gagccggctg    420
tgttctgcga gcccgtggtg aagctgtact accgggaaga ggcagtggct gaggacgtgc    480
tcaacgtgga tgcctggcaa gacggcgcgg tgctgcagat cggcgatgtt aagtacaagg    540
tggagcgcaa cccgccccgcc ttcaccgaac tgcagttgcc gcgctacatc atggcccgcgt    600 tccctgtgtg ccccaaactc agcctcgaat tggggatcc cgccagctcc cttttccgct    660
ggtataagga agccaagccc ggagcggcgg agcccgaggt cggtgtcccc tcgtcattgt    720
ctccctcctc accttcttct tcttggactg agactgatgt ggaggagcgt gtctacaccc    780
cgtccaatgc cgacatcggg ctaaggctca agcttcactg caccccaggc gatgggcagc    840
gctttgggca cagccgggag ttggaaagtg tgtgtgtggt agaggctggg cctggcacct    900
gcacttttga ccaccggcat ctctacacga agaaggtgac tgaggacgct ctcatccgca    960
ctgtctctta caacatcctg gcagacacgt acgcgcagac tgagttctcg cgaacggttc   1020
tgtacccata ctgtgcccccc tacgccctgg agctcgacta ccgccagaac cttatccaga   1080
aggaactcac cggctacaac gccgatgtca tctgtttgca ggaggttgac cgcgcagtgt   1140
tttctgacag cttggtaccc gccctagagg ccttcgggct cgaggggtg tttcgaatca   1200 agcagcacga aggcctggcc actttctacc gaaagtctaa gttcagcctt cttagccagc   1260
atgacattcc attctacgaa gccctcgagt ccgacccact tcacaaagaa ctgctggaga   1320
aactagtttt gtacccatca gcgcaggaga aggtgctcca gagatcttct gttcttcagg   1380
tttcagttct tcagtctaca aaggactctt ctaaaaggat atgtgttgct aatacccatc   1440
tttactggca tcctaaaggt gggtatattc gccttcattca aatggcagta gccttggctc   1500
acataagaca tgtttcatgt gatctgtatc ctggcatacc agttatattt tgtggggact   1560
ttaatagtac accatcaaca ggaatgtatc atttttgtcat caatggcagc attccagagg   1620
atcatgaaga ctgggcttcc aatggggagg aggaaagatg caatatgtct cttacacatt   1680
tcttcaagct gaaaagtgct tgtgtgaac ctgcttacac aaattatgtt ggtgctttc   1740 atggatgtct agattacatt ttcattgact taaatgcttt agaggttgaa caggtgattc   1800
```
cattacctag tcatgaagaa gttaccaccc accaggcctt acctagtgtt tcccatccct    1860
ctgatcacat agcacttgta tgtgatttaa aatggaaata gatgtgtgtt taatggaatt    1920
gaagtctgaa aaggaagta                                                  1939

<210> SEQ ID NO 11
<211> LENGTH: 21
<212> TYPE: DNA
<213> ORGANISM: Artificial
<220> FEATURE:
<223> OTHER INFORMATION: siRNA 1 for inactivating a mRNA which encodes
      human 2',5'-oligoadenylate phosphodiesterase
<220> FEATURE:
<221> NAME/KEY: misc_feature
<222> LOCATION: (20)..(20)
<223> OTHER INFORMATION: The symbol "t" represents a deoxythymidine.
<220> FEATURE:
<221> NAME/KEY: misc_feature
<222> LOCATION: (21)..(21)
<223> OTHER INFORMATION: The symbol "t" represents a deoxythymidine.

<400> SEQUENCE: 11
guacaaggug gagcgcaact t                                               21

<210> SEQ ID NO 12
<211> LENGTH: 21
<212> TYPE: DNA
<213> ORGANISM: Artificial
<220> FEATURE:
<223> OTHER INFORMATION: siRNA 2 for inactivating a mRNA which encodes
      human 2',5'-oligoadenylate phosphodiesterase
<220> FEATURE:
<221> NAME/KEY: misc_feature
<222> LOCATION: (20)..(20)
<223> OTHER INFORMATION: The symbol "t" represents a deoxythymidine.
<220> FEATURE:
<221> NAME/KEY: misc_feature
<222> LOCATION: (21)..(21)
<223> OTHER INFORMATION: The symbol "t" represents a deoxythymidine.

<400> SEQUENCE: 12
guugcgcucc accuuguact t                                               21

<210> SEQ ID NO 13
<211> LENGTH: 21
<212> TYPE: DNA
<213> ORGANISM: Artificial
<220> FEATURE:
<223> OTHER INFORMATION: siRNA 3 for a control experiment
<220> FEATURE:
<221> NAME/KEY: misc_feature
<222> LOCATION: (20)..(20)
<223> OTHER INFORMATION: The symbol "t" represents a deoxythymidine.
<220> FEATURE:
<221> NAME/KEY: misc_feature
<222> LOCATION: (21)..(21)
<223> OTHER INFORMATION: The symbol "g" represents a deoxyguanosine.

<400> SEQUENCE: 13
ggugcucuca gagcucuuct g                                               21

<210> SEQ ID NO 14
<211> LENGTH: 21
<212> TYPE: DNA
<213> ORGANISM: Artificial
<220> FEATURE:
<223> OTHER INFORMATION: siRNA 4 for a control experiment
<220> FEATURE:
<221> NAME/KEY: misc_feature
<222> LOCATION: (20)..(20)

-continued

```
<223> OTHER INFORMATION: The symbol "t" represents a deoxythymidine.
<220> FEATURE:
<221> NAME/KEY: misc_feature
<222> LOCATION: (21)..(21)
<223> OTHER INFORMATION: The symbol "g" represents a deoxyguanosine.

<400> SEQUENCE: 14
gaagagcucu gagagcacct g                                            21
```

2', 5'-OLIGOADENYLATE PHOSPHODIESTERASE

CROSS-REFERENCE TO RELATED APPLICATIONS

This application is a continuation application of International application PCT/JP2003/011660 filed on Sep. 11, 2003, the entire contents of which are incorporated by reference herein.

BACKGROUND OF THE INVENTION

1. Field of the Invention

The present invention relates to a novel polypeptide, a polynucleotide coding for said polypeptide, a recombinant plasmid DNA into which said polynucleotide has been inserted, a host cell transformed with said recombinant plasmid DNA, a process for preparing said polypeptide or polynucleotide comprising isolating the polypeptide or polynucleotide from a culture of said host cells, a process for screening for a substance that modulates the activity of said polypeptide and a kit for said screening, a process for screening for a substance that modulates the expression of said polypeptide or polynucleotide and a kit for said screening, a process for screening for a substance that binds to said polypeptide and a kit for said screening, a process for detecting the activity of said polypeptide and a kit for said detecting, a process for detecting the expression of said polypeptide or polynucleotide and a kit for said detecting, an antibody that specifically binds to said polypeptide, an active fragment thereof, a chimeric antibody thereof, and a humanized antibody thereof, a pharmaceutical composition consisting of said human antibody or a single strand antibody thereof, and a pharmaceutical composition consisting of said polypeptide.

2. Background Art

2',5'-oligoadenylate (hereinafter referred to as "2-5A") is an oligoribonucleotide in which two or more adenosines have been phosphodiester-bound between their 2'- and 5'-positions, and a triphosphate has been bound at the 5'-position of the 5'-terminal adenosine. 2-5A functions as a modulator molecule within a cell, and the system for control of cellular or viral proliferation mediated via RNA degradation by 2-5A is called the 2-5A system (M. R. Player and P. F. Torrence, "The 2-5A system: modulation of viral and cellular processes through acceleration of RNA degradation," Pharmacology & Therapeutics, published in Great Britain in 1998, vol. 78, pp. 55-113).

The 2-5A system involves three enzymes. The first 2-5A synthetase, which is a 2-5A synthesizing enzyme is activated by double-stranded RNA; 2-5A is synthesized from ATP by 2-5A synthetase. Secondly 2',5'-oligoadenylate phosphodiesterase (2',5'-oligoadenylate phosphodiesterase; hereinafter referred to as "2'-PDE"), which is an enzyme that degrades 2-5A into AMP and ATP. Thirdly RNase L, which is a 2-5A dependent ribonuclease activated by 2-5A. Activated RNase L degrades single stranded RNA, such as mRNA, and as a result, inhibits protein syntheses and cell proliferation. It is believed that in the 2-5A system, the amount of 2-5A present is important, and that the activity of RNase L is modulated by the balance between the synthesis and degradation of 2-5A.

The 2-5A system has been well investigated as one of the mechanisms of the anti-viral activity of interferon. Interferon is a cytokine which induces 2-5A synthetase in a manner mediated by the cell membrane. Since many viruses have a double-stranded RNA form during the process of infection and proliferation, and 2-5A synthetase is activated by double-stranded RNA, 2-5A synthetase is preferentially activated in a cell infected with a virus. It is believed that the 2-5A level in a cell that has been infected with a virus is elevated by activated 2-5A synthetase, this is accompanied by the activation of RNase L, and inhibition of protein synthesis in the virus-infected cell, leading to inhibition of viral proliferation. Direct viral RNA degradation by activated RNase L and the resulting inhibition of viral proliferation are also known to occur.

Interferon is a multi-functional molecule that has, in addition to anti-viral action, various biological activities such as a cell proliferation suppression effect, an anti-tumor effect, activation of macrophage, enhancement of the activity of natural killer cells, immune response modulation action, a negative feedback action on osteoclast differentiation, modulation of the induction of differentiation etc. (Kohei Miyazono and Kazuo Sugamura eds., "Bio Science Yogo Library, Cytokines and Growth Factors," published by Youdosha Co., Ltd. Japan, 1998, pp. 178-185; H. Takayanagi et al., "RANKL maintains bone homeostasis through c-Fos-dependent induction of interferon-β," Nature, published in Great Britain in 2002, vol. 416, pp. 744-749).

Mutations in the RNase L gene were observed among prostate cancer-developing families (J. Carpten et al., "Germ line mutations in the ribonuclease L gene in families showing linkage with HPC1," Nature Genetics, published in the United States in 2002, vol. 30, pp. 181-184). Further, it has been suggested that 2-5A synthetase is induced by nerve growth factor (M. Saarma et al., "Nerve growth factor induces changes in (2'-5') oligo(A) synthetase and 2'-phosphodiesterase activities during differentiation of PC12 pheochromocytoma cells," Experimental Cell Research, published in Sweden in 1986, vol. 166, pp. 229-236), and thus the 2-5A system may be involved in expression of functions of cytokines other than interferon. In addition, it has been suggested that in the process of osteoclast differentiation, interferon inhibits differentiation by a negative feedback mechanism (H. Takayanagi et al., "RANKL maintains bone homeostasis through c-Fos-dependent induction of interferon-β," Nature, published in Great Britain in 2002, vol. 416, pp. 744-749).

A 2'-PDE inhibitory substance may exert anti-viral, anti-tumor, and immuno-activating actions via the 2-5A system by elevating 2-5A levels in vivo or in a cell. However, to date, studies on 2'-PDE have been limited. Polypeptides having 2'-PDE activity purified from mouse and bovine sources are known. Polypeptides purified from two types of cell derived from mice had a molecular weight of 35,000 determined by SDS-polyacrylamide gel electrophoresis and an apparent molecular weight of 40,000 determined by gel filtration chromatography; these polypeptides hydrolysed 2',5'-oligoadenylate to an extent similar to or greater than the extent to which they hydrolysed 3',5'-oligoadenylate; and had the activity of degrading the C-C-A terminus of tRNA (A. Schmidt et al., "An interferon-induced phosphodiesterase degrading (2'-5') oligoadenylate and the C-C-A terminus of tRNA," Proceedings of National Academy of Science, U.S.A, published in the United States in 1979, vol. 76, no. 10, pp. 4788-4792). The polypeptide purified from a bovine source had a molecular weight of 65,000 determined by SDS-polyacrylamide gel electrophoresis, an apparent molecular weight of 56,000±11,000 determined by gel filtration chromatography and an isoelectric point of around pH 8.3, but its ability to hydrolyse 2',5'-oligoadenylate was about one hundredth of its ability to hydrolyse 3',5'-oligoadenylate (W. G. Hearl, Purification and Characterization of a 2'-Phosphodiesterase from Bovine Spleen," Journal of Biological Chemistry, published in the United States in 1987, vol. 262, no. 17, pp. 8377-8382). Thus, it was not clearly established that the polypeptide was a 2'-PDE.

SUMMARY OF THE INVENTION

The present invention provides a polypeptide, a polynucleotide, a process for screening using them, and a kit for screening, which is useful for screening for a substance that can activate a 2',5'-oligoadenylate (hereinafter referred to as "2'-5'A") system in vivo or in a cell by elevating the 2-5A level in the cell or in vivo.

The present inventors, as a result of extensive investigation performed on a probe target molecule for a substance that activates or enhances the 2-5A system, found a novel polypeptide having 2',5'-oligoadenylate phosphodiesterase (hereinafter referred to as "2'-PDE") activity and a novel polynucleotide coding therefor.

Accordingly, the present invention provides:

(1)

a polynucleotide selected from the group consisting of the following [i] to [iv]:

[i] a polynucleotide coding for a polypeptide comprising the amino acid sequence as set forth in Sequence ID No. 2 of the Sequence Listing;

[ii] a polynucleotide comprising the nucleotide sequence as set forth in Sequence ID No. 1 of the Sequence Listing;

[iii] a polynucleotide that hybridizes with a polynucleotide comprising a nucleotide sequence entirely complementary to the nucleotide sequence as set forth in Sequence ID No. 1 of the Sequence Listing under stringent conditions, and that codes for a polypeptide having 2',5'-oligoadenylate phosphodiesterase activity; and,

[iv] the shorter of the polynucleotides between the two restriction enzyme EcoR1 recognition sites of the recombinant plasmid DNA carried by the transformant E. coli strain pCR-Blunt II TOPO-F6-2/22 SANK 71002 (FERM BP-8142); and (2)

a polynucleotide selected from the group consisting of the following [i] to [vi]:

[i] a polynucleotide coding for a polypeptide consisting of an amino acid sequence in which the methionine at the 1st position, or two or more contiguous amino acids, including the methionine at the 1st position, of the amino acids from the methionine at the 1st position to the alanine at the 34th position in the amino acid sequence as set forth in Sequence ID No. 2 of the Sequence Listing have been deleted;

[ii] a polynucleotide consisting of a nucleotide sequence in which the adenosine at the 1st position and the two 3'-adjacent nucleotides (5'-terminal trimer), or 3n (n is an integer from 1 to 33) contiguous nucleotides including the 5'-terminal trimer, of the nucleotides from the adenosine at the 1st position to the guanosine at the 102nd position in the nucleotide sequence as set forth in Sequence ID No. 1 of the Sequence Listing have been deleted;

[iii] a polynucleotide coding for a polypeptide consisting of the methionine at the 35th position to the lysine at the 609th position of the amino acid sequence as set forth in Sequence ID No. 2 of the Sequence Listing;

[iv] a polynucleotide consisting of the adenosine at the 103rd position to the 1827th adenosine in the nucleotide sequence as set forth in Sequence ID No. 1 of the Sequence Listing;

[v] a polynucleotide consisting of the adenosine at the 103rd position to the guanosine at the 1830th position in the nucleotide sequence as set forth in Sequence ID No. 1 of the Sequence Listing; and

[vi] a polynucleotide as defined in any of [i] to [v] comprising a methionine codon that has been added to the 5'-terminus.

Further, the present invention provides:

(3)

a recombinant plasmid DNA into which a polynucleotide as defined in (1) or (2) has been inserted;

(4)

a recombinant plasmid DNA as defined in (3) above, characterized in that it is an expression plasmid DNA; and (5)

the recombinant plasmid DNA carried by the transformant E. coli strain pCR-Blunt II TOPO-F6-2/22 SANK 71002 (FERM BP-8142).

Further, the present invention includes:

(6)

a host cell transformed with a plasmid as defined in any of (3) to (5) above;

(7)

a host cell as defined in (6), that is a cell derived from a mammal;

(8)

a host cell as defined in (7), that is a CHO cell, a dihydrofolate dehydrogenase-deficient strain of a CHO cell, or a COS cell; and (9)

a host cell as defined in (6), that is the transformant E. coli strain pCR-Blunt II TOPO-F6-2/22 SANK 71002 (FERM BP-8142).

Further, the present invention provides:

(10)

a process for producing a polypeptide having a 2',5'-oligoadenylate phosphodiesterase activity, comprising the following steps [i] and [ii]:

[i] culturing a host cell as defined in any one of (6) to (9) above; and

[ii] harvesting polypeptide having 2',5'-oligoadenylate phosphodiesterase activity from the culture.

Further, the present invention provides:

(11)

a polypeptide selected from the group consisting of the following [i] to [v]:

[i] a polypeptide comprising the amino acid sequence as defined in Sequence ID No. 2 of the Sequence Listing;

[ii] a polypeptide comprising an amino acid sequence in which one or several amino acids have been added, deleted, substituted or inserted in the amino acid sequence as set forth in Sequence ID No. 2 of the Sequence Listing, and having 2',5'-oligoadenylate phosphodiesterase activity;

[iii] a polypeptide comprising an amino acid sequence with 90% or more homology to the amino acid sequence as defined in Sequence ID No. 2 of the Sequence Listing, and having 2',5'-oligoadenylate phosphodiesterase activity;

[iv] the polypeptide coded by the shorter of the polynucleotides between the two restriction enzyme EcoR1 recognition sites of the recombinant plasmid DNA carried by the transformant E. coli strain pCR-Blunt II TOPO-F6-2/22 SANK 71002 (FERM BP-8142); and

[v] a polypeptide coded by a polynucleotide comprising the nucleotide sequence as set forth in Sequence ID No. 1 of the Sequence Listing;

(12)

a polypeptide selected from the group consisting of the following [i] to [vi]:

[i] a polypeptide consisting of an amino acid sequence in which the methionine at the 1st position, or two or more contiguous amino acids including the methionine, of the amino acids from the methionine at the 1st position to the alanine at the 34th position in the amino acid sequence as set forth in Sequence ID No. 2 in the Sequence Listing have been deleted;

[ii] a polypeptide coded by a polynucleotide consisting of a nucleotide sequence in which the adenosine at the 1st position and the two 3' adjacent nucleotides (5'-terminal trimer), or 3n (n is an integer from 1 to 33) contiguous nucleotides, of the nucleotides from the adenosine at the 1st position to the guanosine at the 102nd position in the nucleotide sequence as set forth in Sequence ID No. 1 of the Sequence Listing have been deleted;

[iii] the polypeptide consisting of the amino acid sequence from the methionine at the 35th position to the lysine at the 609th position of the amino acid sequence as set forth in Sequence ID No. 2 of the Sequence Listing;

[iv] the polypeptide coded by the polynucleotide consisting of the nucleotide sequence from the adenosine at the 103rd position to the 1827th adenosine of the nucleotide sequence as set forth in Sequence ID No. 1 of the Sequence Listing;

[v] the polypeptide coded by the polynucleotide consisting of the nucleotide sequence from the adenosine at the 103rd position to the guanosine at the 1830th position of the nucleotide sequence as set forth in Sequence ID No. 1 of the Sequence Listing; and

[vi] a polypeptide as defined in any of [i] to [v], which comprises a methionine that has been added to the amino terminus;

(13)

a polypeptide as defined in (11) or (12) above, obtainable by a process as defined in (10) above; and (14)

a polypeptide as defined in any one of (11) to (13) above, characterized in that the activity of the polypeptide in hydrolyzing 2',5'-oligoadenylate is equivalent to or greater than the activity of the polypeptide in hydrolyzing 3',5'-oligoadenylate.

Further, (15)

a polynucleotide coding for a polypeptide as defined in (11) or (12) is also included as being a polynucleotide of the present invention.

Screening process of the present invention include:

(16)

a process for screening for a 2',5'-oligoadenylate phosphodiesterase activity inhibitor substance, comprising the following steps of [i] to [iii]:

[i] contacting, in the presence or absence of a specimen, a polypeptide as defined in any of (11) to (14) above, an active fragment thereof or an active derivative thereof, with a nucleotide substrate comprising an adenylyl(2'-5')adenosine as a part of its structure;

[ii] measuring the amount of hydrolysis of the nucleotide substrate; and

[iii] judging the specimen as being positive, when the amount of hydrolysis in the presence of said specimen is lower than that in the absence of the specimen;

(17)

a process for screening for a 2',5'-oligoadenylate phosphodiesterase activity inhibitor substance, comprising the following steps of [i] to [iii]:

[i] contacting, in the presence or absence of a specimen, a host cell as defined in any one of (6) to (9) above with a nucleotide substrate comprising an adenylyl(2'-5')adenosine as a part of its structure;

[ii] measuring the amount of hydrolysis of the nucleotide substrate; and

[iii] judging the specimen as being positive, when the amount of hydrolysis in the presence of the specimen is lower than that in the absence of the specimen;

(18)

a process for screening for a 2',5'-oligoadenylate phosphodiesterase expression suppressor substance, comprising the following steps of [i] to [iii]:

[i] incubating a host cell as defined in any one of (6) to (9) above, in the presence or absence of a specimen;

[ii] measuring the amount of transcription of a polynucleotide as defined in (1), (2) or (15) above, or the amount of translation of a polypeptide as defined in any one of (11) to (14) above, in the host cell or in the extracellular fluid; and

[iii] judging the specimen as being positive, when the amount of transcription or the amount of translation in the presence of the specimen is lower than that in the absence of the specimen;

(19)

a process for screening for a 2',5'-oligoadenylate phosphodiesterase expression suppressor substance, comprising the following steps of [i] to [iii]:

[i] incubating, in the presence or absence of a specimen, a host cell that endogenously carries a polynucleotide as defined in (1), (2) or (15) above;

[ii] measuring the amount of transcription of a polynucleotide as defined in (1), (2) or (15) above, or the amount of translation of a polypeptide as defined in any one of (11) to (14) above, in the cell or in the extracellular fluid; and

[iii] judging the specimen as being positive, when the amount of transcription or the amount of translation in the presence of the specimen is lower than that in the absence of the specimen;

(20)

a process for screening for a 2-5A system activator substance, comprising the following steps of [i] to [iii]:

[i] contacting, in the presence or absence of a specimen, a polypeptide as defined in any of (11) to (14) above, an active fragment thereof, or an active derivative thereof, with a nucleotide substrate comprising an adenylyl(2'-5') adenosine as a part of its structure;

[ii] measuring the amount of hydrolysis of the nucleotide substrate; and

[iii] judging the specimen as being positive, when the amount of hydrolysis in the presence of the specimen is less than that in the absence of the specimen;

(21)

a process for screening for a 2-5A system activator substance, comprising the following steps of [i] to [iii]:

[i] contacting, in the presence or absence of a specimen, a host cell as defined in any of (6) to (9) above, with a nucleotide substrate comprising an adenylyl(2'-5')adenosine as a part of its structure;

[ii] measuring the amount of hydrolysis of the nucleotide substrate; and

[iii] judging the specimen as being positive, when the amount of hydrolysis in the presence of the specimen is less than that in the absence of the specimen;

(22)

a process for screening for a 2-5A system activator substance, comprising the following steps of [i] through to [iii]:

[i] incubating a host cell as defined in any of (6) to (9) above in the presence or absence of a specimen;

[ii] measuring the amount of transcription of a polynucleotide as defined in (1), (2) or (15) above, or the amount of translation of a polypeptide as defined in any of (11) to (14) above in the host cell or in the extracellular fluid; and

[iii] judging the specimen as being positive, when the amount of transcription or the amount of translation in the presence of the specimen is less than that in the absence of the specimen;

(23)

a process for screening for a 2-5A system activator substance, comprising the following steps of [i] to [iii]:

[i] incubating, in the presence or absence of a specimen, a cell that endogenously carries a polynucleotide as defined in (1), (2) or (15) above;

[ii] measuring the amount of transcription of a polynucleotide as defined in (1), (2) or (15) above, or the amount of translation of a polypeptide as defined in any one of (11) to (14) above, in the cell or the extracellular fluid; and

[iii] judging the specimen as being positive, when the amount of transcription or the amount of translation in the presence of the specimen is less than that in the absence of the specimen;

(24)

a process for screening for a 2-5A system activator substance, comprising the following steps of [i] to [iii]:

[i] incubating a host cell as defined in any one of (6) to (9) above in the presence or absence of a specimen;

[ii] measuring the amount of 2',5'-oligoadenylate or the amount of RNA degradation by ribonuclease L (hereinafter referred to as "RNase L") in the host cell or in the extracellular fluid;

[iii] judging the specimen as being positive, when the amount of 2',5'-oligoadenylate or the amount of RNA degradation by RNase L in the presence of the specimen is greater than that in the absence of the specimen;

(25)

a process for screening for a 2-5A system activator substance, comprising the following steps of [i] to [iii]:

[i] incubating a cell that endogenously carries a polynucleotide as defined in (1), (2) or (15) above in the presence or absence of a specimen;

[ii] measuring the amount of 2',5'-oligoadenylate or the amount of RNA degradation by ribonuclease L (hereinafter referred to as "RNase L") in the host cell or the extracellular fluid;

[iii] judging the specimen as being positive, when the amount of 2',5'-oligoadenylate or the amount of RNA degradation by RNase L in the presence of the specimen is greater than that in the absence of the specimen; and (26)

a process as defined in any one of (17) to (19) or (21) to (25) above, characterized in that the host cell or the cell is incubated in the presence and/or absence of interferon in step [i].

The present invention provides:

(27)

a kit for screening for a 2',5'-oligoadenylate phosphodiesterase activity inhibitor substance, a kit for screening for a 2',5'-oligoadenylate phosphodiesterase expression suppressor substance, a kit for screening for a 2',5'-oligoadenylate phosphodiesterase binding substance, or a kit for screening for a 2-5A system activator substance, comprising at least one of the following [a] to [d]:

[a] a polynucleotide as defined in (1), (2) or (15), or a fragment thereof;

[b] an oligonucleotide comprising at least 10 bases, that has a part of the nucleotide sequence of a polynucleotide as defined in [a] or a nucleotide sequence entirely complementary thereto, and that hybridzes with the sense strand or anti-sense strand of a polynucleotide as defined in [a];

[c] an isolated antibody that specifically binds to a polypeptide as defined in any one of (11) to (14) above, or an active fragment thereof;

[d] an insoluble carrier to which a moiety selected from the group consisting of a polynucleotide as defined in [a] or an active fragment thereof, an oligonucleotide as defined in [b], and an antibody as defined in [c] or an active fragment thereof, has been bound directly or via a spacer; and (28)

a kit as defined in (27), comprising interferon.

Further, the present invention provides:

(29)

a process comprising the following steps of [i] and [ii] for detecting the 2',5'-oligoadenylate phosphodiesterase activity of a polypeptide as defined in any of claims 11 to 14 included in an analyte sample:

[i] contacting a specimen with a nucleotide substrate comprising an adenylyl(2'-5')adenosine as a part of its structure; and

[ii] measuring the amount of hydrolysis of the nucleotide substrate; and (30)

a process for detecting expression of 2',5'-oligoadenylate phosphodiesterase, comprising the step of measuring the amount of transcription of a polynucleotide as defined in (1), (2) or (15) above, or the amount of translation of a polypeptide as defined in any one of (11) to (14) above in an analyte sample.

Further, in the present invention there is included.

(31)

a process for assessing the degree of 2-5A system activation, comprising the following steps of [i] and [ii]:

[i] measuring the amount of transcription of a polynucleotide as defined in (1), (2) or (15) above, or the amount of translation of a polypeptide as defined in any of (11) to (14) above, in samples derived from a subject human or a subject mammal, and a healthy human or a healthy mammal; and

[ii] judging that the subject human or the subject mammal has an activated 2-5A system, when the amount of transcription or the amount of translation in the sample derived from the subject human or the subject mammal is less than that in the sample from the healthy human or the healthy mammal.

Further, the present invention provides:

(32)

a kit for detecting 2',5'-oligoadenylate phosphodiesterase activity, a kit for detecting expression of 2',5'-oligoadenylate phosphodiesterase, or a kit for assessing the degree of activation of the 2-5A system, comprising at least one of the following [a] to [d]:

[a] a polynucleotide as defined in (1), (2) or (15) above, or an active fragment thereof;

[b] an oligonucleotide comprising at least 10 bases, that has a part of the nucleotide sequence of a polynucleotide as defined in [a], or a nucleotide sequence entirely complementary thereto, and that hybridises with the sense strand or anti-sense strand of a polynucleotide as defined in [a];

[c] an isolated antibody that specifically binds to a polypeptide as defined in any of (11) to (14) above, or an active fragment thereof; and

[d] an insoluble carrier to which a moiety selected from the group consisting of a polynucleotide as defined in [a]or a fragment thereof, an oligonucleotide as defined in [b], and an antibody as defined in [c] or an active fragment thereof, has been bound directly or via a spacer; and

(33)
a kit as defined in (32), comprising interferon.
The present invention provides:

(34)
an antibody that specifically binds to a polypeptide as defined in any of (11) to (14) above, or an active fragment thereof. Additionally, the present invention includes:

(35)
a pharmaceutical composition comprising an antibody or an active fragment thereof as defined in (34) above;

(36)
a 2',5'-oligoadenylate phosphodiesterase inhibitory agent comprising an antibody or an active fragment thereof as defined in (34) above;

(37)
a 2-5A system activating agent comprising, as an active ingredient, an antibody or an active fragment thereof as defined in (34) above;

(38)
a pharmaceutical composition comprising a polypeptide as defined in any of (11) to (14) above;

(39)
a 2-5A system inactivating agent containing as an active ingredient a polypeptide as defined in any of (11) to (14) above;

(40)
a pharmaceutical composition comprising a polynucleotide as defined in (1), (2) or (15) above;

(41)
a 2-5A system inactivating agent containing as an active ingredient a polynucleotide as defined in (1), (2) or (15) above; and

(42)
a pharmaceutical composition as defined in (35), (38) or (40) above, comprising interferon.
Further, the present invention provides:

(43)
a nucleotide sequence as defined in the following subsections [i] or [ii], that suppresses transcription of a polynucleotide as defined in (1), (2) or (15) above:

[i] at least 10 contiguous nucleotides existing in a polynucleotide consisting of the nucleotide sequence as defined in Sequence ID No. 1 of the Sequence Listing; or

[ii] a nucleotide sequence entirely complementary to at least 10 contiguous nucleotides existing in a polynucleotide consisting of the nucleotide sequence as defined in Sequence ID No. 1 of the Sequence Listing; and

(44)
a small interfering RNA that inactivates a polynucleotide as defined in (1), (2) or (15) above, constructed by hybridizing nucleotides as defined in the following [i] and [ii]:

[i] contiguous 10 to 30 nucleotides existing in a polynucleotide consisting of the nucleotide sequence as defined in Sequence ID No. 1 of the Sequence Listing; and

[ii] nucleotides entirely complementary to contiguous 10 to 30 nucleotides existing in a polynucleotide consisting of the nucleotide sequence as defined in Sequence ID No. 1 of the Sequence Listing.

Further included within the scope of the present invention are:

(45)
a process for increasing the amount of 2',5'-phosphoadenylate contained in a cell, by, in the cell, reducing the amount of transcription of a polynucleotide as defined in (1), (2) or (15) above, reducing the amount of translation of a polypeptide as defined in any of (11) to (14) above, or inhibiting the 2',5'-oligoadenylate phosphodiesterase activity of a polypeptide as defined in any of (11) to (14) above;

(46)
a process for activating ribonuclease L within a cell, by, in the cell, reducing the amount of transcription of a polynucleotide as defined in (1), (2) or (15) above, reducing the amount of translation of a polypeptide as defined in any of (11) to (14) above, or inhibiting the 2',5'-oligoadenylate phosphodiesterase activity of a polypeptide as defined in any of (11) to (14) above;

(47)
a process for activating the 2-5A system within a cell, by, in the cell, reducing the amount of transcription of a polynucleotide as defined in (1), (2) or (15) above, reducing the amount of translation of a polypeptide as defined in any one of (11) to (14), or inhibiting the 2',5'-oligoadenylate phosphodiesterase activity of a polypeptide as defined in any of (11) to (14) above;

(48)
a process as defined in any one of (45) to (47), characterized by introducing into the cell any one of the following [i] to [iii]:

[i] an antibody or an active fragment thereof as defined in (34);

[ii] a nucleotide as defined in (43);

[iii] a small interfering RNA as defined in (44);

(49)
a process as defined in any one of (45) to (48) above, characterized by administering interferon before, simultaneously with, or after reducing the amount of transcription of a polynucleotide as defined in (1), (2) or (15) above, reducing the amount of translation of a polypeptide as defined in any one of (11) to (14) above, or inhibiting the 2',5'-oligoadenylate phosphodiesterase activity of a polypeptide; as defined in any of (11) to (14) above and

(50)
a process as defined in any one of (45) to (47) above, characterized by, in the genomic DNA contained in the cell, deleting a potion or the entirety of a polynucleotide as defined in (1), (2) or (15) above, or mutating the polynucleotide so that the 2',5'-phosphodiesterase activity of the polypeptide coded by the polynucleotide is partially or entirely lost.

BRIEF DESCRIPTION OF THE DRAWINGS

FIG. 1 (upper panel): a figure that represents the result of subjecting the fractions obtained by anion exchange chromatography as described in Example 1 to SDS-polyacrylamide gel electrophoresis.

FIG. 1 (lower panel): a figure that represents the result of detecting the 2'-PDE activity of the fractions obtained by the anion exchange chromatography as described in Example 1.

FIG. 2 (lower panel): a graph that represents the result of detecting the 2'-PDE activity of the fractions obtained by gel filtration column chromatography as described in Example 1.

FIG. 5 (upper panel: A): a graph representing the activity of the recombinant human 2'-PDE with adenylyl(2'-5')adenosine as the substrate. Adenylyl(2'-5')adenosine was hydrolyzed by an extract from host cells into which DNA coding for human 2'-PDE had been introduced (pEF6/KUBO#002/11-1). Adenylyl(2'-5')adenosine was not hydrolysed by an extract from host cells into which a negative control DNA had been introduced (pEF6/V5-His-TOPO/LacZ), nor by an extract from host cells into which no foreign DNA had been introduced (-DNA).

FIG. 5 (lower panel: B): a graph representing the activity of the recombinant human 2'-PDE with adenylyl(3'-5')adenosine as the substrate. Adenylyl(3'-5')adenosine was hydrolyzed by an extract from host cells into which DNA coding for human 2'-PDE had been introduced (pEF6/KUBO#002/11-1). Adenylyl(3'-5')adenosine was slightly hydrolyzed by an extract from host cells into which a negative control DNA had been introduced (pEF6/V5-His-TOPO/LacZ) and an extract from host cells into which no foreign DNA had been introduced (-DNA).

FIG. 6 (lower panel: B): a graph representing the relative amount of transcription of human 2'-PDE. It was transcribed at a high level in melanocytes.

FIG. 7 (lower panel: B): a table in which the substrate selectivity of human 2'-PDE for various oligoadenylates was compared with known enzymes. "A2'pA," "A3'pA," "A2'pA2'pA," "A3'pA3'pA," "pA2'pA2'pA," and "pA3'pA3'pA" indicate adenylyl(2'-5')adenosine, adenylyl(3'-5')adenosine, adenylyl(2'-5')adenylyl(2'-5')adenosine, adenylyl(3'-5')adenylyl(3'-5')adenosine, 5'-phosphoadenylyl(2'-5')adenylyl(2'-5')adenosine, and 5'-phosphoadenylyl(3'-5')adenylyl(3'-5')adenosine, respectively. [1] The enzyme activity is a relative value calculated by defining the activity when A2'pA was the substrate as being 1. [2] Literature value (Schmidt, A., et al., Proc. Natl. Acad. Sci. USA, 76, pp. 4788-4792 (1979)). [3] Literature value (Johnston, M. I., et al., J. Biol. Chem., 262, pp. 8377-8382 (1986)) FIG. 8 (upper panel: A): a graph indicating that A-74528 inhibits human 2'-PDE in a concentration-dependent manner.

FIG. 8 (lower panel: B): a graph representing viral replication suppression activity by various concentrations of A-74528 in the presence or absence of interferon (IFN). The concentrations of A-74528 are 0 μg/ml for the filled column, 25 μg/ml for the open column, 50 μg/ml for the dotted column, and 100 μg/ml for the striped column.

FIG. 10 (central left panel: B): a graph showing that interferon-α (INF-α) suppressed the proliferation of PC-3 cells (♦) in a concentration-dependent manner, but that the suppressive effect was attenuated in #6 strain (■) and #10 strain (□) expressing 2'-PDE and that the degree of attenuation was correlated with the level of 2'-PDE expression.

FIG. 10 (central right panel: C): a graph representing that interferon-γ (INF-γ) suppressed the proliferation of PC-3 cells (♦) in a concentration-dependent manner, but that the suppressive effect was attenuated in #6 strain (■) and #10 strain (□) expressing 2'-PDE and that the degree of attenuation was correlated with the level of 2'-PDE expression.

FIG. 10 (lower panel: D): a graph representing that dsRNA suppressed the proliferation of PC-3 cells (♦) in a concentration-dependent manner, but that the suppressive effect was attenuated in #6 strain (■) and #10 strain (□) expressing 2'-PDE and that the degree of attenuation was correlated with the level of 2'-PDE expression.

FIG. 12 (upper panel: A): a figure showing mapping of the amino acid sequence as described in Sequence ID No. 2 of the Sequence Listing by combining the four mass spectrum data obtained by enzyme digestion of a band corresponding to the short chain form of 2'-PDE (35-609) and by using database search software (Mascot: manufactured by Matrix Science Ltd.).

FIG. 12 (lower panel: B): a figure representing the tandem mass spectrometry spectrum with the monoisotopic mass 451.75 as the precursor ion among the peptides obtained by enzyme digestion of a band corresponding to the short chain form of 2'-PDE (35-609). The oligopeptide having at its amino-terminus a methionine at the 35th position in the amino acid sequence as set forth in Sequence ID No. 2 of the Sequence Listing and with acetylation at the amino-terminus, was well ascribed by MS/MS spectrum.

DETAILED DESCRIPTION OF THE INVENTION

Figure 2:
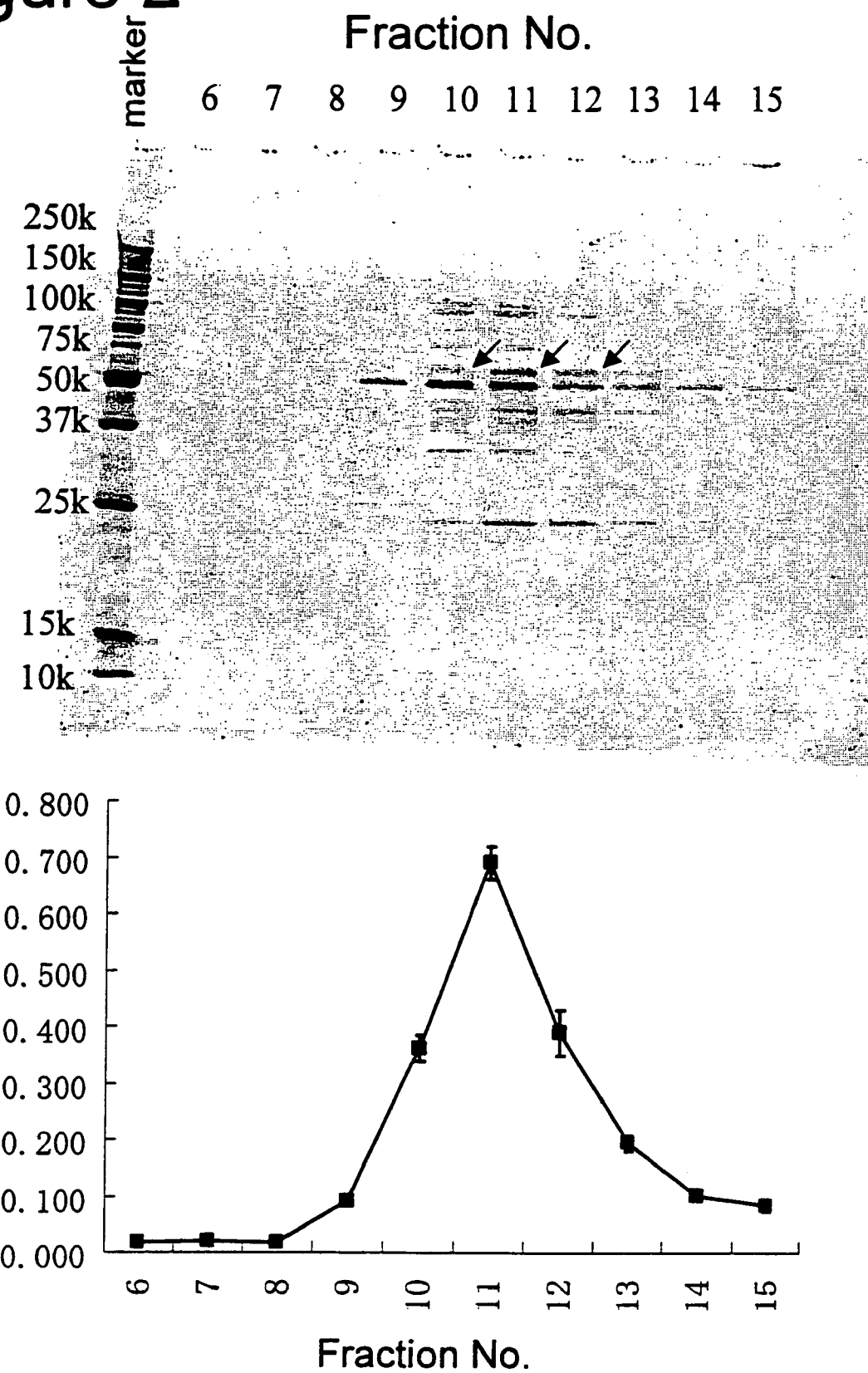
FIG. 2 (upper panel): a figure that represents the result of subjecting the fractions obtained by gel filtration column chromatography as described in Example 1 to SDS-polyacrylamide gel electrophoresis.

In the present invention, a "polypeptide" means a polypeptide having 2'-PDE activity. These peptides are exemplified by the following [P1] to [P8]. Preferably it is a polypeptide as set forth in any one of [P1] to [P6], and more preferably a polypeptide as set forth in [P1], [P4], [P5] or [P6]:

[P1] a polypeptide comprising the amino acid sequence as set forth in Sequence ID No. 2 of the Sequence Listing;
[P2] a polypeptide comprising an amino acid sequence in which one or several (two or more, up to ten) amino acids have been added, deleted, substituted or inserted in the amino acid sequence as set forth in Sequence ID No. 2 of the Sequence Listing, and having 2'-PDE activity;
[P3] a polypeptide comprising an amino acid sequence that is 80% or more, preferably 90% or more, more preferably 95% or more identical to the amino acid sequence as described in Sequence ID No. 2 of the Sequence Listing;
[P4] a polypeptide coded by the polynucleotide inserted between the two restriction enzyme EcoR1 recognition sites of the recombinant plasmid DNA carried by the transformant *E. coli* pCR-Blunt II TOPO-F6-2/22 SANK 71002 (FERM BP-8142);
[P5] a polypeptide coded by a polynucleotide comprising the nucleotide sequence as set forth in Sequence ID No. 1 of the Sequence Listing;
[P6] a fragment of a polypeptide as described in any of the above [P1] to [P5], having 2'-PDE activity. In the present invention, said fragment is termed as an active fragment;
[P7] a polypeptide homo-dimer or homo-multimer of a trimer or more, or a polypeptide hetero-dimer or hetero-multimer of a trimer or more, containing two or more of the polypeptide as described in any of the above [P1] to [P6] or fragments thereof, and which are bound each other or one another either directly or indirectly, e.g. via a spacer, and which has 2'-PDE activity. In the present invention, these are designated as being "multimers" of polypeptides;
[P8] a polypeptide as described in any of the above [P1] to [P7], a fragment or multimer thereof, to which a tag of a water-soluble polymer, such as polyethylene glycol; a polysaccharide, such as dextran sulfate; a single sugar, an Fc region of an immunoglobulin, or a histidine oligomer has been chemically or non-chemically attached. In the present invention, these are designated as being "active derivatives" of polypeptides.

More specific examples of [P6] include polypeptides selected from the group consisting of the following [P6i] to [P6v]:

[P6i] a polypeptide consisting of an amino acid sequence in which a methionine at the 1st position, or two or more contiguous amino acids including the methionine, of the amino acids from the methionine at the 1st position to the alanine at the 34th position in the amino acid sequence as set forth in Sequence ID No. 2 of the Sequence Listing have been deleted;
[P6ii] a polypeptide coded by a polynucleotide consisting of a nucleotide sequence in which the adenosine at the 1st position and the two 3' adjacent nucleotides (5'-terminal trimer), or 3n (n is an integer from 1 to 33) contiguous nucleotides including the 5'-terminal trimer, of the nucleotides from the adenosine at the 1st position to the guanosine at the 102nd position in the nucleotide sequence as set forth in Sequence ID No. 1 of the Sequence Listing have been deleted;
[P6iii] a polypeptide consisting of the methionine at the 35th position to the lysine at the 609th position of the amino acid sequence as set forth in Sequence ID No. 2 of the Sequence Listing;
[P6iv] a polypeptide coded by a polynucleotide consisting of the adenosine at the 103rd position to the adenosine at the 1827th position of the nucleotide sequence as set forth in Sequence ID No. 1 of the Sequence Listing; and
[P6v] a polypeptide coded by a polynucleotide consisting of the adenosine at the 103rd position to the guanosine at the 1830th position of the nucleotide sequence as set forth in Sequence ID No. 1 of the Sequence Listing.

In the present invention, a polypeptide as described in any one of [P6i] to [P6v] is referred to as a "short chain form of 2'-PDE," and, inter alia, a polypeptide as described in any of [P6iii] to [P6v] is referred to as a "short chain form of 2'-PDE (35-609)." The "2'-PDE" of the present invention encompasses the short chain form of 2'-PDE as well as the short chain form of 2'-PDE (35-609).

In the present invention, a "polynucleotide" is a polynucleotide coding for a polypeptide of the present invention or a fragment thereof, and may be any of a genomic DNA fragment, an RNA synthesized by RNA polymerase with genomic DNA as the template (messenger RNA), and a complementary DNA (complementary DNA; hereinafter referred to as cDNA) synthesized by reverse transcriptase (hereinafter referred to as RT) with RNA as the template. Further, a polynucleotide of the present invention may be single- or double-stranded, and the double-stranded form includes DNA-DNA duplexes, DNA-RNA duplexes and RNA-RNA duplexes. In the present invention, when one of the double-stranded polynucleotides is referred to as the sense strand, the other, i.e., the single-stranded polynucleotide comprising nucleotide sequence entirely complementary to the nucleotide sequence of the sense strand, is referred to as the anti-sense strand. Such polynucleotides of the present invention are exemplified by the following [N1] to [N10], preferably the polynucleotide is as described in any one of [N1], [N4] to [N6] or [N10]:

[N1] a polynucleotide coding for a polypeptide comprising the amino acid sequence as set forth in Sequence ID No. 2 of the Sequence Listing;
[N2] a polynucleotide coding for a polypeptide comprising an amino acid sequence in which one or several (two or more, up to ten) amino acids have been added, deleted, substituted or inserted into the amino acid sequence as set forth in Sequence ID No. 2 of the Sequence Listing and which has 2'-PDE activity;
[N3] a polynucleotide coding for a polypeptide comprising an amino acid sequence that is 80% or more, preferably 90% or more, and more preferably 95% or more identical to the amino acid sequence as set forth in Sequence ID No. 2 of the Sequence Listing and which has 2'-PDE activity;
[N4] a polynucleotide coding for a polypeptide coded by the polynucleotide inserted between the two restriction enzyme EcoR1 recognition sites of the recombinant plasmid DNA carried by the transformant *E. coli* pCR-Blunt II TOPO-F6-2/22 SANK 71002 (FERM BP-8142);
[N5] a polynucleotide comprising the nucleotide sequence as set forth in Sequence ID No. 1 of the Sequence Listing;
[N6] the polynucleotide inserted between the two restriction enzyme EcoR1 recognition sites of the recombinant plasmid DNA carried by the transformant *E. coli* pCR-Blunt II TOPO-F6-2/22 SANK 71002 (FERM BP-8142);
[N7] a polynucleotide comprising a nucleotide sequence that is 70% or more, preferably 80% or more, more preferably 90% or more identical to the nucleotide sequence as set forth in Sequence ID No. 1 of the Sequence Listing, and which codes for a polypeptide having 2'-PDE activity;
[N8] a polynucleotide comprising a nucleotide sequence in which one, or two or more, up to 20 nucleotides, have been added, deleted, substituted or inserted into the nucleotide sequence as set forth in Sequence ID No. 1 of the Sequence Listing, and which codes coding for a polypeptide having 2'-PDE activity;

[N9] a polynucleotide that hybridizes with a polynucleotide as described in [N5] or [N6] above under stringent conditions, and which codes for a polypeptide having 2'-PDE activity. In the present invention, the phrase "to hybridize under stringent conditions" means to hybridize by incubation at 55° C., for 4 hours or more, in prehybridization solution containing a 6-fold concentration of SSC solution (one-fold concentration of SSC consists of 150 mM NaCl and 15 mM sodium citrate), 5% Denhardt (Denhardt) solution and 0.1% sodium dodecyl sulfate (hereinafter referred to as "SDS"); to hybridize at 68° C. in a commercially-sold hybridization solution, ExpressHyb Hybridization Solution (manufactured by Clontech Lab., Inc.); or to hybridize under the conditions which can be identified using a filter to which DNA has been immobilized, by hybridization in the presence of 0.7 to 1.0 M NaCl at 68° C.; with subsequent washing using a 0.1 to 2-fold concentration of SSC solution at 68° C., or similar conditions; and

[N10] a fragment of a polynucleotide as described in any one of [N1] to [N9] above, coding for a polypeptide having the 2'-PDE activity. In the present invention, such a fragment is referred to as being an "active fragment".

More specific examples of [N10] include, isolated polynucleotides as described in any of the following [N10i] to [N10v]:

[N10i] a polynucleotide coding for a polypeptide consisting of an amino acid sequence in which the methionine at the 1st position, or two or more, up to 34, contiguous amino acids including the methionine at the 1st position, have been deleted in the amino acids from the methionine at the 1st position to the alanine at the 34th position in the amino acid sequence as set forth in Sequence ID No. 2 of the Sequence Listing;

[N10ii] a polynucleotide consisting of a nucleotide sequence in which the adenosine at the 1st position and the two 3' adjacent nucleotides (5'-terminal trimer), or 3n (n is an integer from 1 to 33) contiguous nucleotides including the 5'-terminal trimer, of the nucleotides from the adenosine at the 1st position to the guanosine at the 102nd position in the nucleotide sequence as set forth in Sequence ID No. 1 of the Sequence Listing have been deleted;

[N10iii] a polynucleotide coding for a polypeptide consisting of the methionine at the 35th position to the lysine at the 609th position in the amino acid sequence as set forth in Sequence ID No. 2 of the Sequence Listing;

[N10iv] a polynucleotide consisting of the adenosine at the 103rd position to the adenosine at the 1827th position in the nucleotide sequence as set forth in Sequence ID No. 1 of the Sequence Listing; and

[N10v] a polynucleotide from the adenosine at the 103rd position to the guanosine at the 1830th position in the nucleotide sequence as set forth in Sequence ID No. 1 of the Sequence Listing.

A polynucleotide as described in any of [N10i] to [N10v] codes for a short chain form of 2'-PDE of the present invention, and inter alia, a polynucleotide as described in any of [N10iii] to [N10v] codes for a short chain form of 2'-PDE (35-609).

In the present invention, "an antibody" is an antibody that specifically binds to a polypeptide of the present invention, or an active fragment thereof, preferably, an antibody that specifically binds to a polypeptide of the present invention and neutralizes the 2'-PDE activity of the polypeptide of the present invention (hereinafter referred to as a "neutralizing antibody"), or an active fragment thereof, more preferably, an antibody that specifically binds to a more preferable polypeptide of the present invention and that is a neutralizing antibody against said polypeptide, or an active fragment thereof, and further more preferably, one that specifically binds to a most preferable polypeptide of the present invention and that is a neutralizing antibody to said polypeptide, or an active fragment thereof. An antibody of the present invention can be an anti-serum, polyclonal antibody, monoclonal antibody, chimeric antibody, single-chain antibody, humanized antibody, human antibody, or an active fragment of any thereof. The animal from which the antibody of the present invention is derived and the animal from which the immunogen used in preparing the antibody of the present invention is derived, are not limited, provided that each of them can be either human or a non-human mammal.

In the present invention, "a fragment" means a fragment of a polypeptide, polynucleotide, or antibody of the present invention. Further, "an active fragment" is a fragment of a polypeptide of the present invention having 2'-PDE activity, a fragment of a polynucleotide of the present invention coding for a polypeptide having 2'-PDE activity, or a fragment of an antibody of the present invention that can specifically bind to a polypeptide of the present invention; these are included in the terms polypeptide, polynucleotide, or antibody of the present invention, respectively.

A polypeptide, polynucleotide, recombinant plasmid DNA, or antibody of the present invention, or fragment thereof, is preferably isolated.

A polypeptide of the present invention can be a natural or recombinant form. A natural form of a polypeptide can be extracted, purified and/or isolated from a tissue, organ or cell using 2'-PDE activity as an indicator the index. The source of the natural form of the polypeptide is not limited, provided that 2'-PDE is expressed; sources include, for example, the liver. Examples of the means for extraction, purification and/or isolation of the polypeptide of the present invention from such a source include cell fractionation, salting-in, salting-out, dialysis, hydrophobic interaction chromatography, affinity chromatography, ion exchange chromatography, gel filtration chromatography, and electrophoresis, and suitably these means can be combined as appropriate.

A recombinant form of the polypeptide can be extracted, purified and/or isolated, using 2'-PDE activity or an affinity tag as an indicator, from a culture obtained by the steps of; firstly isolating a polynucleotide coding for the polypeptide, then inserting said polynucleotide into a suitable expression plasmid DNA, then transforming a host cell with said resulting recombinant expression plasmid DNA, and then culturing the host cell obtained. The present invention also provides such a process for preparing a recombinant form of the polypeptide. Further, a polypeptide obtainable by such a process is included as being a polypeptide of the present invention.

An isolated polypeptide comprising an amino acid sequence that is 80% or more, preferably 90% or more, more preferably 95% or more, identical to the amino acid sequence as set forth in Sequence ID No. 2 of the Sequence Listing and having 2'-PDE activity can be obtained as a recombinant form of the polypeptide by, for example, expression cloning from a cDNA library derived from a human source, or a mammalian source other than human, using a polynucleotide comprising the nucleotide sequence as set forth in Sequence ID No. 1 of the Sequence Listing, or a fragment thereof, as a probe.

An isolated polypeptide comprising an amino acid sequence in which one or several (two or more, up to 10) amino acids have been added, deleted, substituted or inserted into the amino acid sequence as set forth in Sequence ID No. 2 of the Sequence Listing and having 2'-PDE activity can be obtained as a recombinant form of the polypeptide by a process comprising following steps: obtaining a mutated polynucleotide using, for example, a method comprising partially digesting a polynucleotide comprising the nucleotide sequence as set forth in Sequence ID No. 1 of the Sequence Listing from the terminus using exonuclease Bal31 etc. (Eds. Mitsuru Takanami et al., "Zoku Seikagaku Jikken Koza 1: Idensi Kenkyuhou II Kumikae DNA Gijutsu," published by Tokyo Kagaku Dozin Co., Ltd. in 1986, pp. 335-354); a method of cassette mutagenesis (Eds. Masami Muramatsu et al., "Shin Seikagaku jikken Koza 2 Kakusan III Kumikae DNA Gijutsu," published by Tokyo Kagaku Dozin Co., Ltd. in 1992, pp. 242-251), a PCR method using a mutated primer, a method of site-specific mutagenesis; and then expressing the polypeptide coded by the resulting polynucleotide.

Incidentally, there is a report of a mutant interleukin-2 protein which retains the biological activity of the wild type Interleukin-2 (hereinafter IL-2) protein. The report relates to a mutated IL-2 in which a cysteine residue in the amino acid sequence of the wild type IL-2 was replaced by a serine and it was shown that the mutant IL-2 had the same biological activity as the wild type IL-2 (Wang, A. et al. (1984) Science 224, 1431-1433).

An active fragment of a polypeptide of the present invention may be obtained by removing residues from the polypeptide at the amino terminus and/or carboxyl terminus. Specifically, an active fragment can be obtained by, for example, shortening the polypeptide using a process in which a polynucleotide of the present invention, a polynucleotide comprising the nucleotide sequence as set forth in Sequence ID No. 1 of the Sequence Listing, is digested from its terminus using the exonuclease Bal31 (BAL31 Nuclease) etc. (as described above) and confirming that it encodes polypeptide which retains 2'-PDE activity.

An active fragment of the polypeptide of the present invention includes the short chain form of 2'-PDE. A recombinant short chain form of 2'-PDE can be prepared by inserting into a plasmid DNA a polynucleotide consisting of the nucleotide sequence from which the adenosine at 1st position and the 3' adjacent two nucleotides (5'-terminal trimer) or 3n (n is an integer from 1 to 33, inclusive) contiguous nucleotides including the 5'-terminal trimer have been deleted from the nucleotides from the adenosine at the 1st position to the guanosine at the 102nd position in the nucleotide sequence as set forth in Sequence ID No. 1 of the Sequence Listing, then transforming a host cell with the resulting recombinant plasmid DNA, and after culturing the resulting transformed cell, recovering the short chain form of 2'-PDE from the culture.

A methionine can be added if necessary to the amino-terminus of the short chain form of 2'-PDE, (e.g., for the purpose of the expression in a host cell). It is possible to prepare a desired short chain form of the polypeptide having a methionine at the amino-terminus, if a methionine codon is added to the 5'-terminus of the insert sequence of the recombinant plasmid DNA. Further, at the amino-terminus of a short chain form of 2'-PDE, it is possible to add a signal peptide, if necessary. By doing so, it is possible to prepare a desired short chain form of polypeptide as a secreted protein and moreover to prepare a mature protein that does not contain the above described amino-terminus methionine which was added by genetic engineering. When making a secreted protein, it is desirable to take care to avoid inactivation of the enzyme.

Further, a recombinant short chain form of 2'-PDE (35-609) may be prepared by inserting into a plasmid DNA a polynucleotide consisting of the adenosine at the 103rd position to the guanosine at the 1830th position in the nucleotide sequence as set forth in Sequence ID No. 1 of the Sequence Listing, then transforming a host cell with the resulting recombinant plasmid DNA, and after culturing the resulting transformant cell, harvesting the short chain form of 2'-PDE from the culture. Further, a recombinant short chain form of 2'-PDE (35-609) may be prepared by inserting into a plasmid DNA a polynucleotide consisting of the full-length nucleotide sequence as set forth in Sequence ID No. 1 or a polynucleotide from which 0 to 102 nucleotides have been deleted from the 5'-terminus of that polynucleotide, then transforming a host cell (e.g., a human fetal kidney cell line 293 cell) with the resulting recombinant plasmid DNA, and after culturing the resulting transformed cell, recovering the desired short chain form of 2'-PDE. It is desirable that, in the polynucleotide used for preparation of a recombinant short chain form of 2'-PDE (35-609), the region which is 5'-termininal to the methionine codon (ATG) at the 103rd to 105th position and which is within the same reading frame as the methionine codon includes no other methionine codon. It should be noted that the short chain form of 2'-PDE (35-609) can be expressed in a host cell without the addition of a methionine or a signal peptide.

A multimer of a polypeptide of the present invention may be obtained according to a method well-known to those skilled in the art, such as described in WO98/49305 or WO2001/18203.

Further, an active derivative of a polypeptide of the present invention may also be obtained according to any method well-known to those skilled in the art (e.g. as described in U.S. Pat. No. 4,179,337; EP 0401384; Malik et al., Exp. Hematol., 20, pp. 1028-1035 (1992); WO2000/24416).

A polynucleotide of the present invention may be cloned by extracting genomic DNA or mRNA from a tissue, organ or cell, or a cell line derived from an animal, according to a conventional method, then preparing a genomic DNA library or cDNA library, and using a nucleotide coding for a polypeptide or a fragment thereof of the present invention as a probe. Furthermore, expression cloning can be performed using an antibody or an active fragment thereof of the present invention as a probe, or using 2'-PDE activity as an indicator. An mRNA expressed by a clone thus obtained, a corresponding cDNA, or a genomic DNA of the clone, are all polynucleotides of the present invention.

A cDNA of the present invention may be cloned from a cDNA library synthesized according to a conventional method using total RNA or mRNA as the template. A human source is preferred as the source of the total RNA or mRNA.

Typically the extraction method for total RNA or mRNA, can be a guanidine thiocianate—cesium chloride ultracentrifugation method, a guanidine thiocianate—hot phenol method, or a guanidine hydrochloride method; a preferred method is the acidic guanidine thiocianate phenol chloroform method (Chomczynski, P. and Sacchi, N., (1987) Anal. Biochem., 162, 156-159).

It is known that most mRNA existing in the cytoplasm of cells derived from eukaryotes, such as mammals, has a poly (A) sequence at its 3'-terminus, and by using this feature it is possible to purify mRNA by adsorbing the mRNA contained in total RNA to a biotinylated oligo(dT) probe, further capturing the mRNA onto paramagnetic particles to which streptoavidin has been immobilized using the binding between biotin and streptoavidin, and then eluting the mRNA after washing. Furthermore, mRNA can also be obtained by adsorbing mRNA onto an oligo(dT) cellulose column and then eluting the adsorbed fraction. Moreover, it is also possible to purify mRNA to a higher degree using a sucrose density gradient centrifugation method or the like.

Confirmation that the thus obtained mRNA codes for a polypeptide of the present invention can be achieved by detecting the activity of the polypeptide coded by the mRNA or by immunological detection using an antibody that specifically binds to the polypeptide of the invention. For example, by injecting the mRNA into an oocyte of Africa clawed frog (*Xenopus laevis*) the polypeptide coded by the mRNA can be obtained as a translation product (Gardon, J. B. et al. (1972) Nature 233, pp. 177-182). Similarly, a translation product can be obtained using a cell-free translation system such as the rabbit reticulocyte system, or the wheat germ system. (Schleif, R. F. and Wensink, P. C. (1981): "Practical Methods in Molecular Biology," Springer-Verlag, NY).

With mRNA as the template, using a reverse transcriptase (reverse transcriptase; hereinafter referred to as "RT") derived from a retrovirus, the 1st strand of complementary DNA (complementary DNA; hereinafter referred to as "cDNA") can be synthesized, and after that using the 1st strand cDNA as the template and using a DNA polymerase, a 2nd strand cDNA can be synthesized. Such cDNA can be prepared using the S1 nuclease method (Efstratiadis, A. et al. (1976) Cell 7, pp. 279-288), the Land method (Land, H. et al. (1981) Nucleic Acids Res. 9, pp. 2251-2266), the O. Joon Yoo method (Yoo, O. J. et al. (1982) Proc. Natl. Acad. Sci. USA 79, pp. 1049-1053), or the Okayama-Berg method (Okayama, H. and Berg, P. (1982) Mol. Cell. Biol. 2, pp. 161-170); a preferred method is the Okayama-Berg method.

By inserting the cDNA obtained into a plasmid DNA vector or lambda phage vector and then introducing the vector into a host cell, a cell carrying the desired cDNA can be obtained. When a lambda phage vector is used, by inserting the cDNA into the lambda phage vector and allowing it to self-replicate, it is possible to stably maintain recombinant phage carrying the cDNA and to allow phage proliferation. For example, when lambda phage λZAPII (manufactured by Stratagene) is used, plaques can be made in lawns of the host *E. coli* strains XL1-Blue MRF' or JM109, and, based on the presence or absence of color development due to metabolism of 5-Bromo-4-chloro-3-indolyl-β-D-galactopyranoside (5-Bromo-4-chloro-3-indolyl-β-D-galactopyranoside (X-gal)) in the plaques, recombinants can be selected. Examples of processes for screening the recombinant phages for clones having cDNA coding for the desired polypeptide with 2'-PDE activity include the methods described in the [I] to [IV] below. Furthermore, a desired polynucleotide (e.g. genomic DNA) other than cDNA can also be selected by using a method according to any one of [I] to [IV] below.

[I] Method Using a Synthetic Oligonucleotide Probe.

A full-length or a partial amino acid sequence of a polypeptide coded by the desired DNA (the sequence may be any part of the polypeptide provided that it is a contiguous sequence specific to the polypeptide) is identified, an oligonucleotide coding for the amino acid sequence is synthesized, and labeled with a radioisotope such as $^{32}P$, $^{35}S$ etc. or biotin etc., and the labeled oligonucleotide is used as the hybridization probe for a nitrocellulose filter or nylon filter to which recombinant phage DNA has been denatured and immobilized, a positive clone thus obtained is then selected. For synthesis of oligonucleotides, when an amino acid has a degenerate codon, a frequently used codon may be used, or two or more nucleotide sequences may be synthesized by combining possible codons, and in the latter case, the degeneracy may be reduced by incorporating inosine.

[II] Method Using a Probe Prepared by the Polymerase Chain Reaction Method.

When a full-length or partial amino acid sequence of a polypeptide coded by a desired polynucleotide is identified, a fragment of the desired cDNA can be amplified by synthesizing an oligonucleotide comprising a portion of the 5'-terminal nucleotide sequence of the sense strand and an oligonucleotide comprising a portion of the 3'-terminal nucleotide sequence of the anti-sense strand, and then conducting a polymerase chain reaction (hereinafter referred to as "PCR"; see Saiki, R. K. et al. (1988) Science 239, pp. 487-491). In this process, the template DNA used can be, cDNA synthesized by reverse transcription of total RNA or mRNA extracted from cells derived from a mammal producing a polypeptide of the present invention, or genomic DNA of the mammal may be used. The thus prepared DNA fragment is labeled with a radioisotope such as $^{32}P$, $^{35}S$ etc., or biotin etc., and, using this labeled DNA as the probe, the clone of interest can be selected by plaque hybridization, colony hybridization, or a similar technique.

[III] Method for Producing a Polypeptide Having 2'-PDE Activity in an Animal Cell Line.

A strain containing cDNA coding for a polypeptide of the present invention can be selected by transforming an animal cell host with an expression vector plasmid into which cDNA obtained as described above has been inserted (or a plasmid that can self-replicate and contains a transcription promoter region, or a plasmid that can be integrated into a chromosome of an animal cell may be used), allowing production of the polypeptide coded by the cDNA, and measuring 2'-PDE activity in the culture supernatant or in the cell extract, or detecting the polypeptide of the present invention using antibody or an active fragment thereof of the present invention and a second antibody against a first antibody fragment. As the cell host, a common cell line derived from a mammal, such as COS, CHO etc., may be used. But, in order to facilitate detection of the polypeptide of the present invention as a foreign gene product, it is preferred that the host cell itself is such that expression of a polypeptide of the present invention is not detected under certain culture conditions.

[IV] Method Using a Selective Hybridization Translation System.

cDNA obtained from a transformant strain is blotted onto a nitrocellulose filter, nylon filter or the like, and, after it is hybridized with mRNA extracted from a tissue or cells capable of producing a polypeptide of the present invention, mRNA bound to the cDNA is dissociated and recovered. A desired clone can be selected by translating the recovered mRNA into a polypeptide using a protein translation system (for example, by injection into an oocyte of *Xenopus laevis*, or using a cell-free system, such as rabbit reticulocyte lysate or wheat germ extract) and measuring 2'-PDE activity of the polypeptide or using an antibody or an active fragment thereof, according to the present invention.

The desired polynucleotide can be purified and isolated from a culture of the clone thus selected, according to a method well-known to those skilled in the art. For example, the desired polynucleotide can be excised from the vector by isolating plasmid DNA vector or lambda phage vector from the culture and then using an endonuclease such as a restriction enzyme. (Maniatis, T. et al. (1982): "Molecular Cloning A Laboratory Mannual" Cold Spring Harbor Laboratory, NY).

A genomic DNA library can be obtained by physically crushing an organ, tissue, cell, or body fluid of human organ or from a non-human mammal, or a cell line derived from an animal, then extracting and purifying the nuclear DNA, then, after appropriate fragmentation of the DNA, inserting DNA fragments into a vector and, then transforming a host cell with the resulting recombinant vector.

Physical crushing of a sample can be performed by homogenization with a Polytron homogenizer or the like. Extraction of nuclear DNA present in the crushed sample can be performed using a detergent such as sodium dodecyl sulfate (sodium dodecyl sulfate; hereinafter referred to as "SDS") Extracted genomic DNA can be deproteinized by conducting a phenol-chloroform extraction and recovering the DNA as a precipitate by conducting ethanol precipitation.

The genomic DNA obtained is partially digested using an appropriate restriction enzyme to generate fragments. The enzyme that can be used for the partial digestion is not particularly limited, provided that it is a generally available restriction enzyme, for example, Sau3AI or similar. The fragmented DNA is subjected to gel electrophoresis and genomic DNA of an appropriate size is recovered from the gel.

There are no paticular restrictions on the size of the DNA fragment, but DNA fragments are preferably 20 kb or more.

There are no particular limitations on the vector for preparation of a genomic DNA library, provided that the vector has a base sequence appropriate for replication in the host cell transformed with the vector; suitable vectors include, for example, plasmid DNA, phage vectors, cosmid vectors, and BAC vectors, with cosmid vector being preferred.

The vector may be an expression vector. Further, it is preferred that the vector has a base sequence that confers a selectable phenotype (phenotype; Phenotype) on a host cell transformed with the vector. The vector is preferably such that it can be used in both cloning and functional expression, and it is preferred to use a vector that can transform two or more types of host cells, i.e., a shuttle vector. A shuttle vector has a base sequence suitable to allow it to be replicated in at least one host cell type. In the present invention, these vectors are included in the meaning of "plasmid DNA" for the purpose of convenience.

When the host cell is *E. coli*, the introduction of recombinant plasmid DNA is sometimes conducted by in vitro packaging. In the present invention, "transformation" also means the introduction of foreign DNA by in vitro packaging and a host cell into which foreign DNA has been introduced by in vitro packaging is included within the meaning of a transformed host cell.

The nucleotide sequence of a polynucleotide of the present invention can be determined by, for example, the chemical modification method of Maxam and Gilbert (Maxam, A. M. and Gilbert, W. (1980): "Methods in Enzymology" 65, pp. 499-559), or the dideoxy nucleotide chain termination method (Messing, J. and Vieira, J. (1982) Gene 19, pp. 269-276). Further, a commercial automatic DNA sequence analyzer can be used, (for example, Model 373A manufactured by Perkin Elmer Japan Applied Biosystems) using a fluorescent dye instead of a radioisotope.

A transformed *E. coli*, pCR-Blunt II TOPO-F6-2/22 SANK 71002, carrying a recombinant plasmid DNA into which a more preferred polynucleotide of the present invention has been inserted, was internationally deposited with the National Institute of Advanced Industrial Science and Technology International Patent Organism Depositary on Aug. 6, 2002, and allocated the accession number FERM BP-8142.

A recombinant plasmid DNA into which a polynucleotide of the present invention has been inserted is included in the present invention. There are no particular restrictions on a recombinant plasmid DNA of the present invention, provided that it contains elements that allow transformation of a host cell, i.e., a replicon (replication origin) derived from a species compatible with the host cell and a transcription promoter (hereinafter referred to as a promoter), and preferably contains an element that can confer a selectable phenotype (phenotype) useful for selecting a transformed host cell. A more preferred recombinant plasmid DNA is a recombinant expression plasmid DNA. Namely, it is recombinant expression plasmid DNA into which a polynucleotide of the present invention has been inserted, making it possible to express a polypeptide of the present invention in the transformed host cell by transforming a prokaryotic host cell such as *E. coli*, or a host cell derived from a eukaryote, such as a CHO cell, a dihydrofolate dehydrogenase-deficient strain of a CHO cell, or a COS cell. It is preferred that a plasmid DNA used for expression contains a suitable promoter, elements necessary for expression etc. The recombinant plasmid DNA carried by the transformant *E. coli*, *E. coli* pCR-Blunt II TOPO-F6-2/22 SANK 71002 (FERM BP-8142) is also included within the scope of the present invention.

A host cell transformed with a recombinant plasmid DNA of the present invention is also included in the present invention.

Among such host cells, prokaryotic host cells include, for example, *E. coli* (*Escherichia coli*) strains, *B. subtilis* (*Bacillus subtilis*) strains and the like, preferably host cells are derived from a species compatible with the species from which the replicon carried by the recombinant plasmid DNA is derived. Suitable *E. coli* strains and *B. subtilis* strains include the K12 strains and 207-25 strains, respectively. The transformed *E. coli* pCR-Blunt II TOPO-F6-2/22 SANK 71002 (FERM BP-8142) is also included within the scope of the present invention.

When *E. coli* is the host cell, examples of plasmid DNA are pBR322 and plasmid DNA of the pUC series, but the term "plasmid DNA" is not restricted to these examples, and various strains and plasmid DNA available to those skilled in the art may be used. The promoter contained in the plasmid DNA when *E. coli* is the host cell can be for example, a tryptophan (trp) promoter, a lactose (lac) promoter, a tryptophan-lactose (tac) promoter, a lipoprotein (lpp) promoter, a polypeptide chain elongation factor Tu (tufB) promoter or the like. The promoter contained in the plasmid DNA when *B. subtilis* is the host cell can be that of pTUB228 (Ohmura, K. et al. (1984) J. Biochem. 95, pp. 87-93).

Further, by ligating a nucleotide sequence coding for a signal peptide to the 5'-terminus of a polynucleotide of the present invention, either directly or indirectly via a spacer, it is possible for the host cell to secrete a polypeptide of the present invention outside of the host cell. For example, by transforming *B. subtilis* with a recombinant expression plasmid DNA in which DNA coding for a signal peptide of *B. subtilis* α-amylase has been ligated to a polynucleotide of the present invention, the desired polypeptide can be secreted outside of the transformant *B. subtilis*.

Eukaryotic host cells include cells from vertebrates such as mammals, from arthropoda such as insects, or cells derived from plants, or yeast; cells derived from mammals can be, for example, COS cells (Gluzman, Y. (1981) Cell 23, pp. 175-182: ATCC CRL-1650) which are monkey cells, Chinese hamster ovary cells (CHO cells: ATCC CCL-61), dihydrofolate reductase-deficient strains of CHO cells (Urlaub, G. and Chasin, L. A. (1980) Proc. Natl. Acad. Sci. USA 77, pp. 4126-4220) etc. COS cells of the present invention include COS-1 cells, COS-7 cells and the like.

When a vertebrate cell is used as the host cell, the recombinant expression plasmid DNA will normally contain a promoter located 5'-upstream of a polynucleotide of the present invention, a translation initiation site, an RNA splicing site, a polyadenylation site, and a transcription termination sequence; a replication origin may be included, if necessary. Such plasmid DNA includes, but is not limited to, pSV2dhfr (Subramani, S. et al. (1981) Mol. Cell. Biol. 1, pp. 854-864) that has a SV40 early promoter.

When a COS cell is used as the host cell, the recombinant expression plasmid DNA, is suitably one that can autonomously replicate in the COS cell and further contains a promoter, transcription termination signal, and a RNA splicing site. The expression vector can be transfected into a COS cell using the diethylaminoethyl (DEAE)—dextran method (Luthman, H. and Magnusson, G. (1983) Nucleic Acids Res., 11, pp. 1295-1308), the calcium phosphate—DNA co-precipitation method (Graham, F. L. and van der Eb, A. J. (1973) virology 52, pp. 456-457), or electroporation (Neumann, E. et al. (1982) EMBO J. 1, pp. 841-845). In the present invention, transfection is included in the meaning of transformation.

When a CHO cell is used as a host cell, a clone stably expressing a polypeptide of the present invention can be obtained. By co-transfecting a recombinant expression plasmid DNA, with a vector that can express a functional neo gene as an antibiotic G418 resistant marker, for example, pRSV-neo (Sambrook, J. et al. (1989): "Molecular Cloning A Laboratory Manual" Cold Spring Harbor Laboratory, NY) or pSV2-neo (Southern, P. J. and Berg, P. (1982) J. Mol. Appl. Genet. 1, pp. 327-341), and selecting for a G418 resistant colony.

A host cell derived from an insect can be, for example a line of cells derived from an ovarian cell of a species of *Lepidoptera Noctuidae* (*Spodoptera frugiperda*) (Sf-9, Sf-21 etc.), or, similarly, a High Five cell derived from an egg cell of a species of *Lepidoptera Noctuidae* (*Trichoplusia ni*) (Wickham, T. J. et al, (1992) Biotechnol. Prog. I: pp. 391-396) etc., and the expression plasmid DNA can be, for example a baculovirus transfer vector such as pVL1392/1393 with the polyhedron protein promoter of *Autographa* nuclear polyhedrosis virus (AcNPV), or a vector with the P10 baculovirus promoter or baculovirus basic protein. (Kidd, I. M. and V. C. Emery (1993), The use of baculoviruses as expression vectors. Applied Biochemistry and Biotechnology 42, pp. 137-159). When an insect cell is transformed with an expression plasmid DNA in which a polynucleotide of the present invention is ligated to DNA coding for a signal peptide (such as GP67 amylase, the envelope surface protein of AcNPVGP67), the desired polypeptide is secreted outside of the insect cell (Zhe-mei Wang, et al. (1998) Biol. Chem., 379, pp. 167-174).

Yeast can be exemplified by species of the genus *Saccharomyces* (*Saccharomyces*) such as baker's yeast (*Saccharomyces cerevisiae*), and *Candida tropicalis* (*Pichia pastoris*) and the like. Expression plasmid DNA for yeast may include a promoter such as the alcohol dehydrogenase gene promoter (Bennetzen, J. L. and Hall, B. D. (1982) J. Biol. Chem. 257, pp. 3018-3025) or acidic phosphatase gene promoter (Miyanohara, A. et al. (1983) Proc. Natl. Acad. Sci. USA 80, pp. 1-5). Further, when the desired polypeptide is to be secreted outside of the cell, it is preferred to add a signal peptide, and a recognition site for an endogenous protease carried by the host cell, or a protease well-known to those skilled in the art, at the amino-terminus of a polypeptide of the present invention. When *C. tropicalis* is the host cell, for example, by adding the signal peptide of yeast α-factor and the cleavage site for KEX2 protease derived from *C. tropicalis* at the amino-terminal side of the desired polypeptide, the polypeptide can be secreted outside of the *C. tropicalis* cells (Andrew, L. Niles, et al. (1998) Biotechnol. Appl. Biochem. 28, pp. 125-131).

A transformed host cell of the present invention can be cultured according to a conventional method, and from the culture, a polypeptide and/or polynucleotide of the present invention can be recovered. Suitably, the medium used for culturing a transformed host cell can be selected from those conventionally used depending on the type of the host cell.

The medium for a COS cell can be, for example, RPMI 1640 medium, or Dulbecco's modified Eagle medium (hereinafter referred to as DMEM). To these media, serum or serum components, e.g. derived from fetal calf, may be included as necessary.

A polypeptide and/or polynucleotide of the present invention present in the above described culture can be purified and isolated based on their physicochemical or biochemical characteristics by fractionation means well-known to those skilled in the art. Fractionation means include centrifugation, salting-in, salting-out, dialysis, ultrafiltration, gel filtration, ion-exchange chromatography, affinity chromatography, hydrophobic interaction chromatography, partition chromatography, reversed phase chromatography, normal phase chromatography, electrophoresis and the like, and, for chromatographic fractionation high performance liquid chromatography (high performance liquid chromatography: hereinafter referred to as HPLC) etc. can be used. If a tag (tag) has been added to the desired polypeptide or polynucleotide in advance, then using the tag, the polypeptide or polynucleotide can easily be purified and isolated. For example, by adding a polynucleotide coding for a histidine oligomer at the 5'-terminus of the sense strand of a polynucleotide of the present invention, a polypeptide with a histidine oligomer at the N-terminus can be expressed and, by metal chelate affinity chromatography, e.g. using nickel, the desired polypeptide with the tag can be efficiently purified.

The present invention includes within its scope a process for preparing a polypeptide or polynucleotide of the present invention, and a polypeptide or polynucleotide prepared by a process as described above.

Furthermore, a polynucleotide of the present invention can be chemically synthesized by a method such as the phosphite triester method (Hunkapiller, M. et al. (1984) Nature 310, pp. 105-111). Similarly, a polypeptide of the present invention can be chemically synthesized by a solid phase synthesis method and so on.

The amino acid sequence of a polypeptide of the present invention can be deduced based on a nucleotide sequence of the polynucleotide of the present invention. Further, the amino acid sequence of the polypeptide of the present invention can be determined based on the amino acid sequence of a portion or whole of the polypeptide of the present invention (hereinafter referred to as a search sequence query) by analyzing known nucleotide sequences of cDNA or genomic DNA, including EST, on a computer (in silico: in silico) as an amino acid sequence coded by an open reading frame that is continuous, interrupted by one or more introns. At the same time it is possible to determine the nucleotide sequence coding for an amino acid sequence of the polypeptide of the present invention, i.e., the nucleotide sequence of a polynucleotide of the present invention. The search sequence query is a specific amino acid sequence or spectrum data obtained using a peptide having an amino acid sequence such as that of the sample. There is no particular restriction on the spectrum, provided that it is useful for predicting the amino acid sequence, but preferably, a mass spectrometric spectrum is used. By subjecting the mass spectrum data to analysis using a software such as Mascot (manufactured by Matrix Science Ltd.: Electrophoresis, 20(18), pp. 3551-3567 (1999)), MS-Tag (manufactured by University of California San Francisco), Peptide Search (manufactured by European Molecular Biology Laboratory), SEQUEST (manufactured by ThermoFinnigan) or the like, a search of the database can be conducted (Eds. Toshiaki Isobe and Nobuhiro Takahashi, Post Genome Jidai no Jikken Koza 2 Proteome Kaisekiho, Jikken Igaku Bessatsu, published from Yodosha Co., Ltd. in 2000).

A polypeptide which is to be subjected to mass spectrometry is preferably purified or partially purified. When it is partially purified, the desired polypeptide can be isolated by, for example, subjecting a sample containing the polypeptide to SDS-polyacrylamide electrophoresis, identifying the band corresponding to the 2'-PDE activity and then excising a gel slice containing the band.

When subjecting a polypeptide to mass spectrometry, the polypeptide can be pre-digested with a protease, then the resulting peptide fragments can be fractionated by column chromatography; the peptide fragments eluted from the column can be sequentially subjected to mass spectrometry. For such a mass spectrometric analysis, suitably a tandem mass spectrometer such as Q-TOF2 (manufactured by Micromass) can be used.

Based on the nucleotide sequence determined in silico, a polypeptide of the present invention can be obtained by cloning and expressing a polynucleotide of the present invention.

There are no limitations on a codon corresponding to an amino acid in a polypeptide of the present invention which is used in an isolated polynucleotide coding for a polypeptide comprising the amino acid sequence as described in Sequence ID No. 2 of the Sequence Listing, provided that it codes for that amino acid, and can be selected, for example, with consideration of the host cell codon usage (Grantham, R. et al. (1981) Nucleic Acids Res. 9, pp. 143-174). Modification of a codon can be performed according to any method well-known to those skilled in the art, for example, site-specific mutagenesis using a synthetic oligonucleotide primer coding for the desired modification (site-specific mutagenesis; Mark, D. F. et al. (1984) Proc. Natl. Acad. Sci. USA 81, pp. 5662-5666).

A polynucleotide coding for a polypeptide comprising a nucleotide sequence that is 70% or more, preferably 80% or more, more preferably 90% or more identical to the nucleotide sequence as set forth in Sequence ID No. 1 of the Sequence Listing and which has 2'-PDE activity, or a polynucleotide coding for a polypeptide that hybridizes with the polynucleotide comprising the nucleotide sequence as set forth in Sequence ID No. 1 of the Sequence Listing under stringent conditions and which has 2'-PDE activity, can be obtained as a recombinant polynucleotide (Maniatis, T. et al. (1982) in "Molecular Cloning A Laboratory Manual," Cold Spring Harbor Laboratory, NY.), for example, by performing expression cloning from a cDNA library or genomic library derived from a human source or a non-human mammal using, as a probe, a nucleotide comprising the nucleotide sequence as set forth in Sequence ID No. 1 of the Sequence Listing or a fragment thereof, labeled with [α-32P]dCTP or the like, by a random primer method (Anal. Biochem., 132: 6-13 (1983)) or by a nick translation method (Maniatis, T. et al., described above).

A polynucleotide coding for a polypeptide comprising a nucleotide sequence in which one, or two or more, up to 20 nucleotides have been added, deleted, substituted or inserted in the nucleotide sequence as set forth in Sequence ID No. 1 of the Sequence Listing and having 2'-PDE activity can be obtained, for example, according to a method in which a polynucleotide comprising the nucleotide sequence as set forth in Sequence ID No. 1 of the Sequence Listing is digested from its terminus using the exonuclease Bal31 or the like (as described above), by a cassette mutagenesis method (as described above), by a site specific mutagenesis method, by PCR using a mutated primer etc. Generally, a gene presents polymorphism (polymorphism) (see Nishi, T. et al. (1985) J. Biochem. 97, pp. 153-159 etc.) Among those polynucleotides naturally present due to polymorphism, the present invention comprises polynucleotides coding for polypeptides having 2'-PDE activity.

A monoclonal antibody provided by the present invention can be obtained as usual by the following steps [a]to [g], but not being restricted thereto:

[a] a step of purifying, partially purifying or isolating a polypeptide of the present invention as the immunogen;

[b] a step of immunizing an animal with the above described immunogen, removing the spleen from the animal at an appropriate time, and then preparing antibody-producing cells;

[c] a step of preparing myeloma cells (hereinafter referred to as "myeloma");

[d] a step of fusing the antibody-producing cells and myeloma to form hybridoma;

[e] a step of selecting hybridomas producing the desired antibody;

[f] a step of obtaining a single cell from the hybridomas (cloning); and

[g] a step of confirming that the monoclonal antibody produced by the single cell specifically binds to the polypeptide of the present invention.

The immunogen is provided for immunization of an animal after being mixed with an adjuvant such as Freund's complete adjuvant, Freund's incomplete adjuvant, potassium alum and the like. As the animal to be immunized, mice and rabbits are preferred, although the choice of animal is not limited thereto.

The method of administration of the immunogen is, for example, by subcutaneous injection, intraperitoneal injection, i.v. injection, intradermal injection, and intramuscular injection, with subcutaneous injection and intraperitoneal injection being preferred.

The immunogen can be administered once, or repeatedly several times at an appropriate interval (preferably at an interval of one to five weeks). After that, the titer of antibody against the immunogen in the serum of the immunized animal is measured, and it is preferred that the spleen is removed from the animal when the antibody titer is fully elevated. When a mouse is immunized, it is preferred that the spleen is removed 3 to 5 days after the last administration of the immunogen, and then the antibody producing cell is obtained.

The method for measuring antibody titer can include: a radioisotope immunoassay (hereinafter referred to as RIA), a solid phase enzyme immunoassay (hereinafter referred to as ELISA), a fluorescent antibody method, or a passive hemagglutination reaction, with RIA and ELISA being preferred.

For ELISA, an insoluble carrier on which the immunogen has been immobilized is blocked with bovine serum albumin or the like, then the carrier is contacted with serially-diluted samples of a 1st antibody, it is then contacted with a 2nd antibody labeled with an enzyme, and then the substrate for the enzyme is added; fluorescent color development, or change in absorbance, due to degradation of the substrate, is measured, to calculate the antibody titer.

As the myeloma, cell lines derived from mice are generally used, for example from 8-azaguanine resistant mice (derived from BALB/c) myeloma strains, such as P3X63Ag8U.1 (P3-

U1) (Yelton, D. E. et al., Current Topics in Microbiology and Immunology, 81, pp. 1-7(1978)), P3/NS1/1-Ag4-1 (NS-1) (Kohler, G. et al., European J. Immunology, 6, pp. 511-519 (1976)), Sp2/O-Ag14 (SP-2) (Shulman, M. et al., Nature, 276, pp. 269-270 (1978)), P3X6Ag8.653 (Kearney, J. F. et al., J. Immunology, 123, pp. 1548-1550 (1979)), P3X63Ag8 (X63) (Horibata, K. and Harris, A. W., Nature, 256, pp. 495-497 (1975)). The cells are sequentially cultured in 8-azaguanine medium (medium in which 8-azaguanine has been added to RPMI 1640 medium supplemented with glutamine, 2-mercaptoethanol, gentamicin, and fetal calf serum), Iscove's modified Dulbecco's medium (Iscove's Modified Dulbecco's Medium; hereinafter referred to as IMDM), Dulbecco's modified Eagle medium (Dulbecco's Modified Eagle Medium; hereinafter referred to as DMEM), or sequentially cultured in a normal medium such as ASF104 medium (manufactured by Ajinomoto Co., Inc.) supplemented with 10% FCS 3 to 4 days prior to the cell fusion.

The antibody-producing cell is a plasma cell or its precursor cell, a lymphocyte, which can be obtained from any part of an immunized animal subject but is generally obtained from the spleen, lymph node, peripheral blood, or a suitable combination of these, with the spleen being the preferred source.

In the method for fusing an antibody-producing cell, such as a spleen cell, and a myeloma, polyethylene glycol is generally used. For example, the spleen cell and myeloma can be washed with serum-free medium or phosphate buffered saline (hereinafter referred to as PBS), and then mixed such that the ratio of cell numbers of the spleen cells and myeloma is between 5:1 to 10:1, and subsequently centrifuged; after which the supernatant is removed and the pellet is well softened; next, 1 ml of the serum-free medium containing 50% (w/v) polyethylene glycol (molecular weight 1000 to 4000) is added dropwise while mixing; and 10 ml of the serum-free medium is slowly added, this is followed by centrifugation. The supernatant is discarded again, and the precipitated cells are suspended in an appropriate amount of normal medium containing hypoxanthine aminopterin and thymidine (hereinafter referred to as HAT) solution and mouse interleukin-2 (hereinafter referred to as IL-2) and dispensed into individual wells of a culture plate, and cultured for about 2 weeks at 37° C. in the presence of 5% $CO_2$. During this time, HAT medium is added as necessary.

When the above myeloma cell is an 8-azaguanine resistant strain, i.e., a hypoxanthine guanine phosphoribosyl transferase (HGPRT) deficient strain, myeloma cells that did not undergo cell fusion and fused cells derived only from myeloma cells can not survive in HAT medium. On the other hand, fused cells derived from antibody-producing cells and fused cells formed from an antibody-producing cell and a myeloma cell (hybridoma) are viable in the medium, and further, fused cells derived only from antibody-producing cells gradually lose the ability to proliferate. Thus, by continuing culture of fused cells in HAT medium, desired hybridoma can be selected.

For hybridoma that have formed colonies, HAT medium is substituted with medium without aminopterin, and then an aliquot of the culture supernatant is removed so that the antibody titer can be measured. Then, a hybridoma that has been confirmed as being able to produce antibody of the present invention is transferred to another plate, and by limiting dilution, a soft agar method, a method for picking and culturing a single cell using a micromanipulator, or method for separating single cells using a cell sorter (sorter clone) etc., a single cell is obtained (cloning). The cloning procedure is repeated 2 to 4 times and hybridomas with stable antibody titers are selected as the desired hybridomas.

A hybridoma of the present invention thus obtained can be cultured in a normal medium. Furthermore, by growing a hybridoma in the peritoneal cavity of a mouse of the same strain (for example, the above BALB/c) or a Nu/Nu mouse, ascitic fluid containing a large amount of a monoclonal antibody of the present invention can be obtained. From such culture supernatant or ascitic fluid, using fractionation means well-known to those skilled in the art, an antibody of the present invention can be purified. For purification of monoclonal antibody, a commercially sold kit such as MabTrap kit (manufactured by Amersham Bioscience) can be used.

A monoclonal antibody thus obtained specifically binds to a particular polypeptide of the present invention.

For determination of the isotype and subclass of the monoclonal antibody, the Ouchterlony (Ouchterlony) method, ELISA, RIA etc. can be applied, and a commercially available kit (for example, Mouse Typer Kit; manufactured by BioRad) can be used.

A monoclonal antibody of the present invention can be provided for a purpose that uses its binding specificity, e.g. immunological detection of a polypeptide of the present invention, or purification by affinity chromatography of a polypeptide of the present invention and so on.

In the present invention, a "chimeric antibody" means a recombinant monoclonal antibody characterized in that the variable region is derived from an immunoglobulin of a non-human animal and the constant region is derived from a human immunoglobulin. A suitable chimeric antibody is a mouse/human chimeric monoclonal antibody characterized in that the variable region is derived from a mouse immunoglobulin and the constant region is derived from a human immunoglobulin. The human immunoglobulin from which the constant region is derived can be an isotypes such as IgG, IgM, IgA, IgD, IgE, with IgG and IgM being preferred. The method for producing such a chimeric antibody can be a method in which DNA coding for an antibody is isolated from a hybridoma producing a monoclonal antibody of a non-human animal, then the active VH gene (rearranged VDJ gene coding for an H chain variable region) and VL gene (rearranged VJ gene coding for an L chain variable region) are isolated from the DNA, the CH gene (C gene coding for an H chain constant region) derived from DNA coding for a human immunoglobulin and CL gene (C gene coding for an L chain constant region) are appropriately linked downstream of the VH gene and downstream of the VL gene, respectively, such that they can be functionally expressed; then, they are inserted into the same or different expression vectors, a host cell is transformed with the resulting recombinant expression vector(s), and the antibody is isolated from the culture of the resulting transformed host cell (see official gazette of provisional patent publication (KOKAI) 3-73280 etc.), but methods for producing a chimeric antibody are not limited to this method.

In the present invention, a "humanized antibody (humanized antibody obtained by CDR-grafting)" means a recombinant monoclonal antibody characterized in that a portion or all of the complementarity determining region (Complementarity-determining region: hereinafter referred to as CDR) in the variable region is derived from a monoclonal antibody of a non-human animal and a majority or all of the region other than CDR, i.e., the framework region (Framework region: hereinafter referred to as FR) of the variable region is derived from a human immunoglobulin, and the constant region is derived from a human immunoglobulin. A suitable humanized antibody is a humanized monoclonal antibody characterized in that a portion or all of the CDR is derived from a mouse monoclonal antibody, the FR is derived from a human immunoglobulin and the constant region is derived from a human immunoglobulin.

In the present invention, CDR means the region in the variable region of an antibody that is the site that directly binds to a complementary antigen.

The human immunoglobulin from which a constant region is derived can be an isotype such as IgG, IgM, IgA, IgD, IgE, with IgG and IgM being preferred. The method for producing such a humanized monoclonal antibody can be a method in which at least one mouse H chain CDR gene and at least one corresponding mouse L chain CDR gene from a hybridoma producing a mouse monoclonal antibody, and a human H chain gene coding for the entire region other than the human H chain CDR corresponding to the above mouse H chain CDR and a human L chain gene coding for the entire region other than the human L chain CDR corresponding to the above mouse L chain CDR from a human immunoglobulin gene, are respectively isolated, then the mouse H chain CDR gene and the human H chain gene, and the mouse L chain CDR gene and the human L chain gene, are appropriately linked so that they are both functionally expressed, then they are inserted into the same or different recombinant vector(s), a host cell is transformed with the resulting recombinant expression vector(s), and the antibody is isolated from the culture of the resulting transformed host cell (see official gazette of provisional patent publication (KOHYO) 4-506458, official gazette of provisional patent publication (KOKAI) 62-296890 etc.), but methods for producing humanized monoclonal antibody are not limited thereto.

In the present invention, a "human antibody" means an immunoglobulin in which all regions constituting the immunoglobulin are derived from a gene coding for a human immunoglobulin, including the variable region of the H chain and the constant region of the H chain as well as the variable region of the L chain and the constant region of the L chain. The method for producing such a human antibody can be a method in which the antibody is obtained as a polyclonal or monoclonal antibody by using a human antigen to immunologically sensitize a transgenic animal that has been produced by integrating a human immunoglobulin gene into a gene locus of the non-human mammal (see official gazette of WO94/25585, official gazette of provisional patent publication (KOHYO) 6-500233 and so on) etc., but methods for producing human antibody are not limited thereto.

In the present invention, a "fragment of an antibody" means a portion of an antibody according to the present invention, and preferably means a portion of a monoclonal antibody of the present invention. A fragment of an antibody includes a F(ab')2, Fab', Fab, Fv (variable fragment of antibody), or a scFv. "F(ab')2" and "Fab'" means an antibody fragment produced by cleavage of the disulfide bond existing between the two H chains in the hinge region by treating an immunoglobulin or monoclonal antibody with a protease or a peptidase such as pepsin, or papain.

In the present invention, an "antibody-producing cell" means a cell that produces an antibody of the present invention, preferably a monoclonal antibody or an antibody fragment of the present invention. Preferably, an antibody-producing cell is a monoclonal antibody-producing B cell derived from a non-human mammal that produces a monoclonal antibody that specifically binds to a human polypeptide having 2'-PDE activity, a hybridoma obtainable by cell fusion of a B cell with a myeloma cell derived from a mammal, a host cell retaining the gene coding for the H chain and/or the gene coding for the L chain of a monoclonal antibody isolated from the monoclonal antibody-producing B cell or the hybridoma, a host cell that can produce a chimeric antibody, a host cell that can produce a humanized antibody, a host cell that can produce a human antibody, or a host cell that can produce a single chain antibody, each of which can be produced by the above-described method.

The present invention provides a host animal into which there has been introduced a polynucleotide of the present invention. The choice of a host animal is not particularly limited, provided that it is human or a non-human mammal. The method for introducing a polynucleotide into a host animal can be an in vivo or ex vivo method (Jikken Igaku Zokan, Vol. 12 No. 15, published in 1994), a method for production of a transgenic animal (Brigid Hogan et al., translated by Kazuya Yamauchi et al., Mouse Hai No Sosa Manual, published by Kindai Shuppan Co., Ltd. in 1997; Ed. Ken Yagi, Gene Targeting No Saishin Gijutsu: Koritsuyoku Kakujitsuna Mouse No Idenshi Kumikae To Clone Sakusei-ho, published by Yodosha Co., Ltd., in 2000; Ed. Motoya Katsuki, Directed by Tatsuji Nomura, Hasseikogaku Jikken Manual: Transgenic Mouse No Tsukurikata, published by Kodansha, Ltd. in 1987) and so on.

As described above, a polypeptide provided by the present invention has 2'-PDE activity. In the present invention, 2'-PDE activity means the activity capable of catalyzing a reaction to hydrolyze the 2',5'-phosphodiester bond in an oligoribonucleotide or polyribonucleotide that has a 2',5'-phosphodiester bond as a part of its structure. In the present invention, 2'-PDE activity may be described as "the activity of the polypeptide of the present invention," "the enzyme activity of the polypeptide of the present invention," "the activity of 2'-PDE," "the enzyme activity of 2'-PDE," or simply "the activity."

In the present invention, "an oligoribonucleotide or polyribonucleotide having a 2',5'-phosphodiester bond as a part of its structure" is designated as being a "nucleotide substrate." A suitable nucleotide substrate is an oligoribonucleotide or polyribonucleotide containing adenylyl(2'-5')adenosine as a part of its structure. A more suitable nucleotide substrate is a 2',5'-oligoadenylate, such as adenylyl(2'-5')adenosine, or adenylyl(2'-5')adenylyl(2'-5')adenosine. A further more preferred nucleotide substrate of the present invention is a 2',5'-oligoadenylate in which 1, 2, 3, or 4 or more, up to 10 phosphate esters are bound at the 5'-terminus in a linear arrangement. Those with phosphate ester(s) bound at the 5'-terminus are also included in the meaning of the term 2',5'-oligoadenylate. Further, the nucleotide substrate may have an added labeling substance, compound, peptide or nucleotide that is necessary or useful for measurement of 2'-PDE activity. In the present invention, those substrates with such an added moiety are included in the meaning of the nucleotide substrate.

An oligoadenylate in which two adenosines are phosphodiester-bound between the 3' position of one adenosine and the 5' position of the other adenosine, such as adenylyl(3'-5') adenosine, adenylyl(3'-5')adenylyl(3'-5')adenosine and so on, is designated as an 3',5'-oligoadenylate in the present invention.

The activity of a polypeptide of the present invention in hydrolyzing 2',5'-oligoadenylate is similar to or greater than its activity in hydrolyzing 3',5'-oligoadenylate. Specifically, the activity in hydrolyzing 2',5'-oligoadenylate is 0.1-fold or more, preferably 0.5-fold or more, more preferably 1-fold or more, of the activity in hydrolyzing 3',5'-oligoadenylate.

There is no particular limitation of the form in which a polypeptide of the present invention is subjected to detection or measurement of 2'-PDE activity, and the polypeptide may be present in a crude fraction, a partially purified fraction, a purified specimen of polypeptide, a cell expressing the polypeptide or a host cell of the present invention. A crude fraction includes an extract, disruption product, or homogenate of a tissue or cell derived from an animal endogenously expressing a polypeptide of the present invention, a cell or tissue derived from such an animal, or from a human or a non-human mammal to which a polynucleotide of the present invention has been introduced; an extract, disruption product, or homogenate of a cell to which a polynucleotide of the present invention has been directly introduced. A partially purified fraction can be obtained by subjecting a crude fraction to various chromatography methods etc. for partial purification. A purified specimen can be obtained as a homogeneous fraction by further subjecting a partially purified fraction to various chromatography methods etc. Those various chromatography methods etc. are described in detail herein. A cell expressing a polypeptide includes a cell endogenously containing a polynucleotide of the present invention, a cell derived from human or a non-human mammal to which has been introduced a polynucleotide of the present invention.

The conditions for contacting a polypeptide of the present invention and a nucleotide substrate are not particularly limited, provided that contacting is in an aqueous solution, but the pH is normally from pH 4 to pH 10, preferably from pH 5 to 9, and more preferably from pH 6 to 8; and the temperature is normally from 0 to 50° C., preferably from 4 to 40° C., and more preferably from 20 to 37° C. The duration of contacting is normally from 30 seconds to 6 hours, preferably from 1 to 60 minutes.

Upon contacting a polypeptide of the present invention and a nucleotide substrate, it is preferred that a divalent metal ion is also present, such a metal ion can be $Mg^{2+}$, $Mn^{2+}$, $Ca^{2+}$, $Cu^{2+}$, $Zn^{2+}$, but is not limited thereto.

The 2'-PDE activity can be detected or measured as the amount of hydrolysis of a nucleotide substrate after contacting a polypeptide of the present invention and a nucleotide substrate as described above.

The amount of hydrolysis of a nucleotide substrate can be detected or measured as a decrease in the nucleotide substrate or an increase in the hydrolysis product. When the nucleotide substrate used has an added emission substance, fluorescent substance, chromogenic substance or a substance to which such a labeling substance can be bound, a decrease in the nucleotide substrate or an increase in the hydrolysis product can suitably be detected directly, or after a second reaction, using a spectrometric technique. Also, by using the ultraviolet absorption of a nucleotide substrate of a polypeptide of the present invention or a hydrolysis product thereof, fluorescence of the derivatives emitted by a particular excitation light, or fluorescence caused by a substance generated by a chemical reaction coupled with a derivatizing reaction, a decrease in the nucleotide substrate or an increase in the hydrolysis product can be detected or measured by a spectrometric technique.

When adenylyl(2'-5')adenosine, which is a more preferred substrate, is used, the hydrolysis products generated are adenosine and adenosine-5'-monophosphate (adenosine-5'-monophosphate: hereinafter referred to as AMP). AMP can be quantified by any method well-known to those skilled in the art. For example, by exposing AMP to the action of AMP deaminase (AMP deaminase), AMP is degraded to inosine-5'-monophosphate (inosine-5'-monophosphate: hereinafter referred to as IMP) and ammonia, and by quantifying the ammonia generated, an increase of AMP can be detected. For quantification of ammonia, a commercially available kit suitably can be used, such as an ammonia test kit (e.g. manufactured by Wako Pure Chemical).

When a 2',5'-oligoadenylate that does not have a phosphate group at the 5'-terminus is used as the substrate, the hydrolysis products generated by a polypeptide of the present invention include adenosine (adenosine). Adenosine can be quantified by any method well-known to those skilled in the art. For example, after adenosine is exposed to the action of adenosine deaminase (adenosine deaminase), it is degraded into inosine (inosine) and ammonia, and then by quantifying the ammonia generated, the increase in adenosine can be detected. Further, when inosine is exposed to the action of nucleotide phosphorylase (nucleotide phosphorylase) to obtain hypoxanthine (hypoxanthine), and then hydrogen peroxide is obtained by the action of xanthine oxidase (xanthine oxidase), an increase in adenosine can be detected by fluorescence of the hydrogen peroxide generated by the action of peroxidase (peroxidase) and fluorescent substrate.

When a 2',5'-oligoadenylate that has 3 phosphate groups at the 5'-terminus is used as the substrate, the hydrolysis products generated by a polypeptide of the present invention include adenosine-5'-triphosphate (adenosine-5'-triphosphate: hereinafter referred to as ATP). The ATP generated can be quantified by any method well-known to those skilled in the art. For the quantification of ATP, suitably a commercially available kit can be used, for example, the ATP emission kit (manufactured by Toyo Ink Mfg. Co., Ltd.).

When a nucleotide substrate is used which is designed to emit fluorescence under a specific excitation light, color development or light emission as a result of being hydrolyzed by a polypeptide of the present invention, an increase in the hydrolysis products can be detected. Such a nucleotide substrate can include, for example, those nucleotide substrates which are designed so that, by undergoing hydrolysis, fluorescence energy transition does not occur and fluorescence of fluorescein (Fluorescein) is generated. Alternatively, when a nucleotide substrate is designed so that it does not generate color development, light emission, or florescence under a specific excitation light on hydrolysis, a decrease in the nucleotide substrate can be detected.

Using a nucleotide substrate labeled with a radioactive substance, a decrease in a nucleotide substrate or an increase in a hydrolysis product(s) can be detected as a decrease or increase in the radiation or liquid scintillation count. Using a mass spectrometric analysis, a decrease in a nucleotide substrate or an increase in hydrolysis product(s) can be detected as a decrease or increase in the mass spectrum peak(s).

Further, simultaneously with, or after, contacting a polypeptide of the present invention and a nucleotide substrate, instead of detection or measurement of 2'-PDE activity, RNase L and RNA can be added and this can be followed by detecting or measuring the activation of RNase L by using RNA degradation as an indicator. Similarly, simultaneously with, or after, contacting a cell endogenously having a polynucleotide of the present invention and a nucleotide substrate, instead of detection or measurement of 2'-PDE activity, a virus can be added, and this can be followed by detecting or measuring the amount or the proliferation of the virus after a certain period of incubation. Alternatively, when the cell to be contacted with the nucleotide substrate is a cell endogenously having a polynucleotide of the present invention and which already contains RNase L, RNA, or a virus, a similar detection or measurement can be conducted without the need for further addition of Rnase L, RNA or a virus. For example, when a cell in which the 2-5A system is activated, or a cell infected with a virus, is contacted with a nucleotide substrate, there is no need to add RNase L, RNA or a virus exogenously.

For detecting or measuring a decrease in a nucleotide substrate or an increase in a hydrolysis product(s), protein component(s) can be removed beforehand from the analyte sample, as necessary. The protein components can be removed by a procedure such as centrifugation, membrane filtration or the like or as an insoluble fraction generated by the addition of an acid, such as trichloroacetic acid etc. Furthermore, upon detecting a decrease in a nucleotide substrate or an increase in hydrolysis product(s), the nucleotide substrate and the hydrolysis product(s) can be separated from each other, as necessary. When a decrease in the nucleotide substrate is detected, it is preferred that the nucleotide substrate is separated from the hydrolysis product(s). When the hydrolysis product(s) is detected, it is preferred that at least the hydrolysis product to be detected is separated from the nucleotide substrate. Adding an appropriate tag etc. on the nucleotide substrate in advance is useful for conducting such separation. When high performance liquid chromatography (high performance liquid chromatography: HPLC) etc. is used, separation of the substrate and the hydrolysis product(s) and detection can be performed in parallel.

The amount of transcription of a polynucleotide of the present invention can be measured by any method well known to those skilled in the art, and such methods include hybridization methods such as dot blot, slot blot, and Northern blotting (northern blotting), using a polynucleotide of the present invention or a fragment thereof as the probe for total RNA, mRNA, or a cDNA library prepared using mRNA as the template; polymerase chain reaction (polymerase chain reaction: hereinafter referred to as PCR), reverse transcription PCR (reverse transcription PCR: hereinafter referred to as RT-PCR), Taqman (Taqman) PCR, or competitive PCR, that uses a cDNA library prepared using them as the template and uses an oligonucleotide designed so that a polynucleotide of the present invention or a fragment thereof will be amplified; a microarray method, a gene chip (genechip) method and so on. Further, by conducting in situ (in situ) hybridization on a tissue slice using a probe as described above, transcription of a polynucleotide of the present invention in a tissue can be detected or measured.

The amount of translation of a polypeptide of the present invention can be measured by any method well-known to those skilled in the art, and such methods can be, for example, various immunoassays (immuno assay) or a Western blotting method (western blotting) etc., that uses a monoclonal antibody, or a fragment thereof or a single chain antibody (scFv), polyclonal antibody or anti-serum that specifically binds to a polypeptide of the present invention against a sample such as a cell, tissue, body fluid and so on or a fraction thereof derived from human or a non-human mammal. Immunoassays can be exemplified by ELISA, EIA, sandwich EIA, RIA, and so on. Further, by staining a tissue slice, a polypeptide of the present invention in a tissue can be detected or measured.

The present invention provides a process for screening for a 2'-PDE activity modulator substance. The process comprises a step of detecting or measuring the above described 2'-PDE activity in the presence or absence of a specimen. Specifically, in the presence or absence of a specimen, a polypeptide of the present invention or a host cell of the present invention is contacted with a nucleotide substrate, the amount of hydrolysis of the nucleotide substrate is measured by a method as described above, and if the amount of hydrolysis in the presence of the specimen is changed compared to that in the absence of the specimen, the specimen can be judged as being a 2'-PDE activity modulator substance. Meanwhile, if the amount of hydrolysis in the presence of a specimen is less than that in the absence of the specimen, the specimen can be judged as being a 2'-PDE activity inhibitor substance. On the other hand, if the amount of hydrolysis in the presence of a specimen is greater than that in the absence of the specimen, the specimen can be judged as being a 2'-PDE activity enhancer substance. A host cell used in a screening method, is preferably one functionally expressing a polypeptide of the present invention.

The present invention provides a process for screening for a 2'-PDE expression modulator substance. The process comprises a step of measuring the amount of transcription of a polynucleotide of the present invention or the amount of translation of a polypeptide of the present invention in the presence or absence of a specimen. Specifically, in the presence or absence of a specimen, a host cell of the present invention or a cell endogenously carrying a polynucleotide of the present invention is incubated, then the amount of transcription of the polynucleotide of the present invention or the amount of translation of the polypeptide of the present invention in the cell or in the extracellular solution is measured, and if the amount of transcription or the amount of translation in the presence of the specimen is changed compared to that in the absence of the specimen, the specimen can be judged as being a 2'-PDE expression modulator substance. If the amount of transcription or the amount of translation in the presence of a specimen is less that in the absence of the specimen, the specimen can be judged as being a 2'-PDE expression suppressor substance. On the other hand, if the amount of transcription or the amount of translation in the presence of a specimen is greater than that in the absence of the specimen, the specimen can be judged as being a 2'-PDE expression enhancer substance. A host cell used in the screening method, is preferably one in which a polynucleotide of the present invention is transcribed or a polypeptide of the present invention is translated.

When a cell or host cell is incubated in a screening method of the present invention, it can be incubated in the presence and/or absence of interferon. By doing so, it is possible to distinguish between, and efficiently select, a substance which alone exerts a desired biological activity, a substance which alone does not exert a desired biological activity but enhances the action of interferon, a substance which alone exerts a desired biological activity and enhances the action of interferon, a substance which alone does not exert a desired biological activity but suppresses or inhibits the action of interferon, a substance which alone exerts a desired biological activity and suppresses or inhibits the action of interferon, and so on.

The present invention provides a process for screening for a 2'-PDE binding substance. The process can be performed by directly measuring the affinity or binding ability of a specimen to a polypeptide of the present invention, or by measuring competitive inhibition activity for binding of the polypeptide and the substrate or ligand. The polypeptide of the present invention provided for the process is similar to those used for the detection or measurement of the 2'-PDE activity.

The method for measuring affinity or binding ability of a specimen to the polypeptide of the present invention is not particularly limited, as long as it is a method well-known to those skilled in the art that can be used for the measurement of the affinity or binding ability between two substances. For example, by using an NMR method to detect the presence or absence of a chemical shift change or by performing a mass spectrometric analysis, free polypeptide that is not bound to a specimen and polypeptide that is bound to a specimen can be distinguished.

Competitive inhibition of binding of a substrate or ligand by binding of a polypeptide of the present invention can be measured normally by a method well-known to those skilled in the art that measures competitive inhibition of the binding of an enzyme protein and its substrate or of binding of a receptor protein and its ligand. As such a method, for example, an above-described detection or measurement method for 2'-PDE activity can be applied. Thus, a specimen that competitively inhibits 2'-PDE activity can be regarded as having an affinity or binding ability for a polypeptide of the present invention.

Those 2'-PDE binding substances thus screened include a nucleotide specifically hydrolyzed by 2'-PDE, an endogenous or exogenous ligand of 2'-PDE, a 2'-PDE activity modulator substance, and so on.

The specimen subjected to a screening method provided by the present invention is in no way limited, and includes a chemically synthesized compound, a compound separated from a natural sample, a culture of a microorganism, an extract or fraction thereof, an extract derived from an animal or plant or fraction thereof, a mixture of these, and so on. The term "compound" as used herein includes a low molecular weight compound, peptide, nucleotide, hydrocarbon, lipid, polymer and so on. The specimen may be any of a crude fraction such as an extract, partially purified fraction, purified specimen and so on. Further, the specimen may be immobilized directly or indirectly via a spacer etc., to a barely soluble or insoluble carrier.

The present invention provides a process for detecting 2'-PDE activity. The process comprises a step of measuring 2'-PDE activity contained in an analyte sample.

The present invention provides a process for detecting expression of 2'-PDE activity. The process comprises a step of measuring the amount of transcription of polynucleotide of the present invention or the amount of translation of a polypeptide of the present invention contained in an analyte sample.

A sample subjected to a process for detection provided by the present invention can include a sample such as a cell, tissue, organ, body fluid or feces derived from a human or a non-human animal; a host cell of the present invention; a cell, tissue, organ, body fluid or feces derived from a host animal of the present invention; a fraction of any of these, a partially-purified fraction or purified fraction derived from that fraction, and so on. The purified fraction can be a purified peptide, nucleotide, and so on. An analyte sample derived from a plant or microorganism is also included.

The present invention provides a kit used for performing an above-described screening process, i.e., a screening kit.

A screening kit for a 2'-PDE activity modulator substance of the present invention includes a polypeptide of the present invention or a host cell of the present invention, and a nucleotide substrate of the present invention.

A screening kit for a 2'-PDE expression modulator substance of the present invention includes at least one element selected from the group consisting of those below in [a] to [d]:

[a] a polynucleotide of the present invention or a fragment thereof, that can be used as a hybridization probe;

[b] an oligonucleotide containing at least 10 bases, that can be used as a primer for replication or amplification of a polynucleotide of the present invention or a fragment thereof, and that has a portion of a nucleotide sequence of a polynucleotide of the present invention or a nucleotide sequence entirely complementary thereto and which can hybridise with the sense strand or anti-sense strand of the polynucleotide. As the PCR primers, it is preferred that two oligonucleotides are designed so that the sense strand and the anti-sense strand of a polynucleotide of the present invention or a fragment thereof are amplified;

[c] an isolated antibody that can be used as a probe for detection of a polypeptide of the present invention by an immunoassay (Immunoassay) and that specifically binds to a polypeptide of the present invention, an active fragment thereof, an chimeric antibody thereof, an humanized antibody thereof, an complete human antibody or a single chain antibody thereof;

[d] an insoluble carrier to which one element selected from the group consisting of a polynucleotide as described in [a] or a fragment thereof, an oligonucleotide as described in [b], an antibody as described in [c], an active fragment thereof, a chimeric antibody thereof, a humanized antibody thereof, a human antibody thereof, or a single chain antibody thereof, has been bound directly or indirectly via a spacer etc. The insoluble carrier can be a bead consisting of an organic polymer or glass, a plate, a well of a plate etc., SPA beads, a carrier for a DNA tip, a carrier for a microarray etc.

Such a screening kit may further contain an item that is necessary or useful for detection or measurement using any of [a] to [d]. Those items include a substance necessary for a label required for detection or measurement, a substance necessary for detection, a standard substance necessary for quantification, interferon, and so on. Further, an element as described in [a] to [d] may be labeled in advance, or may be processed in advance so that it can be readily labeled.

A screening kit for a 2'-PDE binding substance of the present invention includes a polypeptide of the present invention, and preferably includes a nucleotide substrate of the present invention.

The above screening kit of the present invention is also included in the present invention as a kit for detection of 2'-PDE activity, a kit for detection of 2'-PDE expression, or a kit for detection of 2'-PDE binding.

A substance obtainable by a screening process of the present invention is useful for improvement or modification of various diseases or biological conditions. A 2'-PDE activity inhibitor substance, 2'-PDE binding substance, 2'-PDE expression suppressor substance and so on are useful for activation of the 2-5A system, and for the treatment or prevention of 2-5A system sensitive diseases.

In the present invention, the "2-5A system" means the biological protection mechanism in which 2'-PDE and the endogenous nucleotide substrate (2',5'-oligoadenylate) are directly or indirectly involved, and a "2-5A system sensitive disease" is a disease in which symptoms can be mitigated or improved, or the disease prevented, due to activation of the 2-5A system, such diseases include viral infections, tumors and so on. The present invention provides methods for treating or preventing such diseases in a human.

Viral infections included as 2-5A system sensitive diseases include infections sensitive to interferon such as those caused by *Picornaviridae* (Picornaviridae), *Orthomyxoviridae* (Orthomyxoviridae), *Retroviridae* (Retroviridae), *Poxyiridae* (Poxyiridae), *Herpesviridae* (Herpesviridae), *Adenoviridae* (Adenoviridae), *Papovaviridae* (Papovaviridae), *Paramyxoviridae* (Paramyxoviridae), *Flaviviridae* (Flaviviridae) and so on (written by S. J. Flint et al., Principles of Virology: Molecular Biology, Pathogenesis, and Control, published in the United States by American Society for Microbiology, in 1999), and those viruses pathogenic to humans are exemplified by poliovirus (poliovirus) or rhinovirus (rhinovirus), which are species of *Picornaviridae*; influenza virus (influenza virus), which is a species of *Orthomyxoviridae*; human T cell leukemia virus (human T cell leukemia virus) and human immunodeficiency virus (human immunodeficiency virus), which are species of *Retroviridae*; smallpox virus (smallpox virus), which is a species of *Poxyiridae*; Herpes simplex virus (Herpes simplex virus) 1 and 2, Varicella zoster virus (human herpes virus 3), Cytomegalovirus (cytomegalovirus) and EB virus (EB (Epstein-Barr) virus), which are species of *Herpesviridae*; human adenovirus (human adenovirus) 1 to 47, which are species of *Adenoviridae*; human papilloma virus (human papilloma virus), which is a species of *Papovaviridae*; measles virus (measles virus), mumps virus (mumps virus), and respiratory syncytial virus (respiratory syncytial virus), which are species of *Paramyxoviridae*; hepatitis C virus (hepatitis C virus), which is a species of *Flaviviridae*; and so on (Ed. Shoichi Hatanaka, Virus-gaku, published by Asakura-shoten Co., Ltd. in 1997).

Tumors included as 2-5A sensitive diseases include sarcomas, carcinomas, leukemia and so on, and more specifically, can be exemplified by fibrosarcoma, liposarcoma, osteosarcoma, angiosarcoma, multiple myeloma, malignant melanoma, glioma, pulmonary carcinoma, gastric carcinoma, carcinoma of colon, mammary carcinoma, prostatic carcinoma, renal carcinoma, pancreatic carcinoma, cancer of liver, esophageal carcinoma, tongue carcinoma, cerebral tumor, pharyngeal carcinoma, cystocarcinoma, ovarian carcinoma, skin carcinoma, acute leukemia, chronic leukemia, lymphomatosis, glioblastoma and so on, and preferably multiple myeloma, renal carcinoma, prostatic carcinoma, malignant melanoma, glioblastoma and so on (Editor in Chief: Shigeru Goto, Saishin Igaku Daijiten, 2nd edition, P. 115, published by Ishiyaku Publishers, Inc., in 1996).

Further, 2-5A sensitive diseases also include osteoporosis, rheumatoid arthritis, various osteopenia, renal osteodystrophy, hypercalcemia, various tumors and associated bone metastases, and so on, as well as bone resorption diseases.

2'-PDE activity enhancer substances, 2'-PDE binding substances, and 2'-PDE expression enhancer substances are useful for inactivation of the 2-5A system, immunosuppression, and so on.

Thus, a process for screening for a 2'-PDE activity modulator substance, a process for screening for a 2'-PDE expression modulator substance, and a process for screening for a 2'-PDE binding substance, provided by the present invention, are all included in the present invention as processes for screening for a 2-5A system modulator substance. Among these, processes for screening for 2'-PDE activity inhibitor substances and processes for screening for 2'-PDE expression suppressor substances are suitable as processes for screening for 2-5A system activator substances, and processes for screening for 2'-PDE activity enhancer substances and processes for screening for 2'-PDE expression enhancement substances are suitable as processes for screening for 2-5A system inactivator substances. Further, processes for screening for 2'-PDE activity inhibitor substances and processes for screening for 2'-PDE expression suppressor substances are suitable as processes for screening for 2-5A sensitive disease therapeutic or preventive agents, and processes for screening for 2'-PDE activity enhancer substances and processes for screening for 2'-PDE expression enhancer substances are suitable as processes for screening for immunosuppressive agents.

Similarly, screening kits for 2'-PDE activity modulator substances, screening kits for 2'-PDE expression modulator substances, and screening kits for 2'-PDE binding substances, provided by the present invention, are all included in the present invention as screening kits for 2-5A system modulator substances. Among these, screening kits for 2'-PDE activity inhibitor substances and screening kits for 2'-PDE expression suppressor substances are suitable as screening kits for 2-5A system activator substances, and screening kits for 2'-PDE activity enhancer substances and screening kits for 2'-PDE expression enhancer substances are suitable as screening kits for 2-5A system inactivator substances. Further, screening kits for 2'-PDE activity inhibitor substances and screening kits for 2'-PDE expression suppressor substances are suitable as screening kits for 2-5A sensitive disease therapeutic preventive agents, and screening kits for 2'-PDE activity enhancer substances and screening kits for 2'-PDE expression enhancer substances are suitable as screening kits for immunosuppressive agents.

Substances obtainable by a screening method of the present invention are also included in the scope of the present invention. Those substances include antibody that specifically binds to a polypeptide of the present invention and that can inhibit 2'-PDE activity (neutralizing antibody), an active fragment, chimeric antibody, humanized antibody, complete human antibody, single chain antibody or active derivative thereof; an anti-sense nucleotide; a ligand of a polypeptide of the present invention, and so on.

The present invention provides an anti-sense nucleotide that is complementary to a portion or all of a polynucleotide of the present invention. There is no particular limitation on the anti-sense nucleotide, as long as it is at least 10 contiguous nucleotides that exist in a polynucleotide comprising a nucleotide sequence that is 80% or more identical to the nucleotide as set forth in Sequence ID No. 1 of the Sequence Listing or a nucleotide sequence completely complementary thereto, and it is a nucleotide that suppresses or inhibits transcription by hybridizing with a polynucleotide of the present invention. In a preferred anti-sense nucleotide, the 3'-terminal nucleotide is identical to the corresponding nucleotide in a polynucleotide consisting of the nucleotide sequence as set forth in Sequence ID No. 1 of the Sequence Listing. A more preferable anti-sense nucleotide is at least 10 contiguous nucleotides existing in a polynucleotide consisting of the nucleotide sequence as set forth in Sequence ID No. 1 in the Sequence Listing or a completely complementary nucleotide sequence thereto. Such an anti-sense nucleotide is useful as a 2-5A system activating agent, as a 2-5A system sensitive disease therapeutic or preventive agent, or for functional analysis of a polypeptide of the present invention, and so on.

The present invention provides a small interfering RNA (small interfering RNA: siRNA) comprising a portion or all of a polynucleotide of the present invention. A siRNA normally consists of a complementary double-stranded oligonucleotide in which one of the nucleotide chains consists of at least 10 contiguous nucleotides existing in a polynucleotide consisting of nucleotide sequence that is 80% or more identical to a nucleotide sequence completely complementary to the nucleotide sequence as set forth in Sequence ID No. 1 of the Sequence Listing, and which is capable of inactivating a polynucleotide of the present invention via hybridization with a polynucleotide of the present invention.

In a preferred siRNA, the $_5$'- and/or 3'-terminal nucleotides are identical to the corresponding nucleotides in a polynucleotide comprising the nucleotide sequence as set forth in Sequence ID No. 1 of the Sequence Listing. A more preferable siRNA is 10 to 30 contiguous nucleotides existing in a polynucleotide consisting of the nucleotide sequence as set forth in Sequence ID No. 1 of the Sequence Listing or a nucleotide sequence completely complementary thereto. Such an siRNA is useful as a 2-5A system activator agent, 2-5A system sensitive disease therapeutic or preventive agent, or for functional analysis of the polypeptide of the present invention, and so on.

A substance obtainable by a screening process of the present invention, a polypeptide, polynucleotide, antibody, or active fragment thereof, chimeric antibody thereof, humanized antibody thereof, human antibody or single chain antibody thereof, anti-sense nucleotide or siRNA, provided by the present invention (hereinafter referred to as a "pharmaceutical component of the present invention"), can be safely administered as a pharmaceutical composition to a human or a non-human animal, either orally or parenterally. A pharmaceutical composition containing a substance obtained by a screening method of the present invention is included in the scope of the present invention. The form of administration of the pharmaceutical composition can be selected as appropriate depending on the type of disease, the severity of disease, symptoms, age, gender, and/or body weight of the subject to be treated and so on. For example, tablets, capsules, granules and syrup are orally administered, injectable formulations are administered i.v. either alone or after being mixed with a normal auxiliary solution such as glucose, amino acid and so on, or administered alone intramuscularly, subcutaneously, intracutaneously, or intraperitoneally; patches are administered transdermally, collunaria are administered pernasally, mucosal application agents are administered transmucosally or orally, and suppositories are administered intrarectally. These pharmaceuticals can be formulated according to a conventional method using known auxiliary agents (i.e., carriers) normally employed in the art of pharmaceutical production, such as fillers, binders, disintegrants, lubricants, flavorings, solubilizers, suspensions, color additives, pH buffers, preservatives, gelling agents, detergents, coating agents, and so on. The amount of the substance obtained by a screening process of the present invention which is present in those pharmaceutical compositions is not particularly limited, but would normally be from 0.1 to 70% by weight, with 1 to 30% by weight being preferred.

The dosage of a pharmaceutical component of the present invention depends on the symptoms, age, body weight, form of administration, agent form and so on, but, for example, normally the upper limit of the dosage per day for an adult human is 10 to 1000 mg, and the lower limit is 0.001 to 0.1 mg. The frequency of administration of the substance depends on the form of administration, agent form, and so on, but can be once in several days, one a day, or several times per day.

Further, a 2-5A system activator agent containing a pharmaceutical component of the present invention as the active ingredient, a therapeutic agent or preventive agent for a 2-5A system sensitive disease, use of a pharmaceutical component of the present invention for activating the 2-5A system, use of a pharmaceutical component of the present invention for preventing or treating a 2-5A system sensitive disease, use of a pharmaceutical component of the present invention for producing a 2-5A system activator agent, use of a pharmaceutical component of the present invention for producing a therapeutic agent or preventive agent for a 2-5A system sensitive disease, a process for activating the 2-5A system consisting of administering a pharmaceutical component of the present invention, a process for treating a 2-5A sensitive disease consisting of administering a pharmaceutical component of the present invention, and so on are also included in the present invention.

Further, administration a pharmaceutical component of the present invention as a pharmaceutical composition to a human or a non-human mammal, may be in combination with other pharmaceuticals and those other pharmaceuticals, such as interferon (interferon), a substance that enhances interferon production, a substance that enhances interferon activity, any other anti-viral agent or other anti-tumor agent; as interferon, human interferon-$\alpha$, -$\beta$, and -$\gamma$ are preferred.

The present invention provides a process for increasing the amount of 2',5'-oligoadenylate, a process for activating RNase L, and a process for activating the 2-5A system. Specifically, using a substance obtained by using a screening method of the present invention, an antibody of the present invention, or an anti-sense nucleotide of the present invention, by inhibiting 2'-PDE activity in a cell, tissue or body fluid derived from a human or a non-human mammal, or by decreasing the amount of transcription of a nucleotide of the present invention or the amount of translation of a polypeptide of the present invention, the amount of 2',5'-oligoadenylate in the animal, cell, tissue or body fluid can be increased, thereby activating RNase L and further activating the 2-5A system.

Further, in the genomic DNA contained in an animal, cell, tissue or body fluid, by deleting a portion or all of a polynucleotide of the present invention or by mutating the polynucleotide so that the 2'-PDE activity of the polypeptide coded by the polynucleotide is partially or totally lost, it is possible to increase the amount of 2',5'-oligoadenylate. To introduce a mutation into genomic DNA, any method well-known to those skilled in the art, such as site-directed mutagenesis (site-directed mutagenesis) and so on, can be suitably used (Martin J. T. and Ismail K., Gene Knockout Protocols, Humana Press, U.S.A. (2001); Shinichi Aizawa, Gene Targeting: ES saibo wo mochiita heni mouse no sakusei, published by Yodosha Co., Ltd. in 1995; Brigid Hogan et al., translated by Kazuya Yamauchi et al., Mouse hai no sosa manual, published by Kindai Shuppan in 1997; Ed. Ken Yagi, Gene Targeting no saishin gijutsu: Koritsu yoku kakujitsuna mouse no idenshi kumikae to clone sakuseiho, published by Yodosha Co., Ltd., in 2000).

These methods are also useful as processes for activating the 2-5A system or as processes for treating 2-5A system sensitive diseases and so on.

As described above, a polypeptide of the present invention can specifically hydrolyze a nucleotide containing a 2',5'-phosphodiester bond as a part of its structure. Using that activity, it is possible to generate nucleotides or derivatives thereof that have been difficult to produce conventionally.

The present invention provides a process for assessing the degree of activation of the 2-5A system. The process comprises a step of measuring the amount of transcription of a polynucleotide of the present invention, the amount of translation of a polypeptide of the present invention, the 2'-PDE activity and so on in an analyte sample. For example, when the amount of transcription or the amount of translation in an analyte sample derived from a subject individual or subject mammal, or a sample derived from a healthy individual or a healthy mammal (control sample) is measured and the amount of transcription or the amount of translation in the analyte sample is less than that in the control sample, the 2-5A system is judged as being activated in the subject individual or subject mammal. Similarly, when the 2'-PDE activity in an analyte sample derived from a subject individual or subject mammal, or a sample derived from a healthy individual or healthy mammal (control sample) is measured and the 2'-PDE activity in the analyte sample is less than that in the control sample, the 2-5A system is judged as being activated in the subject individual or subject mammal. Conversely, when the amount of transcription or the amount of translation in the analyte sample is greater than that in the control sample, the 2-5A system is judged as being inactivated in the subject individual or subject mammal. Similarly, when the 2'-PDE activity in the analyte sample is greater than that in the control sample, the 2-5A system is judged as being inactivated in the subject individual or subject mammal.

In the present invention, when the amount of transcription of a polynucleotide of the present invention in the analyte sample is less than that in the control sample, or when the amount of translation of a polypeptide of the present invention is less than that in the control sample, or when the 2'-PDE activity is less than that in the control sample, or when the amount of 2',5'-oligoadenylate is greater than that in the control sample, or when the amount of RNA degradation by RNase L is greater than that in the control sample, or when the amount of protein synthesis is reduced compared to the control sample, or when the rate of cell proliferation is lower than that in the control sample, it is said that the 2-5A system is activated. Conversely, compared to the control sample, when the amount of transcription of the polynucleotide of the present invention in the analyte sample is greater than that in the control sample, or when the amount of translation of the polypeptide of the present invention is greater than that in the control sample, or when the 2'-PDE activity is higher than that in the control sample, or when the amount of 2',5'-oligoadenylate is lower than that in the control sample, or when the amount of RNA degradation by RNase L is lower than that in the control sample, or when the amount of protein synthesis is higher than that in the control sample, or when the rate of cell proliferation is higher than that in the control sample, it is said that the 2-5A system is inactivated.

The 2-5A system can be activated or inactivated endogenously in those suffering from 2-5A system sensitive diseases, such as viral infections, tumors and so on. Thus, a process for assessing the degree of activation of the 2-5A system is included in the present invention also as a process for assessing the risk of suffering from 2-5A system sensitive disease. When the 2-5A system is found to be activated in a subject individual (as used herein, "individual" refers to a human) or subject mammal, it is judged that the subject individual or subject mammal has a lower risk of suffering from a 2-5A system sensitive disease. Conversely, when the 2-5A system is found to be inactivated in a subject individual or subject mammal, it is judged that the subject individual or subject mammal has a higher risk of suffering from a 2-5A system sensitive disease.

Further, before and after a pharmaceutical component of the present invention is administered to a subject individual or subject mammal, the degree of activation of the 2-5A system can be measured, and, if the degree of activation after administration is higher than that before administration, then the 2-5A system activation effect or the 2-5A system sensitive disease therapeutic effect or preventive effect of the pharmaceutical component in the subject individual or mammal can be judged as being high. Alternatively, if the degree of activation after administration is lower than, or similar to that before administration, the 2-5A system activation effect or the 2-5A system sensitive disease therapeutic effect or preventive effect of the pharmaceutical component in the subject individual or subject mammal can be judged as being low. The present invention includes a process for assessing the effectiveness of a 2-5A system activating agent, or of a 2-5A system sensitive disease therapeutic agent or preventive agent.

Before and after a pharmaceutical component of the present invention is administered to a subject individual or subject mammal the amount of activation of the 2-5A system is measured, and, if the degree of activation after administration is higher than, or similar to that before administration, the 2-5A system inactivating effect or immunosuppressive effect of the pharmaceutical component on the subject individual or subject mammal can be judged as being low. Alternatively, if the degree of activation after administration is lower than that before administration, the 2-5A system inactivating effect or immunosuppressive effect of the pharmaceutical component in the subject individual or subject mammal can be judged as being high. The present invention includes a process for assessing the effectiveness of a 2-5A system inactivating agent, immunosuppressive agent, and so on.

Further, compared to a healthy individual or healthy mammal, in the subject individual or subject mammal, when the amount of transcription of a polynucleotide of the present invention is higher, when the amount of translation of a polypeptide of the present invention is higher, or the 2'-PDE activity is higher, it can be predicted that the 2-5A system activating effect, or the 2-5A system sensitive disease therapeutic or preventive effect that can be exerted by the 2'-PDE activity inhibitor substance of the present invention in the subject individual or subject mammal will be high. Conversely, in the subject individual or subject mammal, when the amount of transcription of a polynucleotide of the present invention is lower, when the amount of translation of a polypeptide of the present invention is lower, or when the 2'-PDE activity is lower, it can be predicted that the 2-5A system activating effect, or the 2-5A system sensitive disease therapeutic or preventive effect that can be exerted by the 2'-PDE activity inhibitor substance of the present invention in a subject individual or subject mammal will be low.

Compared to a healthy individual or healthy mammal, in a subject individual or subject mammal, when the amount of transcription of a polynucleotide of the present invention is higher, or when the amount of translation of a polypeptide of the present invention is higher, it can be predicted that the 2-5A system activating effect or the 2-5A system sensitive disease therapeutic or preventive effect that can be exerted by the 2'-PDE expression suppressive substance of the present invention in the subject individual or subject mammal will be high. Conversely, in the subject individual or subject mammal, when the amount of transcription of a polynucleotide of the present invention is lower, or when the amount of translation of a polypeptide of the present invention is lower, it can be predicted that the 2-5A system activating effect or the 2-5A system sensitive disease therapeutic or preventive effect that can be exerted by the 2'-PDE expression suppressive substance of the present invention in the subject individual or subject mammal will be low.

Such a process for predicting the effect of a 2-5A system activating agent, 2-5A system sensitive disease therapeutic agent or preventive agent, and so on is also included in the scope of the present invention.

Further, compared to a healthy individual or healthy mammal, in the subject individual or subject mammal, when the amount of transcription of a polynucleotide of the present invention is higher, when the amount of translation of a polypeptide of the present invention is higher, or when the 2'-PDE activity is higher, it can be predicted that the 2-5A system inactivating effect or immunosuppressive effect that can be exerted by the 2'-PDE activity enhancer substance of the present invention in the subject individual or subject mammal will be high. Conversely, in the subject individual or subject mammal, when the amount of transcription of a polynucleotide of the present invention is lower, when the amount of translation of a polypeptide of the present invention is lower, or when the 2'-PDE activity is lower, it can be predicted that the 2-5A system inactivating effect or immunosuppressive effect that can be exerted by the 2'-PDE activity enhancer substance of the present invention in the subject individual or subject mammal will be low.

Compared to a healthy individual or healthy mammal, in the subject individual or subject mammal, when the amount of transcription of a polynucleotide of the present invention is lower, or when the amount of translation of a polypeptide of the present invention is lower, it can be predicted that the 2-5A system inactivating effect or immunosuppressive effect that can be exerted by the 2'-PDE expression enhancer substance of the present invention in the subject individual or subject mammal will be high. Conversely, in a subject individual or subject mammal, when the amount of transcription of a polynucleotide of the present invention is higher, or when the amount of translation of a polypeptide of the present invention is higher, it can be predicted that the 2-5A system inactivating effect or immunosuppressive effect that can be exerted by the 2'-PDE expression enhancer substance of the present invention in the subject individual or subject mammal will be low.

Such a process for predicting the effect of a 2-5A system inactivator agent, immunosuppressive agent and so on is also included in the scope of the present invention.

The subject individual or subject mammal in a process for assessment or a process for prediction according to the present invention is not limited, as long as it is the same species as the control healthy individual or healthy mammal, but it is preferred that the gender, age, weeks after birth, disease history and so on are the same as for the healthy individual or healthy mammal.

For performing a process for detection, a process for assessment, or a process for prediction of the present invention, suitably a screening kit provided by the present invention can be used. Thus, a screening kit of the present invention is included also in the present invention as a kit for detecting 2'-PDE activity, a kit for detecting 2'-PDE expression, a kit for assessing the amount of activation of the 2-5A system, a kit for assessing the risk of suffering from a 2-5A system sensitive disease, a kit for assessing the effectiveness of a 2-5A system activator agent, a 2-5A system sensitive disease therapeutic agent or preventive agent, a kit for predicting the effect of a 2-5A system sensitive disease therapeutic agent or preventive agent, a kit for assessing the effectiveness of a 2-5A system inactivator agent or immunosuppressive agent, a kit for predicting the effectiveness of an immunosuppressive agent, and so on.

Processes for assessing and processes for prediction of the present invention are also useful as processes for diagnosis of 2-5A system sensitive diseases etc., and such processes for diagnosis are also included in the present invention. Similarly, a screening kit of the present invention is included in the present invention also as a screening kit for diagnosis according to the present invention.

In the following examples and test examples, the present invention is described in more detail and more specifically, but the present invention is not limited to the examples described.

EXAMPLES

Example 1

Partial Purification of 2'-PDE from Bovine Liver

All the manipulations of the present example were performed at 4° C., except SDS-polyacrylamide gel electrophoresis and staining of the gel.

To 200 g of finely chopped bovine liver, 700 ml of Buffer 1 [composition: 10 mM MOPS (pH 7.4), 10 mM $MgCl_2$, 40 mM NaCl, 0.2 mM dithiothreitol (DTT), 0.1 mM PMSF] was added. After homogenization using Polytron homogenizer (manufactured by KINEMATICA), the homogenate was subjected to centrifugation at 15,000×g for 20 min. and then the supernatant was recovered and subjected to a further centrifugation at 100,000×g for 60 min. To the resulting supernatant, ammonium sulfate was added to 30% saturation. After stirring for 20 min., the supernatant/ammonium sulphate solution was subjected to centrifugation at 15,000×g for 20 min. The supernatant, to which ammonium sulfate was further added to 50% saturation, was stirred for 12 hours and then subjected to centrifugation at 9,000×g for 60 min. to recover the pellet.

The pellet was resuspended by adding 200 ml of Buffer 2 [composition: 20 mM HEPES (pH 7.0), 5 mM $MgCl_2$, 1 mM DTT] containing a protease inhibitor, Complete™ solution (manufactured by Roche Diagnostics), and dialyzed against 10 L of Buffer 2 for 3 hours, and then against 10 L of Buffer 3 [composition: 20 mM HEPES (pH 7.0), 5 mM $MgCl_2$, 1 mM DTT, 2 M NaCl] for 12 hours, using a dialysis membrane with the molecular weight cut off of 7,000 (manufactured by Pierce). The resulting dialysis inner solution was centrifuged at 28,000×g for 15 min. and the supernatant was filtered using a 0.2 μm filter to remove the precipitates.

The dialysis inner solution thus obtained was loaded onto a hydrophobic interaction column (HiPrep 16/10 Phenyl FF (High sub): manufactured by Amersham Bioscience, i.e., manufactured formerly by Amersham Pharmacia Biotech K.K.) which had been equilibrated in advance with Buffer 3. After the column was washed with 250 ml of Buffer 3, the components adsorbed to the column were eluted with a linear gradient of 50 ml of Buffer 3 and 50 ml of Buffer 2, and subsequently with 100 ml of Buffer 2. 2'-PDE activity was measured in each of the eluted fractions. Using a dialysis membrane with a molecular weight cut off of 7000, 90 ml of the active fraction was dialyzed against 2 L of Buffer 4 [composition: 20 mM HEPES (pH 7.0), 5 mM $MgCl_2$, 1 mM DTT, 0.05% (W/V) CHAPS] for 12 hours.

The resulting dialysis inner solution was loaded onto a dye-bound affinity column (HiTrap Blue HP 5 ml: manufactured by Amersham Bioscience) which had been equilibrated in advance with Buffer 4. After the column was washed with 50 ml of Buffer 4, the components adsorbed to the column were eluted with a linear gradient of 12.5 ml of Buffer 4 and 12.5 ml of Buffer 5 [composition: 20 mM HEPES (pH 7.0), 5 mM $MgCl_2$, 1 mM DTT, 0.05% (W/V) CHAPS, 1 M NaCl] and subsequently with 75 ml of Buffer 5. 2'-PDE activity was measured in each of the eluted fractions. Using a dialysis membrane with a molecular weight cut off of 7000, 20 ml of the active fraction was dialyzed against 1 L of Buffer 4 for 12 hours.

The resulting dialysis inner solution was loaded onto an anion exchange column (Resource Q 1 ml: manufactured by Amersham Bioscience) which had been equilibrated in advance with Buffer 4. After the column was washed with 10 ml of Buffer 4, a linear gradient was prepared with 100 ml of Buffer 4 and 100 ml of Buffer 5 to elute the components adsorbed to the column. The 2'-PDE activity was measured for each of the eluted fractions. Using a dialysis membrane with a molecular weight cut off of 7000, 2 ml of the active fraction was dialyzed against 1 L of Buffer 4 for 12 hours.

The resulting dialysis inner solution was loaded onto an anion exchange column (Mono Q PC 1.6/5: manufactured by Amersham Bioscience) which had been equilibrated in advance with Buffer 4. After the column was washed with 4 ml of Buffer 4, a linear gradient was prepared with 16 ml of Buffer 4 and 16 ml of Buffer 5 to elute the components adsorbed to the column. 2'-PDE activity was measured in each of the eluted fractions. The active fraction and neighbouring fractions were separated by SDS-polyacrylamide gel electrophoresis (a 12.5% gel was used) under reducing conditions and subjected to fluorescent staining (Sypro Ruby: manufactured by Molecular Probes, Inc.). As a result, a band correlating with the 2'-PDE activity was detected at the position corresponding to about 65 kDa (FIG. 1).

A 50 µl aliquot from the 2'-PDE activity peak fraction was fractionated using a gel filtration column (Superdex 75 PC 3.2/30: manufactured by Amersham Bioscience) which had been equilibrated in advance with Buffer 6 [composition: 20 mM HEPES (pH 7.0), 5 mM $MgCl_2$, 1 mM DTT, 0.05% (W/V) CHAPS, 150 mM NaCl]. 2'-PDE activity was measured in each of the eluted fractions. The active fraction and the neighbouring fractions were separated by SDS-polyacrylamide gel electrophoresis (a 12.5% gel was used) under reducing conditions and subjected to fluorescent staining. As a result, a band correlating with the 2'-PDE activity was detected at the position corresponding to about 65 kDa (FIG. 2).

Example 2

Detection of the 2'-PDE Activity

To 10 p[1] of a specimen, 40 µl of Buffer 7 [composition: 20 mM HEPES (pH 7.0), 5 mM $MgCl_2$, 1 mM DTT, 1 mg/ml bovine serum albumin] containing 1.5 mM adenylyl(2'-5') adenosine (manufactured by Seikagaku Corporation) was added and then the mixture was incubated at 37° C. for 60 min. Ten µl of Buffer 8 [composition: 0.5 M succinic acid (pH 6.0), 2.5 M NaCl] containing 3.5 µg/ml adenosine deaminase (derived from bovine spleen; manufactured by Sigma) was added and the mixture was incubated at 37° C. for further 20 min. Then, 60 µl of the deproteinization solution included in an ammonia test kit (manufactured by Wako Pure Chemical Industries, Ltd.) was added and mixed, and the mixture was centrifuged at 700×g at room temperature for 15 min. Fifty µl of supernatant was recovered, and 50 µl of solution A, 25 µl of solution B and 50 µl of solution C, all included in the kit, were sequentially added and mixed. Afterwards, the mixture was incubated at 37° C. for 20 min., the absorbance at wavelength ($\lambda$) 630 nm was measured. The measurement for the reaction performed using Buffer 7 without adenylyl(2'-5')adenosine was subtracted from the measurements obtained. 2'-PDE activity that produces 1 mM of adenosine under the detection conditions described in this Example was defined as one unit (unit; hereinafter referred to as "U")/ml.

Example 3

Cloning of cDNA Coding for Human 2'-PDE

1) Determination of the Partial Sequence of Human 2'-PDE

The band detected in Example 1 correlating to 2'-PDE activity and being about 65 kDa on an SDS-polyacrylamide gel generated by electrophoresis under non-reducing conditions (FIG. 1 or FIG. 2) was excised from the gel, and to the gel slice obtained was added 100 µl of Buffer 9 [composition: 50% (V/V) acetonitryl, 50% (V/V) 20 mM ammonium bicarbonate (pH 8.0)] to destain the gel at 30° C. for 30 min. with shaking. The destaining step was performed twice. 200 µl of acetonitrile was added to the destained gel slice and the slice was dehydrated at 20° C. for 1 min. with shaking. To the dried gel slice which was recovered, 50 µl of Buffer 10 [composition: 20 mM ammonium bicarbonate (pH 8.0)] containing 10 mM DTT was added and the protein(s) in the gel were reduced by shaking at 50° C. for 30 min. Then, to the gel slice was added 100 µl of Buffer 10 containing 55 mM iodoacetamide and the protein in the gel was alkylated at 20° C. for 20 min. in the dark with shaking. Then, to the gel slice, 200 µl of acetonitrile was added and the gel was dehydrated at 20° C. for 1 min. with shaking. To the dried gel slice recovered, 200 µl of Buffer 10 was added and the gel slice was washed at 20° C. for 15 min. with shaking. To the resulting gel slice, 200 µl of acetonitrile was added, and the gel was dehydrated at 20° C. for 1 min. with shaking and then completely dried using a centrifugal evaporator (manufactured by Tokyo Rika Kikai Co., Ltd.). To the dried gel slice, 10 µl of 10 ng/µl trypsin (manufactured by Promega Corporation; Modified trypsin sequencing grade) was added to digest the protein(s) in the gel at 37° C. for 12 hours. The digested peptides thus produced were extracted once with 20 µl of Buffer 11 [composition: 0.05% (V/V) formic acid, 99.95% distilled water] and twice with 20 µl of Buffer 12 [composition: 0.05% (V/V) formic acid, 99.95% acetonitrile] by shaking at 20° C. for 5 min. The recovered extract was concentrated to 20 µl using a centrifugal evaporator.

The extract was subjected to liquid chromatography/tandem mass spectrometry.

Operation of the liquid chromatography system (manufactured by Waters Corporation; CapLC), was at a flow rate of 250 nl/min with a splitter. A reverse phase resin (Inertsil 2 µm: manufactured by GL Sciences Inc.) filled into an electrospray needle (Picotip: manufactured by New Objective, Inc.; inner diameter 75 µm, tip diameter 5 µm, length 5 cm) was used as the column. As the mass spectrometer, Q-TOF2 manufactured by Micromass Ltd. was used.

Of the extract described above, 5 µl was run on the above column which had been equilibrated in advance with Buffer 11.

Figure 3A:
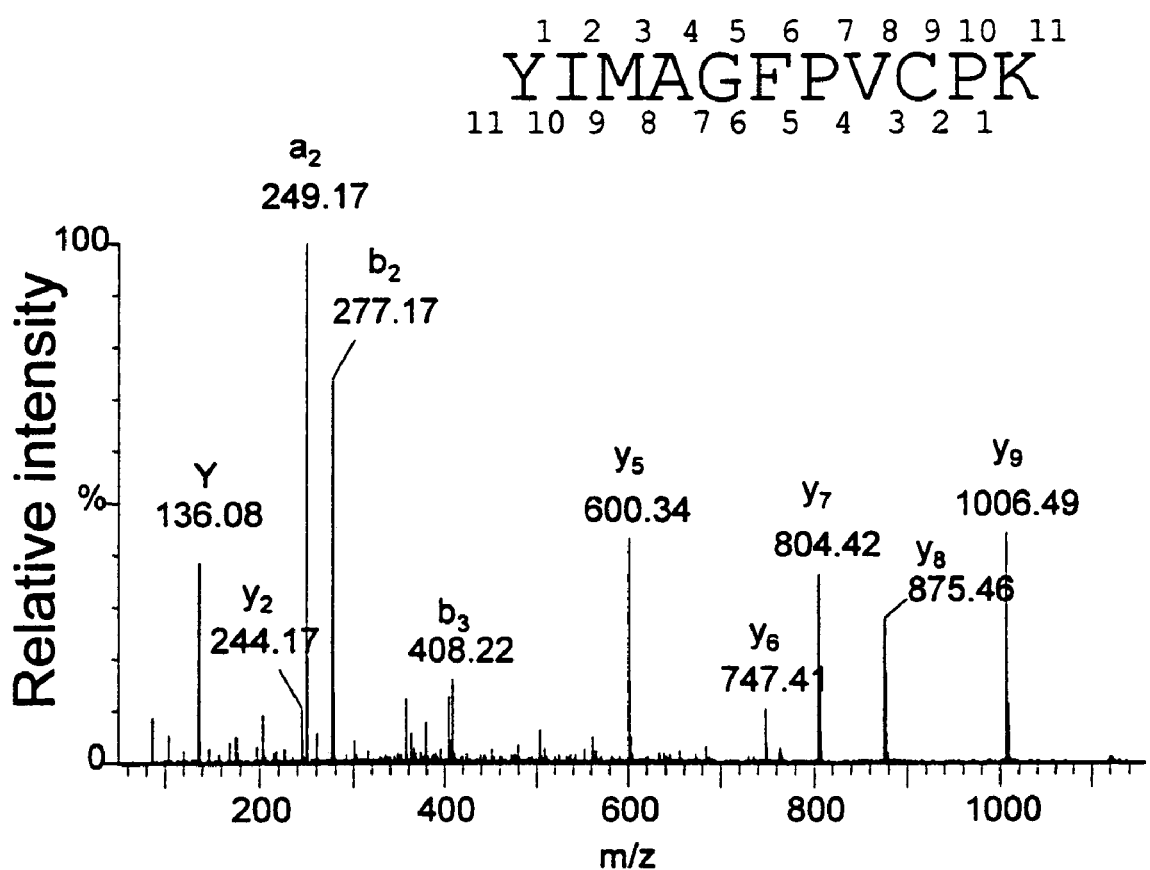
FIG. 3a: a tandem mass spectrometry spectrum using monoisotopic mass 641.82 as precursor ion, wherein said monoisotopic mass 641.82 was eluted, in the liquid chromatography/tandem mass spectrometry as described in Example 3, among the peptides obtained by digesting the band of about 65 kDa excised from the SDS-polyacrylamide gel.
Figure 3B:
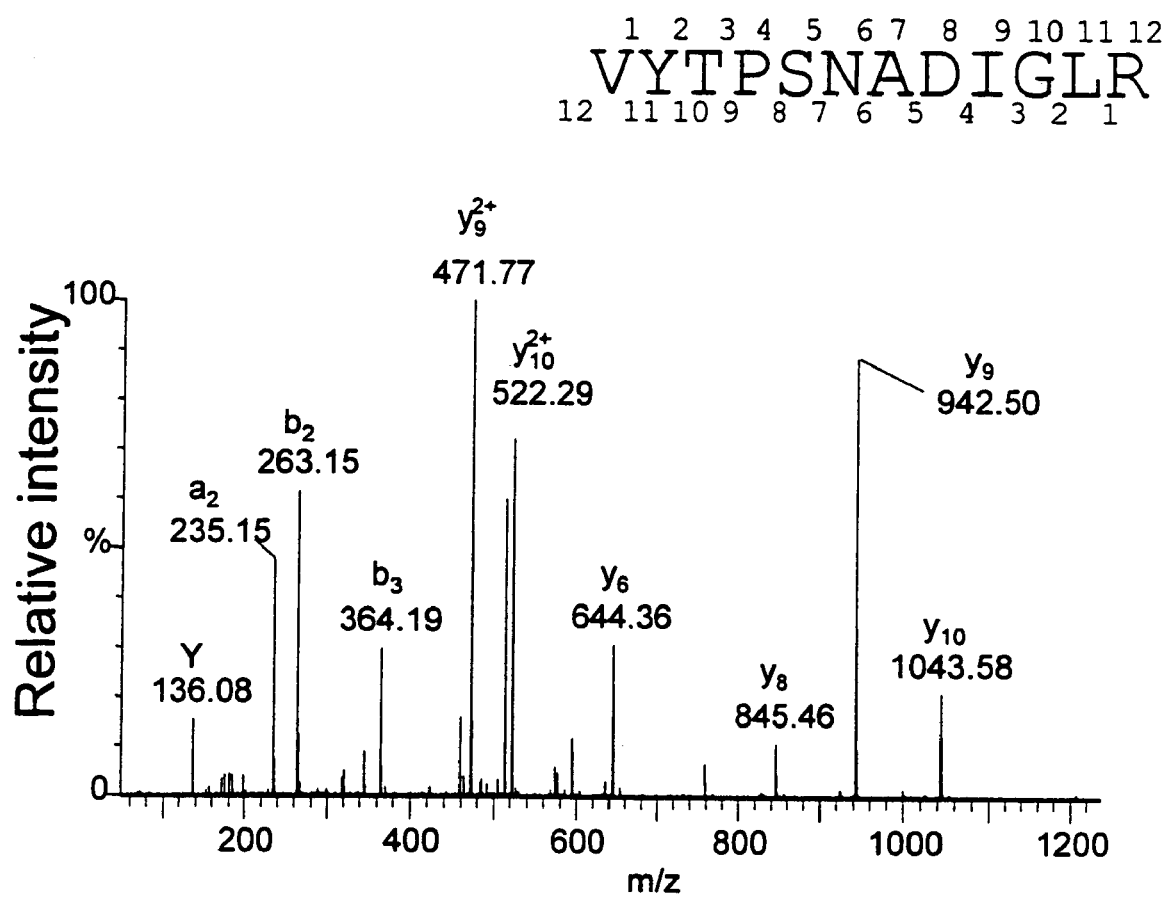
FIG. 3b: a tandem mass spectrometry spectrum using monoisotopic mass 653.34 as precursor ion, wherein said monoisotopic mass 653.34 was eluted, in the liquid chromatography/tandem mass spectrometry as described in Example 3, among the peptides obtained by digesting the band of about 65 kDa excised from the SDS-polyacrylamide gel.
Figure 3C:
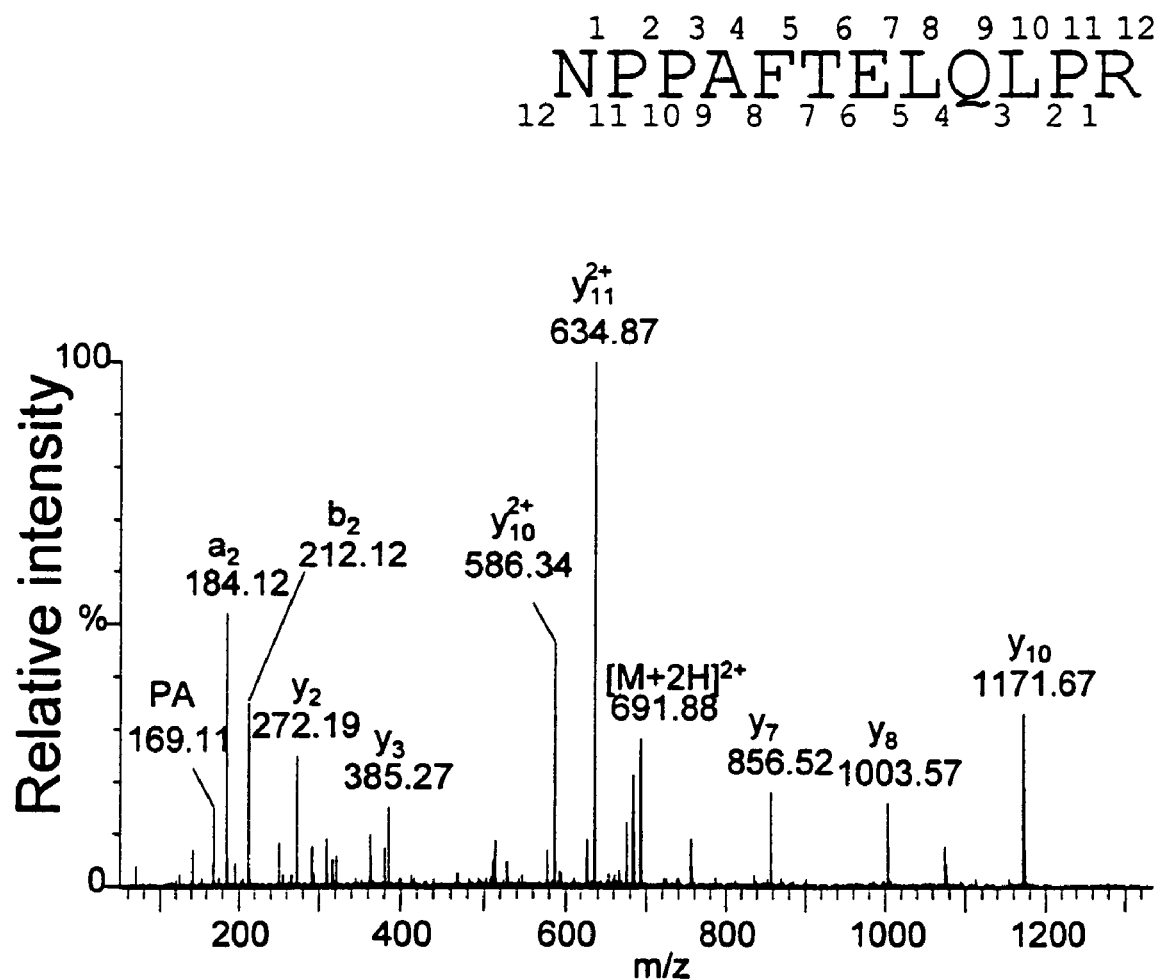
FIG. 3c: a tandem mass spectrometry spectrum using monoisotopic mass 691.88 as precursor ion, wherein said monoisotopic mass 691.88 was eluted, in the liquid chromatography/tandem mass spectrometry as described in Example 3, among the peptides obtained by digesting the band of about 65 kDa excised from the SDS-polyacrylamide gel.

Afterwards, the column was washed with 3 µl of Buffer 11, a concentration gradient was prepared at a flow rate of 250 nl/min in 15 min. so that Buffer 11=100% would linearly change from Buffer 11: Buffer 12=30%:70% (V/V), and the components adsorbed to the column were eluted and directly introduced into a tandem mass spectrometer. The obtained mass spectrum data were analyzed using database search software ((Mascot: manufactured by Matrix Science). The database, the nr (Genbank) database edited by NCBI in the United States. The band of about 65 kD on FIG. 1 correlating to the 2'-PDE activity and the band of about 65 kD on FIG. 2 correlating to the 2'-PDE activity, were found using a monoisotopic mass of m/z 641.82, 653.34 and 691.88 MS/MS spectrum (see FIG. 3) as a precursor ion to be the same known human amino acid sequence (Genbank Accession No. BAB85079.1). The respective MS/MS spectra were attributed to the predicted trypsin-digested fragment(s) of BAB85079.1 (see FIG. 3). The MS/MS spectra with a monoisotopic mass of m/z 641.82, 653.34, and 691.88, as the precursor ion, corresponded respectively to the amino acid sequence as set forth in Sequence ID No.3 of the Sequence Listing (FIG. 3a), the amino acid as set forth in Sequence ID No.4 (FIG. 3b), and the amino acid sequence as set forth in Sequence ID No.5 (FIG. 3c). Based on these results, the human sequence obtained (above described, BAB85079.1) was indicated to be the amino acid sequence of a full-length or partial polypeptide having human 2'-PDE activity.

2) Determination of the Nucleotide Sequence Coding for Human 2'-PDE

Using a nucleotide sequence (Genbank Accession No. AK074423.1) corresponding to the obtained amino acid sequence of human 2'-PDE or a fragment thereof (above described, BAB85079.1), in silico EST walking was conducted as described below.

As a result of a BLAST search (NCBI BLASTN, Version 6.1, filter option: OFF) of the GenBank EST database of NCBI using AK074423.1 as the query, a nucleotide sequence having an overlap of 358 bases and 100% identity (Genbank Accession No. BM894197.1) was obtained.

Similarly, as a result of a BLAST search (NCBI BLASTN, Version 6.1, filter option: OFF) of the EST database as described above using the nucleotide sequence (above described, BM894197.1) as the query, a nucleotide sequence having an overlap of 238 bases and 100% identity (Genbank Accession No. H06019.1) was obtained.

Further, as a result of a BLAST search (NCBI BLASTN, Version 6.1, filter option: OFF) of the above described EST database using the nucleotide sequence (above described, H06019.1) as the query, a nucleotide sequence having an overlap of 229 bases and 99% identity (Genbank Accession No. H42112.1) was obtained.

By assembling the four nucleotide sequences thus obtained (above described, AK074423.1, BM894197.1, H06019.1, and H42112.1) using PHRAP (version 0.960731), the nucleotide sequence of 1939 bp as set forth in Sequence ID No.10 of the Sequence Listing was obtained. The sequence of nucleotide numbers 72 to 1901 of the nucleotide sequence (Sequence ID No.1 of the Sequence Listing) was deduced as being the open reading frame (hereinafter referred to as "ORF") coding for a polypeptide having the amino acid sequence, as set forth in Sequence ID No.2 of the Sequence Listing, consisting of a total of 609 residues starting with methionine and ending with a stop codon. The ORF obtained was longer than any of the nucleotide sequences used for the assembly.

3) cDNA Cloning of Human 2'-PDE by Reverse Transcription and PCR

A cDNA of human 2'-PDE having the nucleotide sequence of Sequence ID No.1 of the Sequence Listing as indicated in the above-described part 2) was cloned from poly(A)+ RNA which was derived from human liver by combining reverse transcription (reverse transcription hereinafter referred to as "RT") and PCR reactions.

Two μg of poly(A)+ RNA derived from human liver (Human liver poly(A)+ RNA: manufactured by BD Biosciences Clontech) and 1 μg of p(dT)15 (manufactured by Roche Diagnostics) as the primer for cDNA first strand synthesis were mixed. Afterwards, distilled water (DNase and RNase free water: manufactured by Sigma) was added to make the final volume to 15 μl, the mixture was incubated at 70° C. for 10 min. After incubation, the mixture was rapidly chilled on ice and kept standing for 5 min. Then, 5 μl of 5× buffer for the first strand synthesis (5× first strand buffer), 2.5 μl of 100 mM DTT (both provided with SUPERSCRIPT II (manufactured by Invitrogen)), 1 μl of 25 mM dNTPs (25 mM each of deoxy ATP deoxy CTP, deoxy GTP, and deoxy TTP) (all manufactured by Invitrogen), 0.5 μl of 40 U/μl ribonuclease inhibitor (RNase inhibitor: manufactured by TOYOBO), and 1 μl of 200 U/μl reverse transcriptase (SUPERSCRIPT II RNase H-Reverse Transcriptase: manufactured by Invitrogen) were added to make the final volume to 25 μl, and after incubating at 42° C. for 90 min. and at 70° C. for 10 min., distilled water (DNase and RNase free water: manufactured by Sigma) was added to make the final volume to 50 μl. The resulting solution was used in the following experiment as the first strand of cDNA.

The oligonucleotide primer 1 (5'-CTCCTCAGCTCCAC-CTGACAGTAGG-3': Sequence ID No.6 of the Sequence Listing) and primer 2 (5'-TACTTCCTTTTCAGACT-TCAATTCC-3': Sequence ID No.7 of the Sequence Listing) for PCR were designed based on the nucleotide sequence of Sequence ID No.1 of the Sequence Listing and synthesized by a β-cianoethylamidite solid phase synthesis method (produced by Sigma-Genosys Ltd.).

The PCR reaction was conducted using a commercially available kit (KOD-plus DNA Polymerase: manufactured by TOYOBO) according to the protocol attached to the kit. Specifically, to 0.5 μl of the previously obtained cDNA first strand solution, the following were added: a final concentration of 0.3 μM each of the above described oligonucleotide primers 1 and 2 for PCR, 10 μl of concentrated buffer (10× PCR buffer for KOD-plus), a final concentration of 0.2 mM of deoxy ATP, a final concentration of 0.2 mM of deoxy CTP, a final concentration of 0.2 mM of deoxy GTP, a final concentration of 0.2 mM of deoxy TTP, a final concentration of 1 mM of magnesium sulfate, and 2 U of DNA polymerase (KOD-plus DNA polymerase) (all provided with the above KOD-plus DNA Polymerase) to make a final volume of 100 μl. Then, the mixture was heated in a PCR incubator (GeneAmp PCR System 9700: manufactured by Applied Biosystems) at 94° C. for 5 min., and then a thermal cycle consisting of 94° C. for 15 seconds, 65° C. for 30 seconds, and then 68° C. for 4 min. was repeated 40 times, followed by an incubation at 72° C. for 10 min., the resulting mixture was stored at 4° C. After the reaction was complete, an aliquot of the reaction mixture was subjected to electrophoresis on a 1.2% agarose gel, the gel was stained with a staining solution (SYBR Gold nucleic acid gel stain: manufactured by Molecular Probes). As a result, it was confirmed that the desired cDNA (1939 bp) was amplified specifically.

The amplified cDNA was purified from the PCR reaction mixture using a commercially available kit (QIAquick PCR Purification Kit: manufactured by QIAGEN) according to the protocol provided with the kit. Then, using a commercially available kit (Zero Blunt TOPO PCR Cloning Kit: manufactured by Invitrogen) according to the protocol provided with the kit, the cDNA was cloned into a commercially available plasmid DNA (pCR-Blunt II-TOPO Vector: provided with the kit). The resulting recombinant plasmid DNA was used to transform competent *E. coli* (TOP10: manufactured by Invitrogen) which were then cultured on LB agar plates containing 50 μg/ml kanamicin. Then, kanamicin-resistant transformant *E. coli* colonies were used to inoculate 1.2 ml of liquid LB medium containing 50 μg/ml kanamicin and incubated at 37° C. over night. Next, recombinant plasmid DNA was recovered from the culture medium using commercially available apparatus (Bio Robot 9600: manufactured by QIAGEN) and a commercially available kit (QIAprep 96 turbo Miniprep Kit: manufactured by QIAGEN) according to the protocol provided with the kit.

The nucleotide sequence of the DNA inserted into the recombinant plasmid DNA was determined by the dideoxy method using a commercially available kit (BigDye Terminator Cycle Sequencing Ready Reaction Kit v2.0: manufactured by Applied Biosystems) according to the protocol provided with the kit.

Sequencing reactions were conducted using commercially available apparatus (GeneAmp PCR System 9700: manufactured by Applied Biosystems). The sequencing reaction product was subjected to nucleotide sequence analysis using a commercially available DNA analyzer (ABI PRISM 3700 DNA Analyzer: manufactured by Applied Biosystems) and it was confirmed that DNA having the nucleic acid sequence as set forth in Sequence ID No.1 of the Sequence Listing had been inserted into the recombinant plasmid DNA obtained.

The nucleotide sequence of Sequence ID No.1 of the Sequence Listing and the deduced amino acid sequence of the polypeptide coded by the nucleotide (Sequence ID No.2 of the Sequence Listing), as a nucleotide sequence of one continuous open reading flame and the amino acid sequence of the polypeptide coded by it, had less than 50% identity to known polynucleotide sequences and known polypeptide sequences.

The molecular weight was calculated using commercially available software (GENETYX-SV/RC Version 5.1.1: manufactured by GENETIX Corporation) based on the amino acid sequence of the polypeptide consisting of the amino acid sequence of Sequence ID No. 2 of the Sequence Listing and was found to be 67338.8985, with the isoelectric point being 6.04.

The transformed *E. coli* carrying the recombinant plasmid DNA pCR-Blunt II TOPO-F6-2/22 into which the above-described cDNA had been inserted was internationally deposited as *E. coli* pCR-Blunt II TOPO-F6-2/22 SANK 71002 on Aug. 6, 2002 at the National Institute of Advanced Industrial Science and Technology, International Patent Organism Depositary, at AIST Tsukuba Central 6, 1-1-1 Higashi, Tsukuba, Ibaraki, Japan and the accession number conferred was FERM BP-8142.

Further, by digesting pCR-Blunt II TOPO-F6-2/22 with the restriction enzyme EcoR I, the polynucleotide coding for human 2'-PDE can be isolated.

Example 4

Expression of Recombinant Human 2'-PDE

1) Construction of Recombinant Expression Plasmid DNA

Using a mammalian cell expression system, a recombinant expression plasmid DNA was constructed for expression of the polypeptide coded by the cDNA obtained in Example 3.

Figure 4:
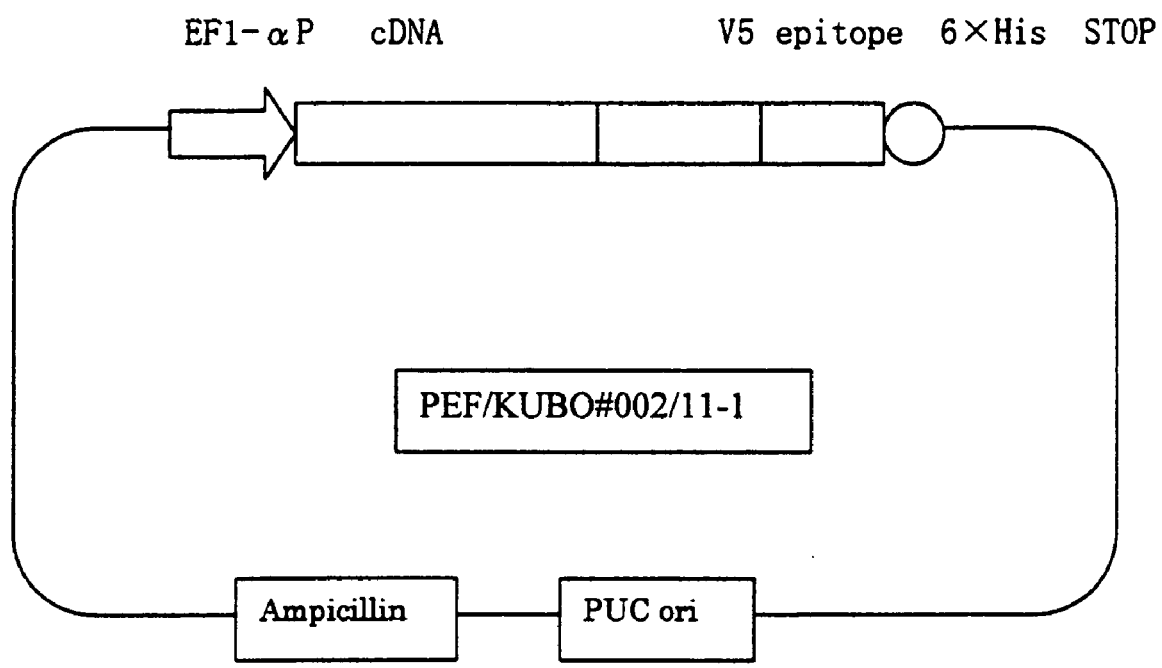
FIG. 4: a schematic drawing of a recombinant plasmid DNA that can be used for functional expression of human 2'-PDE.

Specifically, a recombinant expression plasmid DNA was designed so that, downstream of the EF1-α promoter, a linker was attached to the 3'-end of the cDNA sequence (the nucleotide sequence as described in Sequence ID No.1 of the Sequence Listing) coding for the amino acid sequence as described in Sequence ID No.2 of the Sequence Listing, and further the nucleotide sequence coding for the V5 epitope and a histidine hexamer useful for subjecting a desired polypeptide to affinity chromatography and/or Western blotting was attached to the 3'-end of the linker (FIG. 4).

The oligonucleotide primers 3 (5'-tattatgtggaggctcccaggc-3': Sequence ID No.8 of the Sequence Listing) and 4 (5'-tttccatttaaatcacatacaagtgc-3': Sequence ID No.9 of the Sequence Listing) for preparing recombinant expression plasmid DNA were synthesized using a β-cyanoethylamidite solid phase synthesis (manufactured by Sigma-Genosys Ltd.).

A PCR reaction was performed using a commercially available kit (LA taqDNA Polymerase: manufactured by Takara Syuzo Co., Ltd.) with the GeneAmp PCR system 9700 (manufactured by Perkin Elmer Japan Applied Biosystems) and using the recombinant plasmid DNA pCR-Blunt II TOPO-F6-2/22 obtained in Example 3 as the template. Specifically, 50 µl of reaction solution was prepared containing 140 ng of pCR-BluntII TOPO-F6-2/22, 0.2 µM KUBOF1 (SEQ ID No. 8), 0.2 µM KUBOR1 (SEQ ID No. 9), 2.5 mM deoxy ATP, 2.5 mM deoxy CTP, 2.5 mM deoxy GTP, 2.5 mM deoxy TTP, and 2×GC buffer, as well as 1 U of LA Taq DNA polymerase. Next the reaction solution was heated at 94° C. for 1 min., a thermal cycle consisting of 94° C. for 30 seconds, 60° C. for 30 seconds, and 72° C. for 2 min. was repeated 30 times, and then the solution was incubated at 72° C. for 10 min. The resulting reaction solution was subjected to electrophoresis on a 0.75% agarose gel. As a result, it was confirmed that the desired cDNA (1831 bp) was specifically amplified.

Using a commercially available kit (pEF6/V5-His TOPO TA Expression Kit: manufactured by Invitrogen), the PCR product was cloned into the plasmid DNA pEF6/V5-His-TOPO vector.

Specifically, 0.5 µL of the PCR reaction solution, 1.0 µL of SaltSol (provided with the kit), and 1.0 µL of TOPO vector (provided with the kit) were dispensed into one Treff tube, to which pure water was added to give a final volume of 5 µL, this was followed by incubation at room temperature for 15 min. Then, this was introduced into the *E. coli* strain TOP10 (provided with the kit) by chemical transformation. From colonies of transformed *E. coli* thus obtained, clones containing insert DNA within the plasmid DNA were selected by colony PCR. Then, colonies corresponding to the 10 clones thus selected in replica plates were inoculated into 1.5 mL of 2×TY medium and cultured with shaking at 37° C., 120 rpm, overnight. After culturing, using a commercially available kit (WizardPlus Minipreps DNA Purification System: manufactured by Promega), plasmid DNA was extracted from each of the 10 clones. By determining the nucleotide sequence for the insert in each plasmid DNA, a clone carrying plasmid DNA with the desired DNA insert was selected, and the recombinant expression plasmid DNA carried by this clone was designated to be pEF6/KUBO#002/11-1.

2) Expression of Human 2'-PDE in COS-1 Cells

Using a commercially available reagent (FuGENE6: manufactured by Roche Diagnostics, i.e., formerly Boehringer Mannheim), the recombinant expression plasmid DNA obtained in part 1), pEF6/KUBO#002/11-1, was introduced by the liposome method into COS-1 cells (American Type Culture Collection No. CRL-1650), a cell line derived from monkey kidney.

The COS-1 cells were cultured beforehand until they were semi-confluent under 5% $CO_2$, at 37° C., in a cell culture flask (culture area 225 $cm^2$: manufactured by Sumitomo Bakelite Co., Ltd.) containing Dulbecco's Modified Eagle Media (hereinafter referred to as D-MEM: manufactured by GIBCO) supplemented with 10% fetal calf serum (hereinafter referred to as FCS: manufactured by Moregate). Afterwards, the medium was removed from the culture, 3 ml of trypsin-EDTA solution (manufactured by Sigma) was added and incubated at 37° C. for 3 min. to liberate the COS-1 cells from the flask. The liberated cells were recovered by centrifugation at 800 rpm for 4 min., and suspended in phosphate-buffered saline [composition: 0.02% potassium chloride, 0.02% potassium dihydrogenphosphate, 0.8% sodium chloride, 1.15% disodium hydrogenphosphate: hereinafter referred to as PBS(−): manufactured by Nissui Pharmaceutical Co., Ltd.]. The cell number in the resulting suspension was counted, and the cells were dispensed into cell culture dishes of 9 cm diameter (culture area 57 $cm^2$: Sumitomo Bakelite Co., Ltd.) while being diluted to $1\times10^6$ cells/dish with D-MEM supplemented with 10% FCS, and cultured at 37° C. under 5% $CO_2$ for 24 hours.

Transformation was performed by mixing 20 µg of pEF6/KUBO#002/11-1 prepared using a commercially available kit (WizardPlus Maxipreps DNA Purification System: manufactured by Promega) and 30 µl of FuGENE6 (described above, manufactured by Roche Diagnostics), and then adding this to the COS-1 cells. As a negative control, transformation of COS-1 cells with pEF6/V5-His-TOPO/LacZ was performed under the above-described conditions.

The transformed COS-1 cells were cultured at 37° C. for 72 hours under 5% $CO_2$, the medium was removed from the dish and the cells were washed twice with 5 ml of PBS(−).

Subsequently, 1 ml of a cell-solubilizing reagent for mammalian cells (CelLytic-M™: manufactured by Sigma) containing a protease inhibitor cocktail (Complete™: manufactured by Roche Diagnostics) and 1 mM DTT was added and the cells were lysed by incubation at 25° C. for 5 ml. This lysate was collected in another tube, and the dish was washed once with 1 ml of PBS(−) and combined with the lysate. The lysate was centrifuged at 800 rpm for 4 ml. and the supernatant was designated as being the cell lysate.

3) Enzyme Activity of Recombinant Human 2'-PDE

The 2'-PDE activity of the cell lysate containing the recombinant protein obtained in part 2) was detected according to the method described in Example 2. As a result, 2'-PDE activity was detected in the COS-1 cell lysate transformed with pEF6/KUBO#002/11-1. No 2'-PDE was detected in the COS-1 cell lysate transformed with pEF6/V5-His-TOPO/LacZ as the negative control, nor in the non-transformant COS-1 cell lysate (FIG. 5, upper panel).

4) Substrate Specificity of Recombinant Human 2'-PDE (Part 1)

The hydrolytic activity of the cell lysate containing the recombinant protein obtained in part 2) was detected according to the method described in Example 2, except that adenylyl(2'-5')adenosine (manufactured by Seikagaku Corporation) was replaced with adenylyl(3'-5')adenosine (manufactured by Seikagaku Corporation) in the enzyme activity detection method for human 2'-PDE described in part 3). As a result, in the COS-1 cell lysate transformed with pEF6/KUBO#002/1'-1 an activity capable of hydrolyzing adenylyl(3'-5')adenosine was detected which was equivalent to the 2'-PDE activity detected in part 3). In the negative control, i.e., the COS-1 cell lysate transformed with pEF6/V5-His-TOPO/LacZ and in the non-transformed COS-1 cell lysate, an activity capable of hydrolyzing adenylyl(3'-5')adenosine was detected, although it was weak (FIG. 5, lower panel). This activity was considered to be due to a nuclease (nuclease) endogenously present in COS-1 cells.

As described above, the activity capable of hydrolyzing adenylyl(2'-5')adenosine was dependent on the DNA inserted in pEF6/KUBO#002/11-1 and was similar to or greater than the activity capable of hydrolyzing adenylyl(3'-5')adenosine dependent on that DNA, and thus it was confirmed that the polypeptide isolated and functionally characterized in the Examples of the present invention was a 2'-PDE selective for 2',5'-oligoadenylate.

Example 5

Expression Profile of Human 2'-PDE

The EST probe used (Affymetrix GeneChip HG-U133 probe 231839_at: manufactured by Affymetrix) had a nucleotide sequence partially overlapping with Sequence ID No.1 of the Sequence Listing, an expression profile analysis was conducted using the database constructed by GeneLogic (GeneExpressR Software System ver. 1.4.1.0).

Figure 6:
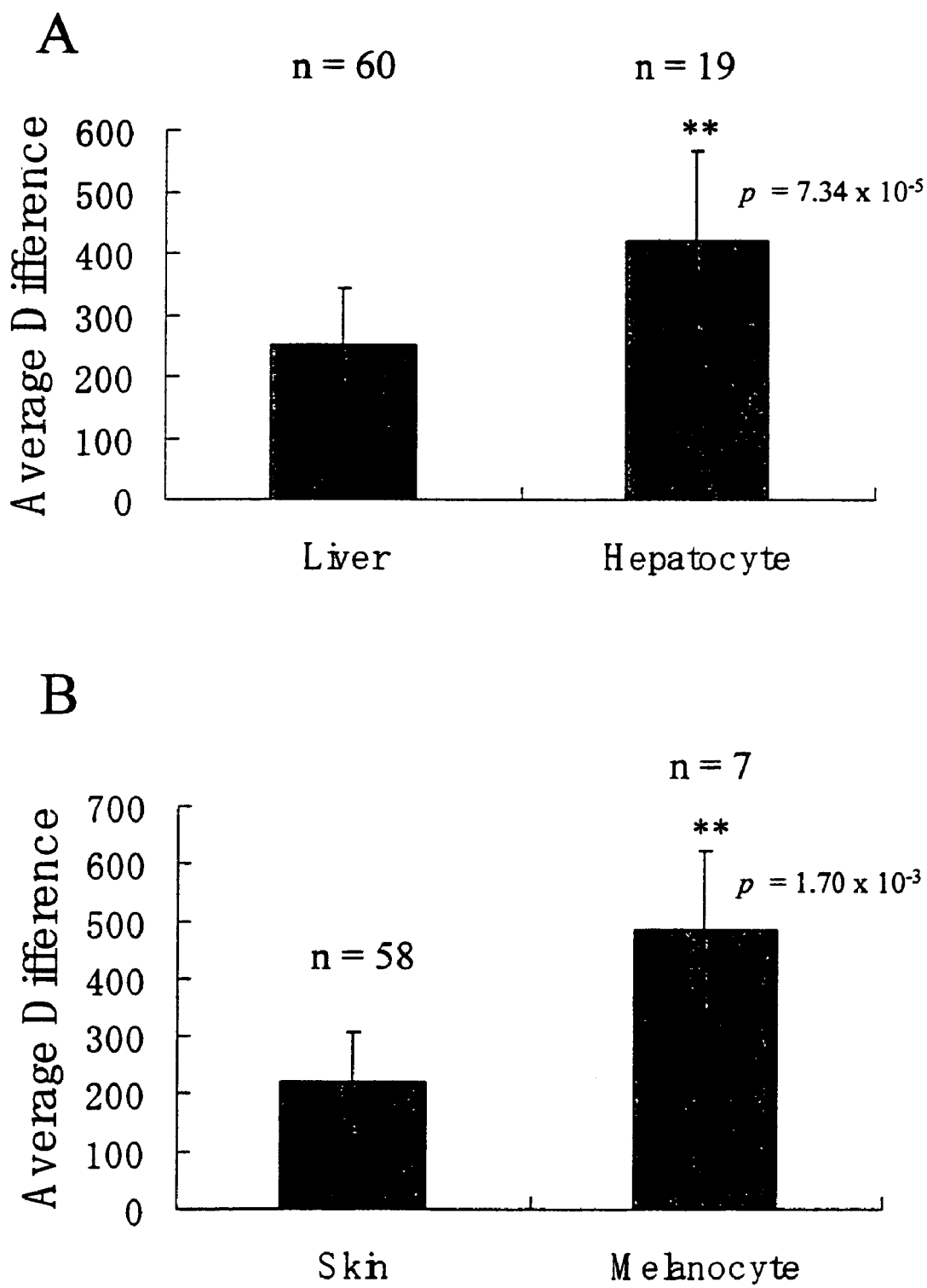
FIG. 6 (upper panel: A): a graph representing the relative amount of transcription of human 2'-PDE. It was transcribed at a high level in hepatocytes.

When the amounts of transcription were compared for 60 liver samples and 19 hepatocyte samples in the database, the levels of transcription in the hepatocyte samples were significantly higher (P value=$7.34^{-5}$: FIG. 6, upper panel). Similarly, when the amounts of transcription were compared for 58 skin samples and 7 melanocyte samples, those in the melanocyte samples were significantly higher (P value=$1.70^{-3}$: FIG. 6, lower panel).

Example 6

Substrate Specificity of Recombinant Human 2'-PDE (Part 2)

1) Preparation of a Partially Purified Specimen

For recombinant human 2'-PDE, the recombinant expression plasmid DNA pEF/KUBO#2/11-1 obtained in part 1) of Example 4 and COS-1 cells were used, cell lysate was obtained by 25-fold scaling up of the method described in part 2) of Example 4.

As a histidine hexamer was attached to the carboxyl end of human 2'-PDE in the cell lysate, thus was used in partial purification conducted as follows. The following purification was performed at 4° C. Specifically, 50 ml of the cell lysate was dialyzed against 500 ml of Buffer 13 [composition: 20 mM HEPES (pH 7.0), 0.3 M NaCl, 10 mM imidazole (imidazole), 0.05% CHAPS, 1 mM DTT, 5 mM $MgCl_2$] for 3 hours, the outer solution was discarded, the inner solution was dialyzed against 500 ml of Buffer 13 for 15 hours. Then, a nickel column was prepared by adding 0.6 ml of 0.1 M $NiSO_4$ to a metal chelate column (HiTrap Metal Chelating HP 1 ml: manufactured by Amersham Bioscience) and this was equilibrated with Buffer 3. The dialysis inner solution was added to this column and the column was washed with 10 ml of Buffer 13. After that, the fraction adsorbed to the column was eluted by preparing a linear concentration gradient with 10 ml of Buffer 13 and the same volume of Buffer 14 [250 mM imidazole (imidazole), 20 mM HEPES (pH 7.0), 0.3 M NaCl, 0.05% CHAPS, 1 mM DTT, 5 mM $MgCl_2$]. The 2'-PDE activity in the eluate was measured by the method as described in Example 2. To the active fraction the same volume of glycerol was added and the fraction was stored at −20° C. as a partially purified 2'-PDE enzyme solution.

2) Analysis of Substrate Specificity

The partially purified 2'-PDE enzyme solution was 5-fold diluted with Buffer 7, and to 3 μl of the resulting diluted enzyme solution 30 μl of Buffer 7 containing 150 μM substrate was added and the mixture incubated at 37° C. for 60 min.

Substrates were selected from the group consisting of adenylyl(2'-5')adenosine, adenylyl(3'-5')adenosine, adenylyl(2'-5)adenylyl(2'-5')adenosine, adenylyl(3'-5')adenylyl(3'-5')adenosine, 5'-phosphoadenylyl(2'-5')adenylyl(2'-5')adenosine, and, 5'-phosphoadenylyl(3'-5')adenylyl(3'-5')adenosine. After the reaction, the enzyme was inactivated by adding 67 μl of methanol and the reaction solution was dried using a centrifugal evaporator. To the resulting dried product, 100 μl of Buffer 15 [composition: 50 mM triethylamine acetate (triethylamine Acetate), pH 7.0] was added to resolubilize the product. Ten μl of the resulting solution was subjected to a reversed phase column (XTerra, RP18; 3.5 μm: diameter 4.6 mm×length 150 mm: manufactured by Waters Corporation) previously equilibrated with Buffer 15. Column chromatography was performed at a flow rate of 1 ml/min. at 40° C. and monitored at a wavelength of 260 nm. Next, the column was washed with a mixed solvent of Buffer 15: Buffer 16 [50 mM triethylamine acetate (triethylamine acetate), pH 7.0, 25% (V/V) acetonitrile]=99:1, a linear concentration gradient starting from Buffer 15: Buffer 16=99:1 to Buffer 15: Buffer 16=2:3 was prepared over 20 min., and the adsorbed fraction was eluted. Using the standard material of each substrate, a conversion formula for obtaining the substrate amount from the peak area was produced. Based on the formula, the amount of reduction of the substrate was calculated from the substrate peak area when the diluted enzyme solution was added, the outcome was regarded as the amount of enzyme reaction product.

Figure 7:
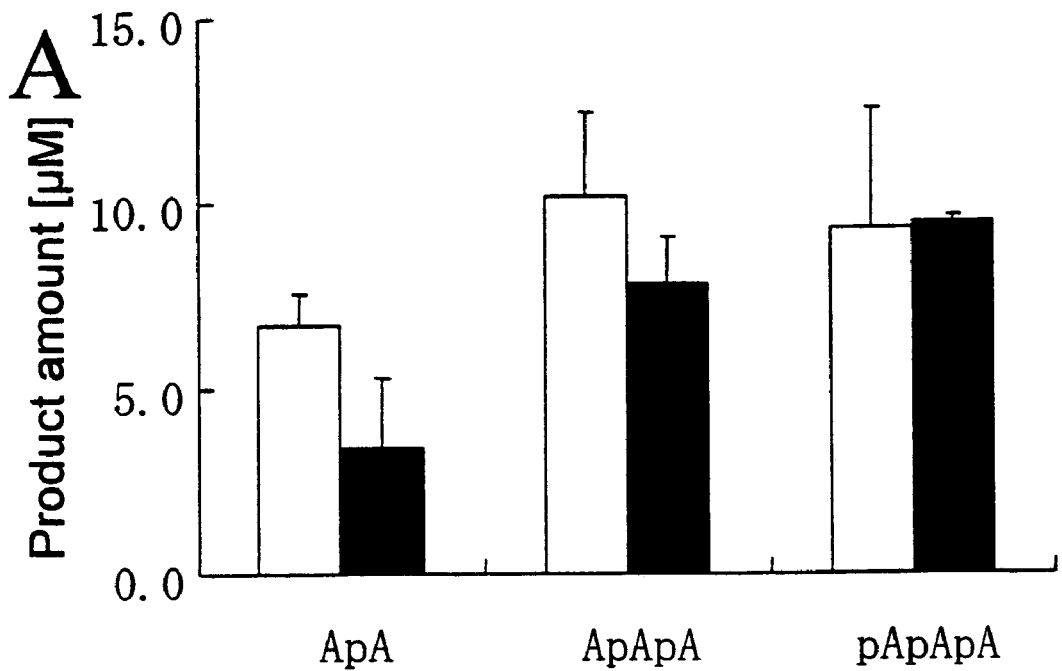
FIG. 7 (upper panel: A): a graph representing the result of comparison of the hydrolytic activity of human 2'-PDE using (2'-5') and (3'-5') oligoadenylates. The open column represents (2'-5') oligoadenylate and the filled column represents (3'-5') oligoadenylate.

The result is shown as a graph in FIG. 7A. Further, the relative cleavage efficiency for each of the substrates, when the amount of enzyme reaction product using adenylyl(2'-5') adenosine as the substrate was defined as one, is shown in FIG. 7B. As a result, the value "1.1" obtained as the cleavage efficiency of the enzyme for adenylyl(3'-5')adenylyl(3'-5') adenosine was remarkably different from the value obtained by Johnston (Johnston., M. I.) et al., i.e., "163." Accordingly, it was confirmed that the human 2'-PDE provided by the present invention was considerably different from the 2'-PDE purified by Johnston et al. in terms of the substrate specificity, although similar in terms of the molecular weight.

Production Example 1

Preparation of the A-74528 Compound

1) Culture of the Bacteria that Produce A-74528

Using the *Streptomyces* sp. (*streptomyces* sp.) strain SANK 61196 (internationally deposited with The National Institute of Bioscience and Human-Technology, Agency of Industrial Science and Technology, METI, of 1-3, Higashi 1-chome, Tsukuba, Ibaraki, Japan on Mar. 30, 2001 and conferred Accession number FERM BP-7532; see the official gazette of Japanese provisional patent publication (KOKAI) 2003-238552), an 8 mm cube from a slant culture, finely crushed, was inoculated into a Erlenmeyer flask of 500 ml volume containing 80 ml of a preculture medium sterilized at 121° C., 30 min., and cultured at 28° C. for 5 days using a rotary shaker incubator under conditions with a rotation radius 7 cm and 210 rpm. The resulting culture medium was inoculated at 3% into four 2 L-volume Erlenmeyer flasks each containing 500 ml of the preculture medium, and cultured at 28° C. for one day under the shaking conditions with a rotation radius of 7 cm and 210 rpm. The resulting culture medium was inoculated at 3% to a 100 L-volume tank incubator containing 60 L of the main culture medium sterilized at 121° C., 20 min., and cultured at 28° C. for 6 days under the conditions with an air flow rate of 1 vvm, a rotation rate of 55 to 100 rpm., and a dissolved oxygen level of 3 to 5 ppm.

The composition of preculture medium was:

| | |
|---|---|
| Glucose | 50 g |
| Soy bean powder | 10 g |
| Elrich broth (Kyokuto) | 4 g |
| Polypepton (Nihon Pharmaceutical Co., Ltd.) | 4 g |
| Yeast extract (Difco) | 1 g |
| CaCO3 | 5 g |
| NaCl | 2.5 g |
| anti-foaming agent* | 0.05 ml |
| tap water | 1000 ml |

*Nissan Disform CB-442(manufactured by NOF Corporation) The pH was adjusted to 7.2 before sterilization.

The composition of main culture medium was:

| | |
|---|---|
| Glucose | 80 g |
| Pharmamedia | 20 g |
| Elrich broth (Kyokuto) | 4 g |
| Polypepton (Nihon Pharmaceutical Co., Ltd.) | 15 g |
| Yeast extract (Difco) | 2 g |
| CaCO3 | 5 g |
| NaCl | 2.5 g |
| anti-foaming agent * | 0.1 ml |
| Tap water | 1000 ml |

* Nissan Disform CB-442(manufactured by NOF Corporation) The pH was not adjusted.

2) Isolation of A-74528 Compound

After 90 L of the culture medium obtained in part 1) was extracted by adding 90 L of acetone, celite (diatomaceous earth celite 545) was added at an amount corresponding to 3% as the filtration auxiliary agent and the mixture was filtered using a filter press. Afterwards, the pH of 190 L of the resulting acetone extract was adjusted to 3, the extract was partitioned with 90 L of ethyl acetate. Next, 130 L of the upper layer (organic layer) obtained as a result of partitioning was sequentially washed with 70 L of saturated NaCl in water and 70 L of water, and it was vacuum-concentrated. Deposited insoluble matter was filtered out using filter paper and a funnel, and ethyl acetate was evaporated by subjecting the recovered filtrate to vacuum concentration, to obtain 86.0 g of oily matter.

The above-described oily matter was dissolved in 500 ml of acetonitrile, loaded to a Cosmosil (Cosmosil) 140 C18 open column (volume 38 L), and, after being washed with 76 L of 20% acetonitrile water, was sequentially eluted with 114 L of 30% acetonitrile water, 114 L of 35% acetonitrile water, and 114 L of 40% acetonitrile water.

The fractions eluted using 35% acetonitrile water and 40% acetonitrile water were combined and subjected to vacuum concentration, the pH was adjusted to 3.5 and the resultant solution was partitioned using 100 L of ethyl acetate. The resulting 130 L of the upper layer (organic layer) was sequentially washed with 70 L of saturated NaCl in water and 70 L of water, and then subjected to vacuum-concentration. Deposited insoluble matter was filtered out using filter paper and a funnel. Ethyl acetate in the resulting filtrate was evaporated by vacuum-concentration to obtain 10.0 g of oily matter. Fifty ml of 100 ml methanol solution in which the oily matter had been dissolved was subjected to an HPLC column (YMC-Pak ODS (diameter 100×500 mm: manufactured by YMC Co., Ltd.) equilibrated beforehand with 35% acetonitrile −0.2% triethylamine-phosphate water (pH 3.5), and eluted using the above solvent used for the equilibration at a flow rate of 200 ml/min. By detecting the absorbance of the eluted fractions at a wavelength (λ) of 350 nm, those fractions that eluted at between 94 and 95 minutes retention time were collected. Similarly, HPLC column chromatography was performed with the remaining 50 ml. By combining and vacuum-concentrating the resulting fractions, 50 ml of suspension was obtained, which was then partitioned with 500 ml of ethyl acetate. The resulting organic layer (upper layer) was dried to obtain 100 mg of oily matter.

3) Measurement of Physicochemical Nature and Determination of Structure of the A-74528 Compound The A-74528 compound had the following physicochemical properties (see the official gazette of Japanese provisional patent publication (KOKAI) 2003-238552):

3-1) nature: pale yellow powder 3-2) solubility: soluble in methanol and dimethyl sulphoxide 3-3) molecular formula: $C_{30}H_{24}O_{11}$ 3-4) molecular weight: 560 (observed value by high resolution capacity FAB-MS method: m/z 561.1405 (M+H)$^+$; calculated value: 561.1397)

3-5) ultraviolet absorption spectrum: $\lambda_{max}$ (in methanol: unit nm) 288 ($\epsilon$ 19000), 354 ($\epsilon$ 15400)

3-6) infrared absorption spectrum: $\nu_{max}$ (KBr method: unit cm$^{-1}$) 3187, 1694, 1674, 1603

3-7) $^1$H-NMR spectrum (in dimethyl sulphoxide-d6: unit ppm: tetramethylsilane of internal control was regarded as 0 ppm): 14.80 (1H, s), 12.71 (1H, s), 11.73 (1H, s), 11.56 (1H, s), 10.90 (1H, s), 10.82 (1H, s), 6.40 (1H, s), 6.22 (1H, s), 6.20 (1H, s), 5.98 (1H, s), 5.18 (1H, s), 4.23 (1H, s), 3.87 (1H, d, J=3.2 Hz), 3.50 (1H, d, J=3.4 Hz), 2.98 (1H, ABq, J=14.7 Hz), 2.94 (1H, m), 2.82 (1H, q, J=7.5 Hz), 2.65 (1H, ABq, J=14.7 Hz), 2.49 (1H, dd, J=19.1, 6.1 Hz), 2.33 (1H, dd, J=19.1, 12.0 Hz), 1.34 (3H, d, J=7.5 Hz).

3-8) $^{13}$C-NMR spectrum: (in dimethyl sulphoxide-d6: unit pm: tetramethylsilane of the internal control was regarded as 0 ppm): 198.5 (s), 189.2 (s), 178.1 (s), 169.9 (s), 164.7 (s), 164.5 (s), 163.9 (s), 163.5 (s), 163.1 (s), 161.7 (s), 141.0 (s), 139.0 (s), 118.8 (s), 113.6 (d), 108.7 (s), 107.2 (s), 106.3 (s), 104.1 (d), 101.8 (d), 100.7 (d), 89.0 (d), 71.8 (d), 53.3 (d), 42.0 (s), 42.0 (t), 34.8 (d), 32.9 (d), 31.4 (d), 29.0 (t), 20.7 (q).

3-9) High performance liquid chromatography (HPLC)

retention time: 6.8 min.

column: PEGASIL-ODS (manufactured by Senshu Scientific Co., Ltd.: diameter 4.6 cm×length 150 mm)

solvent: 35% acetonitrile—0.2 triehylamine—phosphate water (pH 3.5)

flow rate: 1.5 ml/min.

detection: UV 210 nm

Further, the structural formula of the compound was determined to be as follows:

(Formula 1)

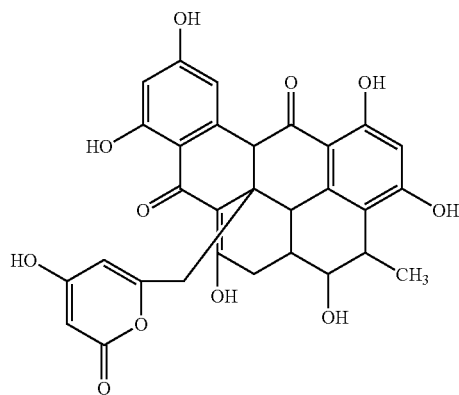

Example 7

Anti-Viral Action of the 2'-PDE Inhibitor

1) Inhibition of Recombinant Human 2'-PDE Activity by A-74528 Compound

To 10 μl of the partially purified human 2'-PDE enzyme solution obtained in part 1) of Production Example 1, were added 80 μl of Buffer 7 containing 0.75 mM adenylyl(2'-5') adenosine as the substrate and 10 μl of a solution of the A-74528 compound dissolved in dimethyl sulphoxide. Then the mixture was incubated at 37° C. for 60 min. and the enzyme was inactivated by addition of 200 μl of methanol. Ten μl of the sample obtained, after insoluble matter was removed using a 0.45 μm filter, was subjected to a reversed phase column (Inertsil ODS-2, 5 μm: diameter 4.6 mm×150 mm: manufactured by GL Science), equilibrated beforehand with Buffer 17 [50 mM ammonium acetate (pH 5.0), 5% (V/V) acetonitrile]. Liquid chromatography was performed at a flow rate of 1 ml/min. at 40° C., and the eluate was monitored at a wavelength of 260 nm. The elution was conducted as an isocratic elution. Using a standard material for the substrate, a conversion formula for obtaining the substrate amount based on the peak area was prepared. Based on the conversion formula, the reduction in the amount of the substrate was calculated from the substrate peak area when the diluted enzyme solution was added, which was regarded as the amount of the enzyme reaction product. As shown in FIG. 8A, the A-74528 compound inhibited recombinant human 2'-PDE in a concentration-dependent manner and the 50% inhibition concentration was 34 μg/ml.

2) Anti-Viral Activity of the A-74528 Compound

1×10$^5$ cells of HeLa cells were cultured to semi-confluence in a 24-well plate (collagen type I coated: manufactured by Asahi Techno Glass Corporation) into which MEM (Minimum Essential Medium) supplemented with 10% FCS (fetal calf serum) had been dispensed, at 37° C. in the presence of 5% CO$_2$. Then the medium was removed, and the cells were cultured further for 24 hours in 250 μl of MEM containing 300 units of interferon-α (manufactured by EMD Bioscience) and 2.5% FCS, or in 250 μl of MEM containing 2.5% FCS without interferon-α. Immediately afterwards, the medium was replaced with a fresh 250 μl aliquot of MEM containing the A-74528 compound and 2.5% FCS, cells were infected with the WR strain of Vaccinia virus (Vaccinia virus WR strain) at a moi of 0.001. At the time point 2 hours after the infection, MEM containing A-74528 compound and 2.5% FCS was added so that the concentration of the A-74528 compound in the medium was equal to that before the viral infection. After a further 22 hours of culture, the medium was removed and then the cells were washed with PBS. Then, the cells were fixed by adding 500 μl of ethanol and incubating at 25° C. for 10 min.

Cells infected with the virus were detected by peroxidase—anti-peroxidase (PAP) staining (Okuno, Y., Tanaka, K., Baba, K., Maeda, A., Kunita, N. and Ueda, S. (1990) J. Clin. Microbiol. 28, 1308-1313) with a slight modification. Specifically, the cells were treated with 500-fold-diluted rabbit anti-vaccinia virus antibody (manufactured by Virostat) at 25° C. for 1 hour, and then washed 3 times with PBS. Subsequently, the cells were treated similarly with each of 1000-fold-diluted goat anti-rabbit immunoglobulin (manufactured by DakoCytomation) and 1000-fold diluted peroxidase-anti-peroxidase conjugate (manufactured by DakoCytomation). Then, using the Liquid DAB Substrate-Chromogen System (manufactured by DakoCytomation) the peroxidase (Peroxidase) was reacted and the visualized plaques were counted.

As shown in FIG. 8B, A-74528 compound alone exhibited a viral replication-suppression activity in a concentration-dependent manner, and in the presence of interferon-α enhanced the viral replication-suppression activity of interferon-α.

Example 8

Anti-Viral Action of 2'-PDE Specific siRNA

Investigation was carried out to determine whether or not a small interfering RNA (small interfering RNA: siRNA) specific for the 2'-PDE of the present invention suppressed the expression of the gene coding for the enzyme and exhibited an anti-viral action. As the siRNA specific to human 2'-PDE and as the control siRNA, those nucleotides set forth in Sequence ID Nos.11 and 12 of the Sequence Listing (5'-GUACAAGGUGGAGCGCAACdTdT-3' and 5'-GUUGCGCUCCACCUUGUACdTdT-3), and those nucleotides set forth in Sequence ID Nos. 13 and 14 of the Sequence Listing (5'-GGUGCUCUCAGAGCUCU-UCdTdG-3' and 5'-GAAGAGCUCUGAGAGCACCdTdG-3') were used, respectively. An anti-vaccinia virus test using HeLa cells was conducted as in Example 7.

$1 \times 10^5$ HeLa cells were cultured in a 24-well plate (collagen type I coated; manufactured by Asahi Techno Glass Corporation) into which MEM supplemented with 10% FCS (fetal calf serum) had been dispensed, in the presence of 5% $CO_2$ at 37° C. for 24 hours. Then the medium was replaced with fresh MEM supplemented with 10% FCS, 100 μl of opti-MEM (a Reduced-Serum Medium; manufactured by Invitrogen) containing 20 pmol siRNA, and 1 μl of Lipofectamine 2000 (Lipofectamine 2000: manufactured by Invitrogen) was added to the medium and the cells were cultured for 24 hours to introduce the siRNA into the cells. Next, the medium was removed, the cells were cultured for further 24 hours with 250 μl of MEM containing 300 units of interferon-α (manufactured by EMD Bioscience) and 2.5% FCS, or with 250 μl of MEM containing 2.5% FCS but without interferon-α. Afterwards, the medium was replaced with 250 μl of fresh MEM supplemented with 2.5% FCS, the cells were infected with vaccinia virus WR strain (Vaccinia virus WR strain) at a moi of 0.001. At the time point when two hours had elapsed since infection, 250 μl of MEM supplemented with 2.5% FCS was added and the cells were cultured for a further 22 hours. After that, the medium was removed and the cells were washed with PBS, and then the cells were fixed by adding 500 μl of ethanol and incubating at 25° C. for 10 min. The cells infected with the virus were detected according to the method as described in part 2) of Example 7.

Figure 9:
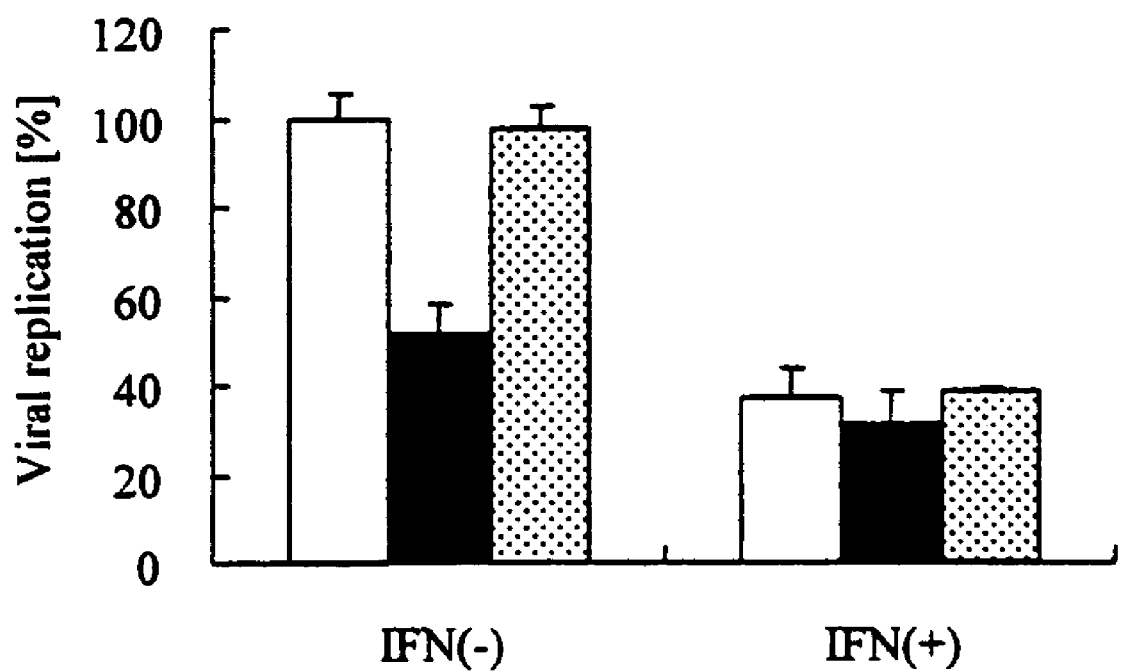
FIG. 9: a graph representing viral replication suppression activity by human 2'-PDE specific siRNA (2'-PDE specific siRNA) and control siRNA (control siRNA) in the presence or absence of interferon (IFN). The open column, filled column, and dotted column were without siRNA, with added 2'-PDE specific siRNA, and with added control siRNA, respectively.

As shown in FIG. 9, siRNA specific to a human 2'-PDE of the present invention showed a tendency to suppress viral replication when used alone and also, when used in the presence of interferon-α, a tendency to enhance the viral replication-suppression action of interferon-α.

Example 9

Attenuation of Anti-Tumor Activity of Interferon by Inactivation of the 2-5A System 1) Establishment of a Human Strain Stably Expressing 2'-PDE Using the Human Prostate Cancer Cell Line PC-3 as the Host PC-3 cells were cultured using RMPI1640 (manufactured by Invitrogen) supplemented with 10% FCS in the presence of 4% $CO_2$ at 37° C. Nucleotides were added to the cDNA of human 2'-PDE appropriately so that the V5 epitope and a histidine hexamer were added to the carboxyl terminus of the human 2'-PDE, and the resultant DNA was inserted into pEF-DEST51 (manufactured by Invitrogen).

Then, the expression plasmid produced was introduced into PC-3 cells using Lipofectamine plus (Lipofectamine plus: manufactured by Invitrogen). The host PC-3 cells are sensitive to blasticidin (blasticidin), whereas those PC-3 cells into which the plasmid has been introduced gain resistance to blasticidin. Thus, stable expression strains were selected by adding 10 μg/ml of blasticidin to the medium. For the isolated stable expression strains, the expression of recombinant human 2'-PDE modified protein (2'-PDE-V5-His) was confirmed by Western blotting analysis using an anti-V5 epitope antibody.

Figure 10:
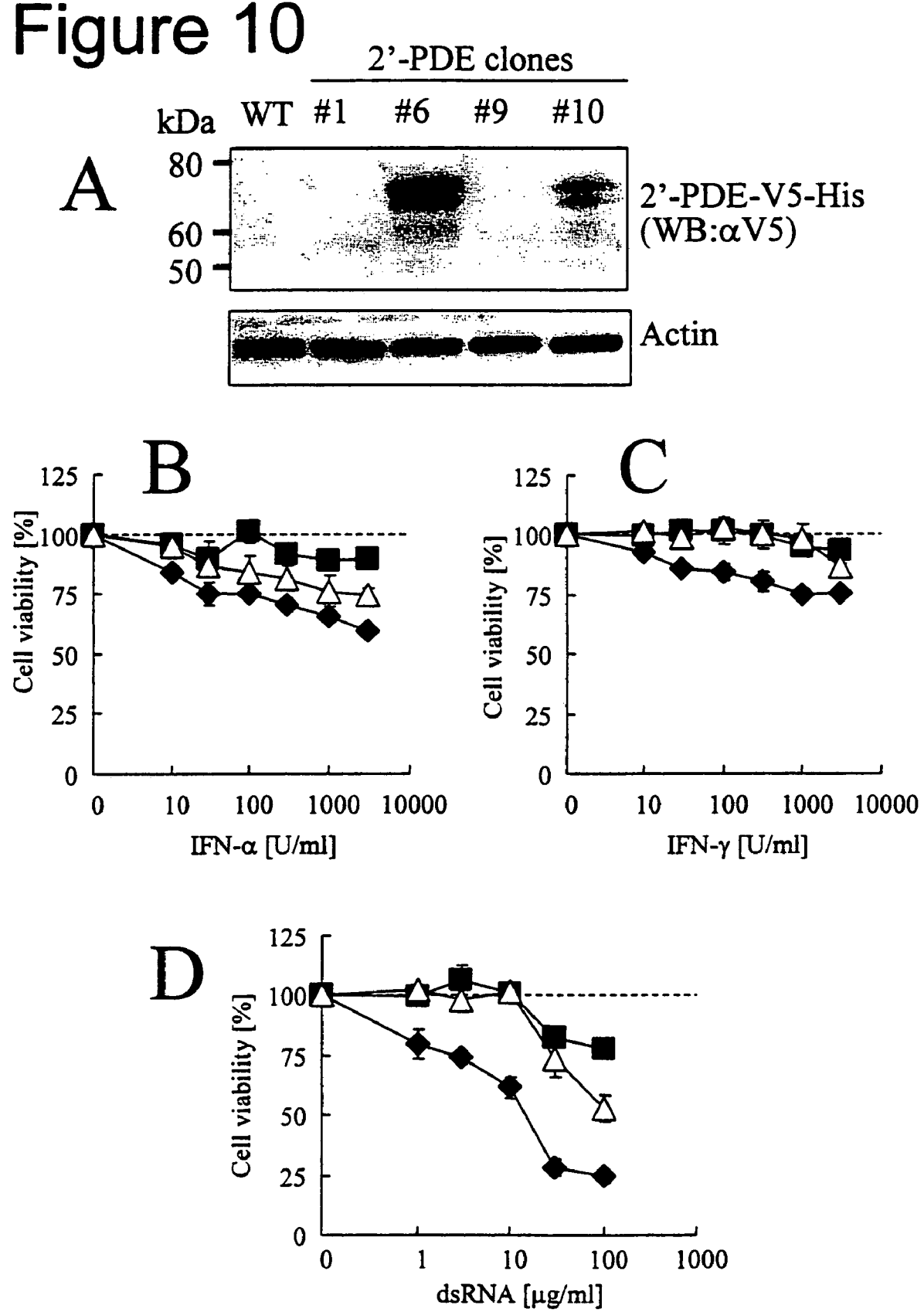
FIG. 10 (upper panel: A): a figure showing stable expression of human 2'-PDE in strains obtained. #6 is a high expression strain, and #10 is a low expression strain.

As shown in FIG. 10A, a high expression strain, #6, and a low expression strain, #10, were obtained as 2'-PDE stable expression strains.

2) Inactivation of the 2-5A System by Over-Expression of 2'-PDE $3.0 \times 10^3$ cells of each of the 2'-PDE stable expression strains #6 and #10, and the host PC-3 cells to which no plasmid had been introduced were suspended individually in 100 μl of RPMI 1640 supplemented with 10% FCS and plated in 96-well plates. The cells were cultured for 3 days in the presence of interferon-α (manufactured by Cosmo Bio Co., Ltd.), interferon-γ (manufactured by R&D systems), or dsRNA (manufactured by Amersham Bioscience) and cell viabilities were measured using Alamar Blue reagent (manufactured by Alamer Bioscience).

As shown in FIGS. 10B and C, interferon-α and interferon-γ suppressed the viability of PC-3 cells in a concentration-dependent manner. Conversely, in the 2'-PDE stable expression strains, the proliferation suppression activity of interferon was attenuated. Further, as shown in FIG. 10D, dsRNA suppressed the viability of PC-3 cells to a greater extent than interferon. In 2'-PDE stable expression strains, the cell proliferation suppression activity of dsRNA was greatly attenuated.

Example 10

Short Chain Form of 2'-PDE (35-609)

1) Preparation of Short Chain Form of 2'-PDE

According to the method as described in Example 4, recombinant expression plasmid into which a nucleotide sequence as described in Sequence ID No.1 of the Sequence Listing had been inserted, was introduced into the human fetal kidney cell line, 293 cells, and strains in which a short chain form of the recombinant human 2'-PDE (35-609) (hereinafter simply referred to as "the short chain form of 2'-PDE (35-609)") was stably expressed were obtained.

A culture of the short chain form of the human 2'-PDE stable expression cells was lysed using a cell-lysing reagent (CelLytic-M: manufactured by Sigma) containing a protease inhibitor cocktail (Complete™: manufactured by Roche Applied Science) and 1 mM DTT according to the protocol provided with the reagent. The resulting cell lysate was used as a crude fraction, from which the short chain form of human 2'-PDE was purified by the method described below. Purification was conducted at 4° C. and the crude fraction was stored at −80° C. until used. The 2'-PDE activity was detected by the method described in Example 2.

After 120 ml of the cell lysate was thawed, it was centrifuged at 7,500×g for 20 min. to remove insoluble matter. Ammonium sulfate was added to the resulting supernatant to 50% saturation and then the mixture was stirred for 3 hours, and then centrifuged at 7,500×g for 20 min. to recover the precipitate.

The precipitate was again solubilized by adding 50 ml of Buffer 2 (see Example 1) containing 1 tablet of a protease inhibitor cocktail (Complete™: manufactured by Roche Applied Science). The resultant solution was transferred to a dialysis membrane with a molecular weight cut off of 7,000 (manufactured by Pierce) and dialyzed against 2 L of Buffer 2 for 3 hours and, after replacing the outer solution with 2 L of fresh Buffer 2, for a further 12 hours.

The resulting inner solution was loaded onto an anion exchange column (Resource Q 6 ml: manufactured by Amersham Bioscience) that had been equilibrated beforehand with Buffer 2. Next, the column was washed with 90 ml of Buffer 2, a linear concentration gradient ranging from Buffer 2 to Buffer 2: Buffer 3=3:1 (V/V) was prepared at a flow rate of 6 ml/min. in 50 min., and the column-absorbed fraction was eluted. Twenty ml of the active fraction was dialyzed using a dialysis membrane with a molecular weight cut off of 7,000 against 500 ml of Buffer 3 for 12 hours.

The resulting inner solution was loaded onto a head-to-tail series of two hydrophobic interaction columns (HiTrap Phenyl FF (low sub) 1 ml: manufactured by Amersham Bioscience) pre-equilibrated with Buffer 3. Then the column was washed with 30 ml of Buffer 3, a linear concentration gradient ranging from Buffer 3 to Buffer 2 (V/V) was prepared at a flow rate of 1 ml/min. in 10 min., and then, by adding 40 ml of Buffer 2 at the same flow rate, the column-absorbed fraction was eluted. Twelve ml of the active fraction was dialyzed using a dialysis membrane with a molecular weight cut off of 7,000 against 500 ml of Buffer 4 for 12 hours.

The resulting inner solution was loaded onto a head-to-tail series of two dye-bound affinity columns (HiTrap Blue HP 1 ml: manufactured by Amersham Bioscience) pre-equilibrated with Buffer 4. Next, the column was washed with 25 ml of Buffer 4, a linear concentration gradient ranging from Buffer 4 to Buffer 4: Buffer 18 [composition: 20 mM HEPES (pH 7.0), 5 mM $MgCl_2$, 1 mM DTT, 0.05% (W/V) CHAPS, 2 M NaCl]=1:1 (V/V) was prepared at a flow rate of 1 ml/min. in 5 min., and another linear concentration gradient ranging from Buffer 4: Buffer 18=1:1 (V/V) to Buffer 18 was prepared at the same flow rate in 5 min. Then, by adding 25 ml of Buffer 18 at the same flow rate, the column-absorbed fraction was eluted. Six ml of the active fraction was dialyzed using a dialysis membrane with a molecular weight cut off of 7,000 against 1 L of Buffer 4 for 12 hours.

Figure 11:
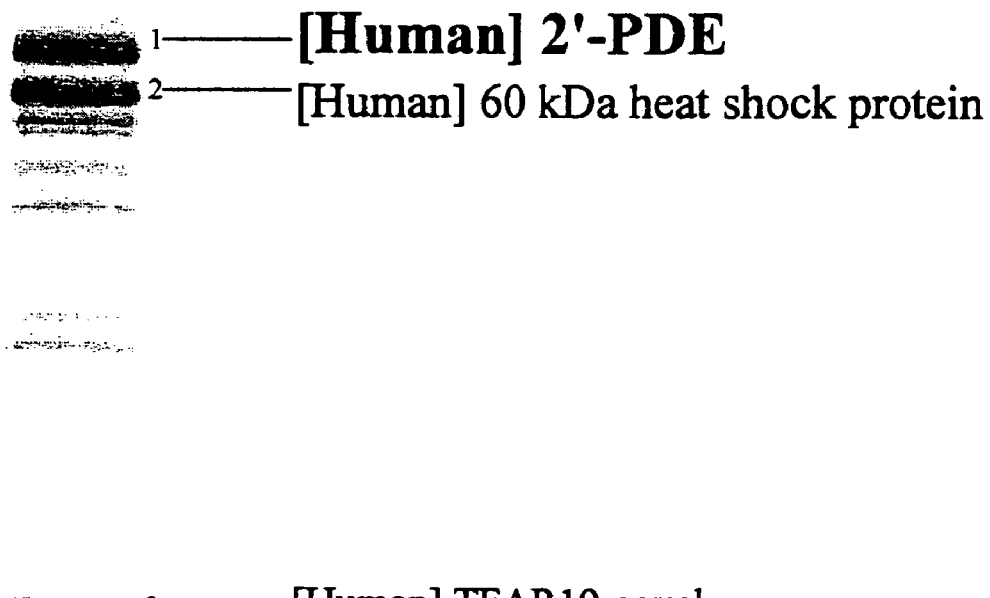
FIG. 11: a figure representing the result of SDS-PAGE of a partially purified short chain form of 2'-PDE (35-609). The band of about 66 kD corresponded to the short chain form of 2'-PDE (35-609).

The resulting inner solution was loaded onto an anion exchange column (Mini Q PC 3.2/3: manufactured by Amersham Bioscience) pre-equilibrated with Buffer 4. Then the column was washed with 2 ml of Buffer 4, a linear concentration gradient from Buffer 4 to Buffer 4: Buffer 5=17:3 (V/V) was prepared at a flow rate of 240 µl/min. in 40 min. to elute the column-absorbed fraction. The fraction that had the highest 2'-PDE activity was separated by SDS-polyacrylamide gel electrophoresis (a 12.5% gel was used) under reducing conditions and stained with a fluorescent dye (Sypro Ruby fluorescence: manufactured by Molecular Probes). Each of the stained bands was digested in the gel using a method as described in part 1) of Example 3 and subjected to liquid chromatography/tandem mass spectrometry. The mass spectrometry procedure was performed according to part 1) of Example 3, except that a RenCon system (manufactured by Nanosolutions) was used as the liquid chromatography system and the flow rate was 100 nl/min. without the splitter, and that the column used was a fused silica of inner diameter of 150 mm modified with a Laser puller (manufactured by Shutter Instrument) filled with reversed phase resin (Develosil ODF-HG-3: manufactured by Nomura Chemical Co., Ltd.). As a result, as shown in FIG. 11, the partial sequence human 2'-PDE was detected in a band corresponding to about 66 kDa.

2) Analysis of the Amino Terminus of the Short Chain Form of 2'-PDE (35-609)

First, an aliquot of the short chain form of 2'-PDE (35-609) protein partially purified in part 1) of Example 10 was separated by SDS-polyacrylamide gel electrophoresis under reducing conditions, blotted onto a polyvinylidene fluoride (polyvinylidene fluoride) membrane, and then subjected to amino-terminal analysis by the Edman degradation method. However, although a sufficient amount of protein was used, no signal was obtained, suggesting that the amino terminus of the short chain form of 2'-PDE (35-609) was blocked.

Then, an aliquot of the partially purified short chain form of 2'-PDE (35-609) protein was separated by SDS-polyacrylamide gel electrophoresis (a 10-20% gradient gel was used) under reducing conditions, and stained with zinc (Zn stain kit: manufactured by BioRad).

After staining, the band corresponding to the short chain form of 2'-PDE (35-609) was digested in the gel according to the method as described in part 1) of Example 3, except that destaining was performed by repeating twice the steps of adding 100 µl of Buffer 19 [composition: 2.5 mM Tris, 19.2 mM glycine (pH 8.3)] to the gel slice and shaking at 25° C. for 5 min. and that as the digestion enzyme, 20 µL of trypsin (5 ng/µl: manufactured by Promega), lysyl endopeptidase (5 ng/µl: manufactured by Wako Pure Chemical), chymotrypsin (5 ng/µl: manufactured by Roche Applied Science) or endoproteinase Glu-C (10 ng/µl: manufactured by Roche Applied Science) was used; trypsin and lysyl endopeptidase, and chymotrypsin and endoproteinase Glu-C were incubated at 37° C. and 25° C., respectively.

The resulting digested peptide extract was subjected to liquid chromatography/tandem mass spectrometry by the method as described in part 1) of Example 10. The 4 sets of mass spectrum data obtained after enzyme digestion were combined and mapped to the amino acid sequence described in Sequence ID No.2 of the Sequence Listing using database search software (Mascot: manufactured by Matrix Science) (FIG. 12A). As a result, a peptide with an acetylated methionine at the 35th position from the amino terminus was found and the MS/MS spectrum of that peptide was well ascribed (FIG. 12B). Based on the above results, it was confirmed that the amino terminus of the short chain form of 2'-PDE (35-609) was the methionine at the 35th position from the amino terminus in the amino acid sequence as described in Sequence ID No.2 of the Sequence Listing.

3) Isoelectric Point of Short Chain Form of 2'-PDE (35-609)

Figure 13:
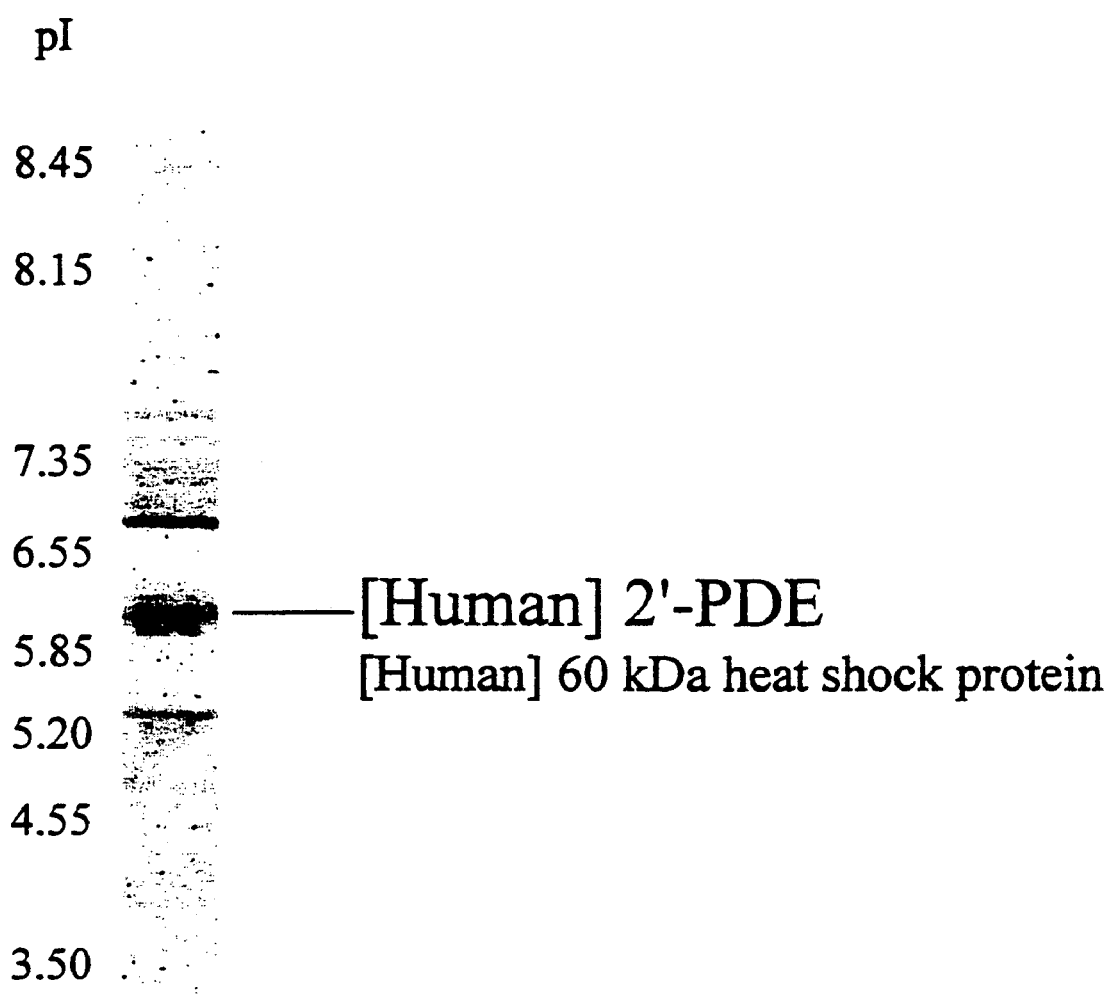
FIG. 13: a figure representing the result of isoelectric point electrophoresis of the short chain form of 2'-PDE (35-609). The band of pI 6.0 corresponded to the short chain 2'-PDE (35-609).

An aliquot of the short chain form of 2'-PDE (35-609) protein partially purified in part 1) of Example 10 was mixed with an equal volume of IEF sample buffer (pH 3-10: manufactured by Invitrogen), and then loaded onto a gel for pH 3-10 isoelectric point electrophoresis (manufactured by Invitrogen) and subjected to electrophoresis under conditions of 100 V for 1 hour, 200 V for 1 hour, and 500 V for 30 min. at room temperature. After electrophoresis, the gel was stained with a fluorescent dye (Sypro Ruby: manufactured by Molecular Probes). As a result, a major band was observed at around isoelectric point pI 6.0. The band was excised and digested in the gel by the method described in part 2) of Example 10, and then subjected to liquid chromatography/tandem mass spectrometry by the method described in part 1) of Example 10. As a result, as shown in FIG. 13, from the band corresponding to around pI 6.0, human 2'-PDE was detected. The theoretical values of the isoelectric point of the full length human 2'-PDE (1-609) and that of the short chain form of 2'-PDE (35-609) calculated from the amino acid sequence were pI 6.0 and pI 5.9, respectively, which as with the experimental value found for the short chain form of 2'-PDE (35-609) (pI 6.0) were very different from that of the enzyme derived from a bovine source purified by Johnston et al. (pI 8.3).

A polypeptide provided by the present invention has 2'-PDE activity and a polypeptide and a polynucleotide coding therefor can be suitably used for screening for a 2'-PDE activity inhibitor substance, a 2'-PDE expression suppression substance, a 2'-PDE binding substance, or a 2-5A system sensitive disease therapeutic or preventive agent and for detection of the 2'-PDE activity or expression, and so on. The substances obtained by screening and by detection methods are useful for the treatment or prevention of 2-5A system sensitive diseases, and for assessment of 2-5A sensitive diseases etc., respectively. Further, an antibody provided by the present invention is useful for immunological detection of a polypeptide of the present invention, or for treatment or prevention of a 2-5A system sensitive disease.

The invention claimed is:

1. An isolated polynucleotide selected from the group consisting of
 [i] a polynucleotide encoding a polypeptide comprising the amino acid sequence as set forth in Sequence ID No.2 of the Sequence Listing;
 [ii] a polynucleotide comprising the nucleotide sequence as set forth in Sequence ID No.1 of the Sequence Listing; and
 [iii] the shorter of the polynucleotides between the two restriction enzyme EcoR1 recognition sites of the recombinant plasmid DNA contained within the transformant E. coli strain pCR-Blunt II TOPO-F6-2/22 SANK 71002 (FERM BP-8142)

2. The isolated polynucleotide as defined in claim 1, wherein the isolated polynucleotide is the polynucleotide comprising the nucleotide sequence as set forth in Sequence ID No. 1 of the Sequence Listing.

3. An isolated polynucleotide selected from the group consisting of
 [i] a polynucleotide encoding a polypeptide consisting of an amino acid sequence in which the methionine at the 1st position, or two or more contiguous amino acids, including the methionine at the 1st position, of the amino acids from the methionine at the 1st position to the alanine at the 34th position in the amino acid sequence as set forth in Sequence ID No.2 of the Sequence Listing have been deleted;
 [ii] a polynucleotide consisting of a nucleotide sequence in which the adenosine at the 1st position and the two 3'-adjacent nucleotides (5'-terminal trimer), or 3n, wherein n is an integer from 1 to 33, contiguous nucleotides including the 5'-terminal trimer, of the nucleotides from the adenosine at the 1st position to the guanosine in 102nd position in the nucleotide sequence as set forth in Sequence ID No.1 of the Sequence Listing have been deleted;
 [iii] a polynucleotide encoding the polypeptide consisting of the methionine at the 35th position to the lysine at the 609th position of the amino acid sequence as set forth in Sequence ID No.2 of the Sequence Listing;
 [iv] a polynucleotide consisting of the adenosine at the 103rd position to the 1827th adenosine in the nucleotide sequence as set forth in Sequence ID No.1 of the Sequence Listing;
 [v] a polynucleotide consisting of the adenosine at the 103rd position to the guanosine at the 1830th position in the nucleotide sequence as set forth in Sequence ID No.1 of the Sequence Listing; and
 [vi] a polynucleotide as defined in any of [i] to [v] comprising a methionine codon that has been added to the 5'-terminus.

4. The isolated polynucleotide as defined in claim 3, wherein the isolated polynucleotide is the polynucleotide consisting of the adenosine at the $103^{rd}$ position to the $1827^{th}$ adenosine in the nucleotide sequence as set forth in Sequence ID No. 1 of the Sequence Listing.

5. An isolated polynucleotide encoding a polypeptide, said polypeptide being selected from the group consisting of
 (i) a polypeptide comprising the amino acid sequence as set forth in Sequence ID No. 2 of the Sequence Listing;
 (ii) a polypeptide encoded by the shorter of the polynucleotides between the two restriction enzyme EcoR1 recognition sites of the recombinant plasmid DNA contained within the transformant E. coli strain pCR-Blunt II TOPO-F6-2/22 SANK 71002 (FERM BP-8142);
 (iii) a polypeptide consisting of an amino acid sequence in which the methionine at the $1^{st}$ position, or the two or more contiguous amino acids including the methionine, of the amino acids from the methionine at the $1^{st}$ position to the alanine at the $34^{th}$ position in the amino acid sequence as set forth in Sequence ID No. 2 in the Sequence Listing have been deleted;
 (iv) a polypeptide consisting of the amino acid sequence from the methionine at the $35^{th}$ position to the lysine at the $609^{th}$ position of the amino acid sequence as set forth in Sequence ID No. 2 of the Sequence Listing; and
 (v) a polypeptide as defined in (iii) or (iv), which comprises a methionine that has been added to the amino terminus.

6. The isolated polynucleotide as defined in claim 5, wherein said polynucleotide encodes the polypeptide comprising the amino acid sequence as set forth in Sequence ID No. 2 of the Sequence Listing.

7. The isolated polynucleotide as defined in claim 5, wherein said polynucleotide encodes the polypeptide consisting of the amino acid sequence from the methionine at the $35^{th}$ position to the lysine at the $609^{th}$ position of the amino acid sequence as set forth in Sequence ID No. 2 of the Sequence Listing.

8. A recombinant plasmid DNA into which a polynucleotide has been inserted, said polynucleotide being selected from the group consisting of
 [i] a polynucleotide encoding a polypeptide comprising the amino acid sequence as set forth in Sequence ID No.2 of the Sequence Listing;
 [ii] a polynucleotide comprising the nucleotide sequence as set forth in Sequence ID No.1 of the Sequence Listing;
 [iii] the shorter of the polynucleotides between the two restriction enzyme EcoR1 recognition sites of the recombinant plasmid DNA contained within the transformant E. coil strain pCR-Blunt II TOPO-F6-2/22 SANK 71002 (FERM BP-8142);
 [iv] a polynucleotide encoding a polypeptide consisting of an amino acid sequence in which the methionine at the 1st position, or two or more contiguous amino acids, including the methionine at the 1st position, of the amino acids from the methionine at the 1st position to the alanine at the 34th position in the amino acid sequence as set forth in Sequence ID No.2 of the Sequence Listing have been deleted;

[v] a polynucleotide consisting of a nucleotide sequence in which the adenosine at the 1st position and the two 3'-adjacent nucleotides (5'-terminal trimer), or 3n, wherein n is an integer from 1 to 33, contiguous nucleotides including the 5'-terminal trimer, of the nucleotides from the adenosine at the 1st position to the guanosine in 102nd position in the nucleotide sequence as set forth in Sequence ID No.1 of the Sequence Listing have been deleted;

[vi] a polynucleotide encoding the polypeptide consisting of the methionine at the 35th position to the lysine at the 609th position of the amino acid sequence as set forth in Sequence ID No.2 of the Sequence Listing;

[vii] a polynucleotide consisting of the adenosine at the 103rd position to the adenosine at the 1827th position in the nucleotide sequence as set forth in Sequence ID No.1 of the Sequence Listing;

[viii] a polynucleotide consisting of the adenosine at the 103rd position to the guanosine at the 1830th position in the nucleotide sequence as set forth in Sequence ID No.1 of the Sequence Listing; and

[ix] a polynucleotide as defined in any of [v] to [ix] comprising a methionine codon that has been added to the 5'-terminus.

9. The recombinant plasmid DNA as defined in claim 8, wherein said polynucleotide is the polynucleotide comprising the nucleotide sequence as set forth in Sequence ID No. 1 of the Sequence Listing.

10. The recombinant plasmid DNA as defined in claim 8, wherein said polynucleotide is the polynucleotide consisting of the adenosine at the $103^{rd}$ position to the $1827^{th}$ adenosine in the nucleotide sequence as set forth in Sequence ID No. 1 of the Sequence Listing.

11. A recombinant plasmid DNA as defined in claim 8, wherein the recombinant plasmid DNA is an expression plasmid DNA.

12. The recombinant plasmid DNA contained within the transformant *E. coli* strain pCR-Blunt II TOPO-F6-2/22 SANK 71002 (FERM BP-8142).

13. An isolated host cell transformed with a plasmid as defined in claim 8.

14. A host cell as defined in claim 13, wherein the host cell is a cell derived from a mammal.

15. A host cell as defined in claim 14, wherein the host cell is a CHO cell, a dihydrofolate dehydrogenase-deficient strain of a CHO cell, or a COS cell.

16. A host cell as defined in claim 13, wherein the host cell is the transformant *E coil* strain pCR-Blunt II TOPO-F6-2/22 SANK 71002 (FERM BP-8142).

17. A process for producing a polypeptide having a 2',5'-oligoadenylate phosphodiesterase activity, comprising:
   [i] culturing a host cell as defined in claim 13; and
   [ii] harvesting a polypeptide having 2',5'-oligoadenylate phosphodiesterase activity from the culture.

18. A process for screening for a 2',5'-oligoadenylate phosphodiesterase activity inhibitor substance comprising:
   (a) contacting, in the presence or absence of a specimen, a host cell as defined in claim 13 with a nucleotide substrate comprising an adenylyl (2'-5')adenosine as a part of its structure;
   (b) measuring the amount of hydrolysis of the nucleotide substrate; and
   (c) judging the specimen as being positive, when the amount of hydrolysis in the presence of the specimen is lower than that in the absence of the specimen.

19. A process for screening for a 2',5'-oligoadenylate phosphodiesterase expression suppressor substance comprising:
   (a) incubating a host cell in the presence or absence of a specimen, said host cell being transformed with a recombinant plasmid DNA into which a polynucleotide as defined in claims 1, 3 or 5 has been inserted;
   (b) measuring the amount of transcription of said polynucleotide or the amount of translation of a polypeptide encoded by said polynucleotide, in the host cell or in an extracellular fluid thereof; and
   (c) judging the specimen as being positive, when the amount of transcription or the amount of translation in the presence of the specimen is lower than that in the absence of the specimen.

20. A process as defined in claim 18, wherein the host cell or the cell is incubated in the presence and/or absence of interferon in step (a).

21. A process for screening for a 2-5A system activator substance comprising:
   (a) incubating a host cell as defined in claim 13 in the presence or absence of a specimen;
   (b) measuring the amount of 2',5'oligoadenylate or the amount of RNA degradation by ribonuclease L in the host cell or in an extracellular fluid thereof; and
   (c) judging the specimen as being positive, when the amount of 2', 5'-oligoadenylate or the amount of RNA degradation by ribonuclease L in the presence of the specimen is greater than that in the absence of the specimen.

\* \* \* \* \*